(12) United States Patent
Lim et al.

(10) Patent No.: US 12,349,592 B2
(45) Date of Patent: *Jul. 1, 2025

(54) COMPOUND AND PHOTOELECTRIC DEVICE, IMAGE SENSOR, AND ELECTRONIC DEVICE INCLUDING THE SAME

(71) Applicant: Samsung Electronics Co., Ltd., Suwon-si (KR)

(72) Inventors: Seon-Jeong Lim, Yongin-si (KR); Norihito Ishii, Yokohama (JP); Katsunori Shibata, Hwaseong-si (KR); Yong Wan Jin, Seoul (KR); Taejin Choi, Suwon-si (KR); Kyung Bae Park, Hwaseong-si (KR); Sung Jun Park, Yongin-si (KR); Jisoo Shin, Suwon-si (KR); Sung Young Yun, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 894 days.

This patent is subject to a terminal disclaimer.

(21) Appl. No.: 17/146,850

(22) Filed: Jan. 12, 2021

(65) Prior Publication Data
US 2021/0234103 A1 Jul. 29, 2021

(30) Foreign Application Priority Data
Jan. 13, 2020 (KR) .................. 10-2020-0004232

(51) Int. Cl.
| | |
|---|---|
| C07D 471/16 | (2006.01) |
| C07D 471/14 | (2006.01) |
| C07D 495/04 | (2006.01) |
| C07D 517/04 | (2006.01) |
| C07D 517/12 | (2006.01) |
| C07D 517/14 | (2006.01) |
| C07D 517/16 | (2006.01) |
| C07D 517/20 | (2006.01) |
| C07D 517/22 | (2006.01) |
| C07F 7/08 | (2006.01) |
| H01L 27/146 | (2006.01) |
| H10K 30/30 | (2023.01) |
| H10K 39/32 | (2023.01) |
| H10K 85/40 | (2023.01) |
| H10K 85/60 | (2023.01) |
| H10K 19/20 | (2023.01) |

(52) U.S. Cl.
CPC ......... *H10K 85/657* (2023.02); *C07D 471/16* (2013.01); *C07D 517/16* (2013.01); *H10K 85/654* (2023.02); *H10K 85/6572* (2023.02); *H01L 27/14647* (2013.01); *H10K 19/20* (2023.02); *H10K 30/30* (2023.02); *H10K 39/32* (2023.02)

(58) Field of Classification Search
CPC .. C07D 471/16; C07D 517/16; C07D 517/12; C07D 517/14; C07D 517/22; C07D 471/14; C07D 495/04; C07D 517/04; C07D 517/20; H10K 85/657; H10K 85/654; H10K 85/6572; H10K 19/20; H10K 30/30; H10K 39/32; H10K 85/40; H10K 85/615; H10K 85/649; H01L 27/14647; H01L 27/14603; C07F 7/0816
See application file for complete search history.

(56) References Cited

U.S. PATENT DOCUMENTS

| | | |
|---|---|---|
| 8,525,577 B2 | 9/2013 | Yofu et al. |
| 9,818,956 B2 | 11/2017 | Ro et al. |
| 9,918,071 B2 | 3/2018 | Jeon et al. |
| 9,941,477 B2 | 4/2018 | Choi et al. |
| 9,960,362 B2 | 5/2018 | Bulliard et al. |
| 9,997,721 B2 | 6/2018 | Yamamoto et al. |
| 10,276,802 B2 | 4/2019 | Shibuya et al. |
| 10,290,812 B2 | 5/2019 | Lim et al. |

(Continued)

FOREIGN PATENT DOCUMENTS

| | | |
|---|---|---|
| CN | 105622573 A | 6/2016 |
| CN | 110964007 A | 4/2020 |

(Continued)

OTHER PUBLICATIONS

Extended European Search Report dated Jun. 7, 2021, issued in corresponding European Patent Application No. 21151295.9.

(Continued)

*Primary Examiner* — Amanda L. Aguirre
*Assistant Examiner* — Sagar Patel
(74) *Attorney, Agent, or Firm* — HARNESS, DICKEY & PIERCE, P.L.C.

(57) ABSTRACT

A compound of Chemical Formula 1, and an organic photoelectric device, an image sensor, and/or an electronic device including the same are disclosed:

[Chemical Formula 1]

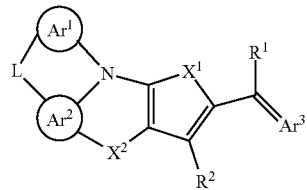

In Chemical Formula 1, each substituent is the same as defined in the detailed description.

27 Claims, 10 Drawing Sheets

(56) References Cited

U.S. PATENT DOCUMENTS

| | | |
|---|---|---|
| 10,326,083 B2 | 6/2019 | Yagi et al. |
| 10,461,256 B2 | 10/2019 | Choi et al. |
| 10,566,544 B2 | 2/2020 | Shibuya et al. |
| 2016/0111651 A1 | 4/2016 | Yun et al. |
| 2016/0211465 A1 | 7/2016 | Tadao et al. |
| 2017/0331050 A1 | 11/2017 | Yagi et al. |
| 2017/0346016 A1 | 11/2017 | Bulliard et al. |
| 2019/0123285 A1 | 4/2019 | Shin et al. |
| 2019/0131541 A1 | 5/2019 | Choi et al. |
| 2020/0194679 A1 | 6/2020 | Fukuzaki et al. |
| 2020/0212107 A1 | 7/2020 | Yoshioka et al. |
| 2021/0135121 A1 | 5/2021 | Mashiko et al. |
| 2021/0305320 A1* | 9/2021 | Lim ............... H10K 85/311 |
| 2022/0173167 A1* | 6/2022 | Lim ............... H01L 27/14667 |
| 2022/0216418 A1 | 7/2022 | Choi et al. |
| 2022/0289767 A1* | 7/2022 | Choi ............... H10K 85/636 |

FOREIGN PATENT DOCUMENTS

| | | |
|---|---|---|
| EP | 3026722 A1 | 6/2016 |
| EP | 3243822 A1 | 11/2017 |
| EP | 3473622 A1 | 4/2019 |
| EP | 3757108 A1 | 12/2020 |
| EP | 3770163 A1 | 1/2021 |
| EP | 4024484 A1 | 7/2022 |
| JP | 2017-095460 A | 6/2017 |
| KR | 2016-0052448 A | 5/2016 |
| KR | 20160062708 A | 6/2016 |
| KR | 2017-0114839 A | 10/2017 |
| KR | 2017-0126753 A | 11/2017 |
| KR | 2017-0137648 A | 12/2017 |
| KR | 20170135449 A | 12/2017 |
| KR | 20190044555 A | 4/2019 |
| WO | WO-2014051007 A1 | 4/2014 |
| WO | WO-2015016155 A1 | 2/2015 |
| WO | WO-2019049946 A1 | 3/2019 |
| WO | WO-2019054327 A1 | 3/2019 |
| WO | 2019/230562 A1 | 12/2019 |

OTHER PUBLICATIONS

Communication Pursuant to Article 94(3) EPC, dated Apr. 11, 2023, issued in corresponding European Patent Application No. 21151295.9.

Lutz Ackermann and Andreas Althammer, 'Domino N—H/C—H Bond Activation: Palladium-Catalyzed Synthesis of Annulated Heterocycles Using Dichloro(hetero)arenes' *Angewandte Chemie Int. Ed.*, vol. 46, 2007, pp. 1627-1629.

Hokuto Seo et al., 'Color Sensors with Three Vertically Stacked Organic Photodetectors' *Japanese Journal of Applied Physics*, vol. 46, No. 49, 2007, pp. L1240-L1242.

Satoshi Aihara et al., 'Stacked Image Sensor With Green- and Red-Sensitive Organic Photoconductive Films Applying Zinc Oxide Thin-Film Transistors to a Signal Readout Circuit' *IEEE Transactions on Electron Devices*, vol. 56, No. 11, Nov. 2009, pp. 2570-2576.

Mikio Ihama et al., 'CMOS Image Sensor with a Thin Overlaid Panchromatic Organic Photoconductive Layer for Sensors with Reduced Pixel Size' INP 1-4, *IDW* 2009, pp. 2123-2126.

Seon-Jeong Lim et al. 'Organic-on-silicon complementary metal-oxide-semiconductor colour image sensors' *Scientific Reports*, 5:7708, Jan. 2015.

Juha Alakarhu, 'Image Sensors and Image Quality in Mobile Phones' *International Image Sensor Workshop*, Jun. 2007.

Kazuko Takahashi et al., 'Efficient Synthesis of 2-IODO and 2-Dicyanomethyl Derivatives of Thiophene, Selenophene, Tellurophene, and Thieno[3,2-b]Thiophene' *Heterocycles*, vol. 43, No. 9, 1996, pp. 1927-1935.

Chinese Office Action dated Mar. 29, 2024 for corresponding Chinese Patent Application No. 202110043054.6 and its English-language translation.

Japanese Office Action dated Nov. 19, 2024 for corresponding Japanese Patent Application No. 2021-003662 and its English-language translation.

\* cited by examiner

COMPOUND AND PHOTOELECTRIC DEVICE, IMAGE SENSOR, AND ELECTRONIC DEVICE INCLUDING THE SAME

CROSS-REFERENCE TO RELATED APPLICATION

This application claims priority under 35 U.S.C. § 119, to and the benefit of, Korean Patent Application No. 10-2020-0004232 filed in the Korean Intellectual Property Office on Jan. 13, 2020, the entire contents of which are incorporated herein by reference.

BACKGROUND

1. Field

A compound and/or a photoelectric device, an image sensor, and/or an electronic device including the same are disclosed.

2. Description of Related Art

A photoelectric device converts light into an electrical signal using photoelectric effects, it may include a photodiode, a phototransistor, and the like, and it may be applied to an image sensor, a solar cell, an organic light emitting diode, and the like.

An image sensor including a photodiode requires high resolution and thus a small pixel. At present, a silicon photodiode is widely used, but it has a problem of deteriorated sensitivity since it has a small absorption area due to small pixels. Accordingly, an organic material that is capable of replacing silicon has been researched.

The organic material has a high absorption coefficient and selectively absorbs light in a particular wavelength region depending on a molecular structure, and thus may simultaneously replace a photodiode and a color filter and resultantly improve sensitivity and contribute to high integration.

SUMMARY

An embodiment provides a compound capable of selectively absorbing light in a green wavelength region and/or having excellent thermal stability.

Another embodiment provides a photoelectric device capable of selectively absorbing light in a green wavelength region and/or maintaining excellent efficiency even in a process under high temperature conditions.

Another embodiment provides an image sensor including the photoelectric device.

Another embodiment provides an electronic device including the image sensor.

According to an embodiment, a compound represented by Chemical Formula 1 is provided.

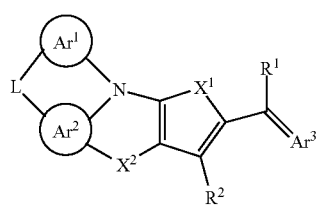

[Chemical Formula 1]

In Chemical Formula 1, $Ar^1$ and $Ar^2$ may independently be a substituted or unsubstituted C6 to C30 arene group, a substituted or unsubstituted C3 to C30 heteroarene group, or a condensed ring thereof, $X^1$ may be —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —CR$^f$R$^g$—, or —CR$^{ff}$R$^{gg}$—, wherein R$^{a1}$, R$^{a2}$, R$^b$, R$^c$, R$^d$, R$^e$, R$^f$, and R$^g$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of R$^{bb}$ and R$^{cc}$, R$^{dd}$ and R$^{ee}$, or R$^{ff}$ and R$^{gg}$ is linked with each other to provide a ring structure, $X^2$ may be —O—, —S—, —Se—, —Te—, —S(=O)—, —S(=O)$_2$—, —NR$^{a1}$—, —BR$^{a2}$—, —SiR$^b$R$^c$—, —SiR$^b$R$^c$—, —GeR$^d$R$^e$—, —GeR$^{dd}$R$^{ee}$—, —(CR$^f$R$^g$)$_{n1}$—, —(CR$^{ff}$R$^{gg}$)—, —(C(R$^m$)=C(R$^n$)—, —(C(R$^{mm}$)=C(R$^{nn}$))—, or —(C(R$^p$)=N))—, wherein R$^{a1}$, R$^{a2}$, R$^b$, R$^c$, R$^d$, R$^e$, R$^f$, R$^g$, R$^m$, R$^n$, and R$^p$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, at least one pair of R$^{bb}$ and R$^{cc}$, R$^{dd}$ and R$^{ee}$, R$^{ff}$ and R$^{gg}$, or R$^{mm}$ and R$^{nn}$ is linked with each other to provide a ring structure, and n1 of —(CR$^f$R$^g$)$_{n1}$— is 1 or 2, L may be —O—, —S—, —Se—, —Te—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —(CR$^f$R$^g$)$_{n1}$—, —(CR$^{ff}$R$^{gg}$)—, —(C(R$^m$)=C(R$^n$))—, —(C(R$^{mm}$)=C(R$^{nn}$))—, —(C(R$^p$)=N))—, or a single bond, wherein R$^{a1}$, R$^{a2}$, R$^b$, R$^c$, R$^d$, R$^e$, R$^f$, R$^g$, R$^m$, R$^n$, and R$^p$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of R$^{bb}$ and R$^{cc}$, R$^{dd}$ and R$^{ee}$, R$^{ff}$ and R$^{gg}$, or R$^{mm}$ and R$^{nn}$ is linked with each other to provide a ring structure, and n1 of —(CR$^f$R$^g$)$_{n1}$— is 1 or 2), when L is —NR$^{a1}$—, —BR$^{a2}$—, —SiR$^b$R$^c$—, —GeR$^d$R$^e$—, —(CR$^f$R$^g$)$_{n1}$—, —(C(R$^m$)=C(R$^n$))—, or —(C(R$^p$)=N))—, L is optionally linked with Ar$^1$ or Ar$^2$ to provide a ring structure, $Ar^3$ may be a substituted or unsubstituted C6 to C30 hydrocarbon cyclic group having at least one functional group selected from C=O, C=S, C=Se, and C=Te, a substituted or unsubstituted C2 to C30 heterocyclic group having at least one functional group selected from C=O, C=S, C=Se, and C=Te, or a fused ring thereof, and $R^1$ and $R^2$ may independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, a pentafluorosulfanyl group (—SF$_5$), a hydroxyl group, an amine group, a hydrazine group, a hydrazone group, a carboxyl group or a salt thereof, a sulfonic acid group or a salt thereof, a phosphoric acid group or a salt thereof, —SiR$^a$R$^b$R$^c$, wherein R$^a$, R$^b$, and R$^c$ may independently be hydrogen or a substituted or unsubstituted C1 to C10 alkyl group, or a combination thereof.

In some embodiments, the compound of Chemical Formula 1 may be represented by Chemical Formula 2A.

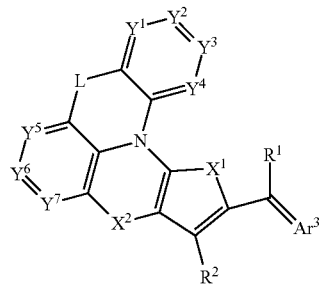

[Chemical Formula 2A]

In Chemical Formula 2A,

X$^1$, X$^2$, L, Ar$^3$, R$^1$, and R$^2$ are the same as in Chemical Formula 1, and Y$^1$ to Y$^7$ may independently be N or CR$^k$, wherein R$^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent R$^k$'s are linked to each other to provide a substituted or unsubstituted C6 to C30 arene group, a substituted or unsubstituted C3 to C30 heteroarene group, or a condensed ring thereof.

In some embodiments, in Chemical Formula 2A, Y$^4$ may be N or CR$^k$, wherein R$^k$ is a halogen, a cyano group, a C1 to C10 haloalkyl group, or a C1 to C10 cyanoalkyl group, or Y$^7$ may be N or CR$^k$, wherein R$^k$ may be a halogen, a cyano group, a C1 to C10 haloalkyl group, or a C1 to C10 cyanoalkyl group, and X$^2$ may be —O—, —S—, —Se—, —Te—, —S(=O)—, —S(=O)$_2$—, —NR$^{a1}$—, —BR$^{a2}$—, —SiR$^b$R$^c$—, —GeR$^d$R$^e$—, —(CR$^f$R$^g$)$_{n1}$—, —(C(R$^m$)=C(R$^n$))—, or —(C(R$^p$)=N))—, wherein R$^{a1}$, R$^{a2}$, R$^b$, R$^c$, R$^d$, R$^e$, R$^f$, R$^g$, R$^m$, R$^n$, and R$^p$ may independently be a halogen, a C1 to C20 haloalkyl group, or a C1 to C20 cyanoalkyl group.

In some embodiments, in Chemical Formula 2A, when Y$^1$ and Y$^5$ may be CR$^k$ and L is —NR$^{a1}$—, —BR$^{a2}$—, —SiR$^b$R$^c$—, —GeR$^d$R$^e$—, —(CR$^f$R$^g$)$_n$— or —(C(R$^m$)=C(R$^n$))—, at least one of Y$^1$ and Y$^5$ and L may be linked to each other to provide a fused ring. A structure in which Y$^5$ and L are linked to each other may be represented by Chemical Formula 2A-1, and a structure in which Y$^1$ and L are linked to each other may be represented by Chemical Formula 2A-2.

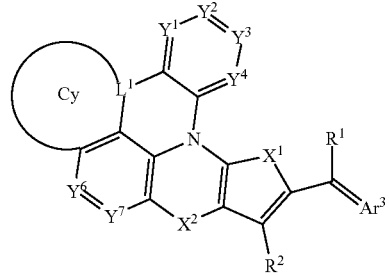

[Chemical Formula 2A-1]

In Chemical Formula 2A-1,

X$^1$, X$^2$, Ar$^3$, R$^1$, and R$^2$ are the same as in Chemical Formula 1,

L$^1$ may be N, B, Si, Ge, or C,

Y$^1$ to Y$^4$, Y$^6$, and Y$^7$ may independently be N or CR$^k$, wherein R$^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent R$^k$'s are linked to each other to provide a substituted or unsubstituted C6 to C30 arene group, a substituted or unsubstituted C3 to C30 heteroarene group, or a condensed ring thereof, and Cy may be a substituted or unsubstituted C6 to C30 arene group, a substituted or unsubstituted C3 to C30 heteroarene group, a substituted or unsubstituted C5 to C30 cycloalkene group, a substituted or unsubstituted C5 to C30 heterocycloalkene group or a condensed ring thereof.

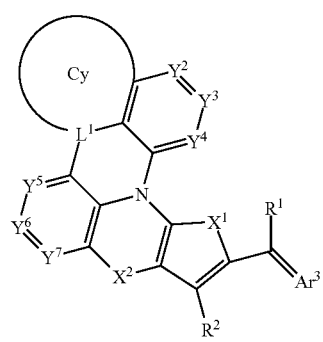

[Chemical Formula 2A-2]

In Chemical Formula 2A-2,

X$^1$, X$^2$, Ar$^3$, R$^1$, and R$^2$ are the same as in Chemical Formula 1,

L$^1$ may be N, B, Si, Ge, or C,

Y$^2$ to Y$^7$ may independently be N or CR$^k$, wherein R$^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent R$^k$'s are linked to each other to provide a substituted or unsubstituted C6 to C30 arene group, a substituted or unsubstituted C3 to C30 heteroarene group, or a condensed ring thereof, and Cy may be a substituted or unsubstituted C6 to C30 arene group, a substituted or unsubstituted C3 to C30 heteroarene group, a substituted or unsubstituted C5 to C30 cycloalkene group, a substituted or unsubstituted C5 to C30 heterocycloalkene group, or a condensed ring thereof.

In some embodiments, the compound of Chemical Formula 1 may be represented by Chemical Formula 2B.

[Chemical Formula 2B]

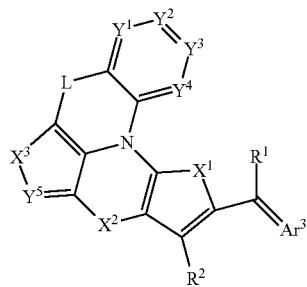

In Chemical Formula 2B, $X^1$, $X^2$, L, $Ar^3$, $R^1$, and $R^2$ are the same as in Chemical Formula 1, $Y^1$ to $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, and $X^3$ may be —O—, —S—, —Se—, —Te—, —S(=O)—, —S(=O)$_2$—, —$NR^{a1}$—, —$BR^{a2}$—, —$SiR^bR^c$—, —$SiR^{bb}R^{cc}$—, —$GeR^dR^e$—, —$GeR^{dd}R^{ee}$—, —$CR^fR^g$—, or —$CR^{ff}R^{gg}$—, wherein $R^{a1}$, $R^{a2}$, $R^b$, $R^c$, $R^d$, $R^e$, $R^f$, and $R^g$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of $R^{bb}$ and $R^{cc}$, $R^{dd}$ and $R^{ee}$, or $R^{ff}$ and $R^{gg}$ is linked to each other to provide a ring structure.

In Chemical Formula 2B, $Y^4$ may be N or $CR^k$, wherein $R^k$ may be a halogen, a cyano group, a C1 to C10 haloalkyl group, or a C1 to C10 cyanoalkyl group, or $Y^5$ may be N or $CR^k$, wherein $R^k$ may be a halogen, a cyano group, a C1 to C10 haloalkyl group, or a C1 to C10 cyanoalkyl group and $X^2$ may be —O—, —S—, —Se—, —Te—, —S(=O)—, —S(=O)$_2$—, —$NR^{a1}$—, —$BR^{a2}$—, —$SiR^bR^c$—, —$GeR^dR^e$—, —$(CR^fR^g)_{n1}$—, —$(C(R^m)=C(R^n))$—, or —$(C(R^p)=N)$—, wherein $R^{a1}$, $R^{a2}$, $R^b$, $R^c$, $R^d$, $R^e$, $R^f$, $R^g$, $R^m$, $R^n$, and $R^p$ may independently be a halogen, a C1 to C20 haloalkyl group, or a C1 to C20 cyanoalkyl group.

In some embodiments, in Chemical Formula 2B, when $Y^1$ is $CR^k$, $X^3$ is —$NR^{a1}$—, —$SiR^bR^c$—, —$GeR^dR^e$—, or —$CR^fR^g$—, and L is —$NR^{a1}$—, —$BR^{a2}$—, —$SiR^bR^c$—, —$GeR^dR^e$—, —$(CR^fR^g)_n$—, or —$(C(R^m)=C(R^n))$—, at least one of $Y^1$ and $X^3$ and L may be linked to each other to provide a fused ring. This structure may be represented by Chemical Formula 2B-1 or Chemical Formula 2B-2.

[Chemical Formula 2B-1]

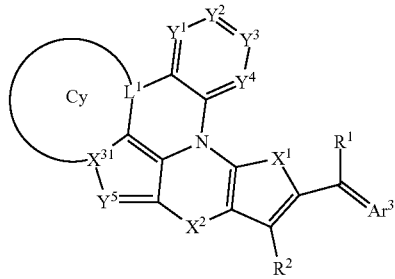

In Chemical Formula 2B-1, $X^1$, $X^2$, $Ar^3$, $R^1$, and $R^2$ are the same as in Chemical Formula 1, $L^1$ may be N, B, Si, Ge, or C, $X^{31}$ may be N, $SiR^b$, $GeR^d$, $CR^f$, Si, Ge, or C, wherein $R^b$, $R^d$, and $R^f$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, $Y^1$ to $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, and Cy is a substituted or unsubstituted C6 to C30 arene group, a substituted or unsubstituted C3 to C30 heteroarene group, a substituted or unsubstituted C5 to C30 cycloalkene group, a substituted or unsubstituted C5 to C30 heterocycloalkene group or a condensed ring thereof.

[Chemical Formula 2B-2]

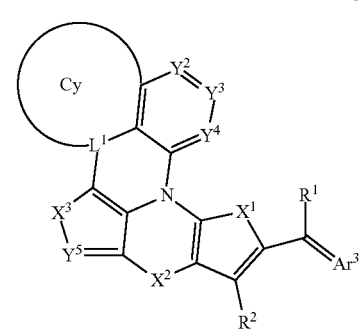

In Chemical Formula 2B-2, $X^1$, $X^2$, $Ar^3$, $R^1$, and $R^2$ are the same as in Chemical Formula 1, $X^3$ is the same as in Chemical Formula 2B, $L^1$ may be N, B, Si, Ge, or C, $Y^2$ to $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, and Cy may be a substituted or unsubstituted C6 to C30 arene group, a substituted or unsubstituted C3 to C30 heteroarene group, a substituted or unsubstituted C5 to C30 cycloalkene group, a substituted or unsubstituted C5 to C30 heterocycloalkene group or a condensed ring thereof.

In some embodiments, the compound of Chemical Formula 1 may be represented by Chemical Formula 2C.

[Chemical Formula 2C]

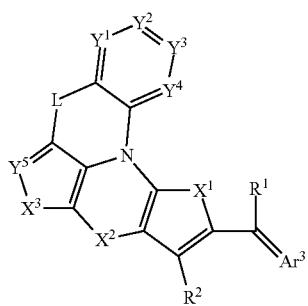

In Chemical Formula 2C, $X^1$, $X^2$, L, $Ar^3$, $R^1$, and $R^2$ are the same as in Chemical Formula 1, $Y^1$ to $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, and $X^3$ may be —O—, —S—, —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —CR$^f$R$^g$—, or —CR$^{ff}$R$^{gg}$—, wherein $R^{a1}$, $R^{a2}$, $R^b$, $R^c$, $R^d$, $R^e$, $R^f$, and $R^g$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of $R^{bb}$ and $R^{cc}$, $R^{dd}$ and $R^{ee}$, or $R^{ff}$ and $R^{gg}$ is linked to each other to provide a ring structure.

In some embodiments, in Chemical Formula 2C, $Y^4$ may be N or $CR^k$, wherein $R^k$ may be a halogen, a cyano group, a C1 to C10 haloalkyl group, or a C1 to C10 cyanoalkyl group, or $X^3$ may be —O—, —S—, —Se—, —Te—, —S(=O)—, —S(=O)$_2$—, —NR$^{a1}$—, —BR$^{a2}$—, —SiR$^b$R$^c$—, —GeR$^d$R$^e$—, or —CR$^f$R$^g$—, wherein $R^{a1}$, $R^{a2}$, $R^b$, $R^c$, $R^d$, $R^e$, $R^f$, $R^g$, $R^m$, $R^n$, and $R^p$ may independently be a halogen, a C1 to C20 haloalkyl group, or a C1 to C20 cyanoalkyl group and $X^2$ may be —O—, —S—, —Se—, —Te—, —S(=O)—, —S(=O)$_2$—, —NR$^{a1}$—, —BR$^{a2}$—, —SiR$^b$R$^c$—, —GeR$^d$R$^e$—, —(CR$^f$R$^g$)$_{n1}$—, —(C(R$^m$)=C(R$^n$))—, or —(C(R$^p$)=N))—, wherein $R^{a1}$, $R^{a2}$, $R^b$, $R^c$, $R^d$, $R^e$, $R^f$, $R^g$, $R^m$, $R^n$, and $R^p$ may independently be a halogen, a C1 to C20 haloalkyl group, or a C1 to C20 cyanoalkyl group.

In some embodiments, in Chemical Formula 2C, when $Y^5$ is $CR^k$ and L is —NR$^{a1}$—, —BR$^{a2}$—, —SiR$^b$R$^c$—, —GeR$^d$R$^e$—, —(CR$^f$R$^g$)$_n$—, or —(C(R$^m$)=C(R$^n$))—, $Y^5$ and L may be linked to each other to provide a fused ring. This structure may be represented by Chemical Formula 2C-1.

[Chemical Formula 2C-1]

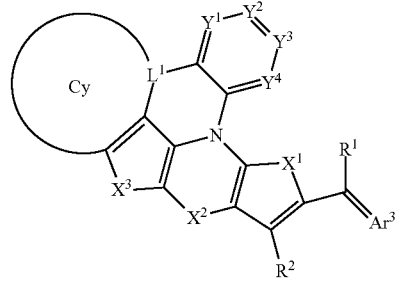

In Chemical Formula 2C-1, $X^1$, $X^2$, $Ar^3$, $R^1$, and $R^2$ are the same as in Chemical Formula 1, $X^3$ is the same as in Chemical Formula 20, $L^1$ may be N, B, Si, Ge, or C, $Y^1$ to $Y^4$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, and Cy may be a substituted or unsubstituted C6 to C30 arene group, a substituted or unsubstituted C3 to C30 heteroarene group, a substituted or unsubstituted C5 to C30 cycloalkene group, a substituted or unsubstituted C5 to C30 heterocycloalkene group or a condensed ring thereof.

In some embodiments, in Chemical Formula 20, L (—SiR$^b$R$^c$—, —GeR$^d$R$^e$—, —(CR$^f$R$^g$)$_n$—, or —(C(R$^m$)=C(R$^n$))—) and $Y^1$ ($CR^k$) may be linked to each other to provide a fused ring. This structure may be represented by Chemical Formula 2C-2.

[Chemical Formula 2C-2]

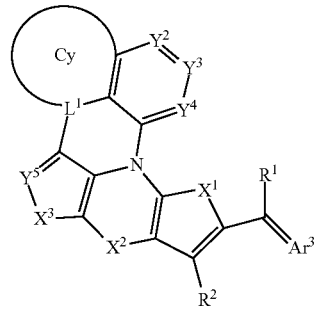

In Chemical Formula 2C-2, $X^1$, $X^2$, $Ar^3$, $R^1$, and $R^2$ are the same as in Chemical Formula 1, $X^3$ is the same as in Chemical Formula 2C,
$L^1$ may be N, B, Si, Ge, or C,
$Y^2$ to $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, and
Cy may be a substituted or unsubstituted C6 to C30 arene group, a substituted or unsubstituted C3 to C30 heteroarene group, a substituted or unsubstituted C5 to C30 cycloalkene group, a substituted or unsubstituted C5 to C30 heterocycloalkene group or a condensed ring thereof.

In some embodiments, the compound of Chemical Formula 1 may be represented by Chemical Formula 2D.

[Chemical Formula 2D]

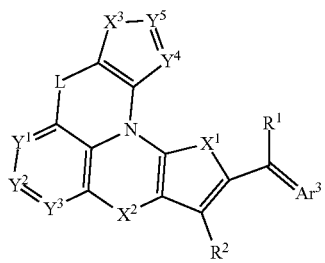

In Chemical Formula 2D,
$X^1$, $X^2$, L, $Ar^3$, $R^1$, and $R^2$ are the same as in Chemical Formula 1,
$Y^1$ to $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s may be linked to each other to provide a substituted or unsubstituted C6 to C30 arene group, a substituted or unsubstituted C3 to C30 heteroarene group, or a condensed ring thereof, and
$X^3$ may be —O—, —S—, —Se—, —Te—, —S(=O)—, —S(=O)$_2$—, —$NR^{a1}$—, —$BR^{a2}$—, —$SiR^bR^c$—, —$SiR^{bb}R^{cc}$—, —$GeR^dR^e$—, —$GeR^{dd}R^{ee}$—, —$CR^fR^g$—, or —$CR^{ff}R^{gg}$—, wherein $R^{a1}$, $R^{a2}$, $R^b$, $R^c$, $R^d$, $R^e$, $R^f$, and $R^g$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one of $R^{bb}$ and $R^{cc}$, $R^{dd}$ and $R^{ee}$, or $R^{ff}$ and $R^{gg}$ may be linked to each other to provide a ring structure.

In some embodiments, in Chemical Formula 2D, $Y^4$ may be N or $CR^k$, wherein $R^k$ is a halogen, a cyano group, a C1 to C10 haloalkyl group, or a C1 to C10 cyanoalkyl group, or $Y^3$ may be N or $CR^k$, wherein $R^k$ is a halogen, a cyano group, a C1 to C10 haloalkyl group, or a C1 to C10 cyanoalkyl group and $X^2$ may be —O—, —S—, —Se—, —Te—, —S(=O)—, —S(=O)$_2$—, —$NR^{a1}$—, —$BR^{a2}$—, —$SiR^bR^c$—, —$GeR^dR^e$—, —$(CR^fR^g)_{n1}$—, —$(C(R^m)=C(R^n))$—, or —$(C(R^p)=N))$—, wherein $R^{a1}$, $R^{a2}$, $R^b$, $R^c$, $R^d$, $R^e$, $R^f$, $R^g$, $R^m$, $R^n$, and $R^p$ may independently be a halogen, a C1 to C20 haloalkyl group, or a C1 to C20 cyanoalkyl group.

In some embodiments, in Chemical Formula 2D, when $Y^1$ is $CR^k$ and L is —$NR^{a1}$—, —$BR^{a2}$—, —$SiR^bR^c$—, —$GeR^dR^e$—, —$(CR^fR^g)_{n1}$—, or —$(C(R^m)=C(R^n))$—, $Y^1$ and L may be linked to each other to provide a fused ring. This structure may be represented by Chemical Formula 2D-1.

[Chemical Formula 2D-1]

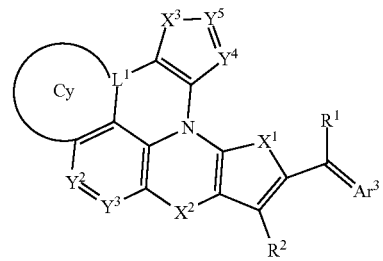

In Chemical Formula 2D-1,
$X^1$, $X^2$, $Ar^3$, $R^1$, and $R^2$ are the same as in Chemical Formula 1,
$X^3$ is the same as in Chemical Formula 2D,
$L^1$ may be N, B, Si, Ge, or C,
$Y^2$ to $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, and
Cy may be a substituted or unsubstituted C6 to C30 arene group, a substituted or unsubstituted C3 to C30 heteroarene group, a substituted or unsubstituted C5 to C30 cycloalkene group, a substituted or unsubstituted C5 to C30 heterocycloalkene group or a condensed ring thereof.

In Chemical Formula 2D, when $X^3$ is —$NR^{a1}$—, —$BR^{a2}$—, —$SiR^bR^c$—, —$GeR^dR^e$—, or —$CR^fR^g$— and L is —$SiR^bR^c$—, —$GeR^dR^e$—, —$(CR^fR^g)_n$—, or —$(C(R^m)=C(R^n))$—, $X^3$ and L may be linked to each other to provide a fused ring. This structure may be represented by Chemical Formula 2D-2.

[Chemical Formula 2D-2]

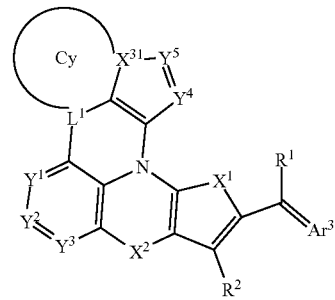

$X^1$, $X^2$, $Ar^3$, $R^1$, and $R^2$ are the same as in Chemical Formula 1, $X^{31}$ may be N, $SiR^b$, $GeR^d$, $CR^f$, Si, Ge, or C, wherein $R^b$, $R^d$, and $R^f$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, $L^1$ may be N, B, Si, Ge, or C, $Y^1$ to $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, and Cy may be a substituted or unsubstituted C6 to C30 arene group, a substituted or unsubstituted C3 to C30 heteroarene group, a substituted or unsubstituted C5 to C30 cycloalkene group, a substituted or unsubstituted C5 to C30 heterocycloalkene group or a condensed ring thereof.

In some embodiments, the compound of Chemical Formula 1 may be represented by Chemical Formula 2E.

[Chemical Formula 2E]

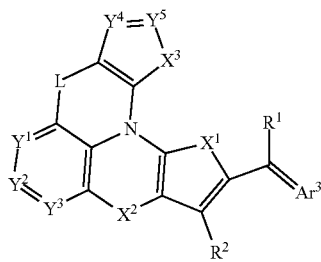

In Chemical Formula 2E, $X^1$, $X^2$, L, $Ar^3$, $R^1$, and $R^2$ are the same as in Chemical Formula 1, $X^3$ may be —O—, —S—, —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —CR$^f$R$^g$—, or —CR$^{ff}$R$^{gg}$—, wherein R$^{a1}$, R$^{a2}$, R$^b$, R$^c$, R$^d$, R$^e$, R$^f$, and R$^g$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of R$^{bb}$ and R$^{cc}$, R$^{dd}$ and R$^{ee}$, or R$^{ff}$ and R$^{gg}$ is linked to each other to provide a ring structure, and $Y^1$ to $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof.

In some embodiments, in Chemical Formula 2E, $X^3$ may be —O—, —S—, —Se—, —Te—, —S(=O)—, —S(=O)$_2$—, —NR$^{a1}$—, —BR$^{a2}$—, —SiR$^b$R$^c$—, —GeR$^d$R$^e$—, or —CR$^f$R$^g$—, wherein R$^{a1}$, R$^{a2}$, R$^b$, R$^c$, R$^d$, R$^e$, R$^f$, and R$^g$ may independently be a halogen, a C1 to C20 haloalkyl group, or a C1 to C20 cyanoalkyl group, or $Y^3$ may be N or $CR^k$, wherein $R^k$ is a halogen, a cyano group, a C1 to C10 haloalkyl group, or a C1 to C10 cyanoalkyl group and $X^2$ may be —O—, —S—, —Se—, —Te—, —S(=O)—, —S(=O)$_2$—, —NR$^{a1}$—, —BR$^{a2}$—, —SiR$^b$R$^c$—, —GeR$^d$R$^e$—, —(CR$^f$R$^g$)$_{n1}$—, —(C(R$^m$)=C(R$^n$))—, or —(C(R$^p$)=N))—, wherein R$^{a1}$, R$^{a2}$, R$^b$, R$^c$, R$^d$, R$^e$, R$^f$, R$^g$, R$^m$, R$^n$ and R$^p$ may independently be a halogen, a C1 to C20 haloalkyl group, or a C1 to C20 cyanoalkyl group.

In some embodiments, in Chemical Formula 2E, when $Y^1$ and $Y^4$ are $CR^k$ and L is —NR$^{a1}$—, —BR$^{a2}$—, —SiR$^b$R$^c$—, —GeR$^d$R$^e$—, —(CR$^f$R$^g$)$_n$—, or —(C(R$^m$)=C(R$^n$))—, one of $Y^1$ and $Y^4$ and L may be linked to each other to provide a fused ring. This structure may be represented by Chemical Formula 2E-1 or Chemical Formula 2E-2.

[Chemical Formula 2E-1]

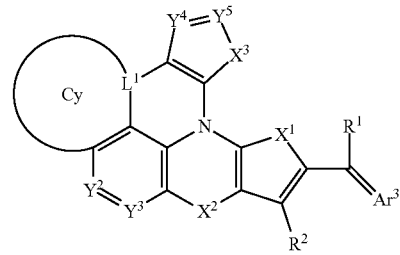

In Chemical Formula 2E-1, $X^1$, $X^2$, $Ar^3$, $R^1$, and $R^2$ are the same as in Chemical Formula 1, $X^3$ is the same as in Chemical Formula 2E, $L^1$ may be N, B, Si, Ge, or C, $Y^2$ to $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, and Cy may be a substituted or unsubstituted C6 to C30 arene group, a substituted or unsubstituted C3 to C30 heteroarene group, a substituted or unsubstituted C5 to C30 cycloalkene group, a substituted or unsubstituted C5 to C30 heterocycloalkene group or a condensed ring thereof.

[Chemical Formula 2E-2]

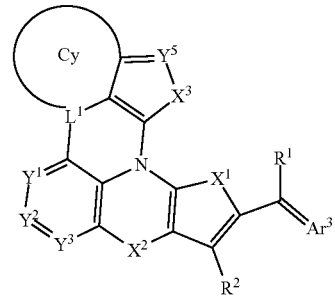

In Chemical Formula 2E-2, $X^1$, $X^2$, $Ar^3$, $R^1$, and $R^2$ are the same as in Chemical Formula 1, $X^3$ is the same as in Chemical Formula 2E, $L^1$ may be N, B, Si, Ge, or C, $Y^1$ to $Y^3$ and $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, and Cy may be a substituted or unsubstituted C6 to C30 arene group, a substituted or unsubstituted C3 to C30 heteroarene group, a substituted or unsubstituted C5 to C30 cycloalkene group, a substituted or unsubstituted C5 to C30 heterocycloalkene group or a condensed ring thereof.

In some embodiments, in $X^1$, $X^2$, and L of Chemical Formula 1, the ring structure may be a spiro structure or a fused ring structure.

In some embodiments, the spiro structure may include a moiety represented by Chemical Formula 3.

[Chemical Formula 3]

(1)

(2)

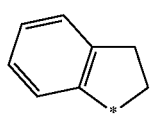

(3)

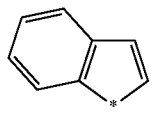

(4)

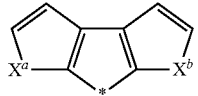

(5)

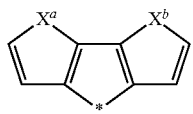

(6)

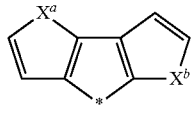

(7)

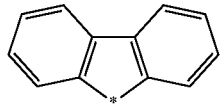

(8)

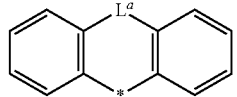

(9)

In Chemical Formula 3, $X^a$ and $X^b$ may independently be —O—, —S—, —Se—, —Te—, —S(=O)—, —S(=O)$_2$—, —$NR^{a1}$—, —$BR^{a2}$—, —$SiR^bR^c$—, —$SiR^{bb}R^{cc}$—, —$GeR^dR^e$—, or —$GeR^{dd}R^{ee}$—, wherein $R^{a1}$, $R^{a2}$, $R^b$, $R^c$, $R^d$ and $R^e$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of $R^{bb}$ and $R^{cc}$ or $R^{dd}$ and $R^{ee}$ may be linked to each other to provide a ring structure, $L^a$ may be —O—, —S—, —Se—, —Te—, —$NR^{a1}$—, —$BR^{a2}$—, —$SiR^bR^c$—, —$GeR^dR^e$—, —$(CR^fR^g)_{n1}$—, —$(C(R^p)=N)$—, or a single bond, wherein $R^{a1}$, $R^{a2}$, $R^b$, $R^c$, $R^d$, $R^e$, $R^f$, $R^g$ and $R^p$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and hydrogen of each ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

In some embodiments, in Chemical Formula 3, one or more CH present in the aromatic ring of the moieties (3), (4), (5), (6), and (7) may be replaced by N.

In some embodiments, in Chemical Formula 1, $Ar^3$ may be a cyclic group represented by Chemical Formula 4.

[Chemical Formula 4]

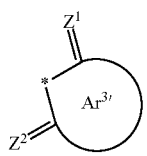

In Chemical Formula 4, $Ar^{3'}$ may be a substituted or unsubstituted C6 to C30 aryl group or a substituted or unsubstituted C3 to C30 heteroaryl group, $Z^1$ may be O, S, Se, or Te, and $Z^2$ may be O, S, Se, Te, or $CR^aR^b$, wherein $R^a$ and $R^b$ may independently be hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group.

In some embodiments, in Chemical Formula 1, $Ar^3$ may be a cyclic group represented by one of Chemical Formula 5A to Chemical Formula 5F.

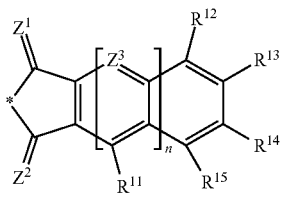

[Chemical Formula 5A]

In Chemical Formula 5A, $Z^1$ may be O, S, Se, or Te, $Z^2$ may be O, S, Se, Te, or $CR^aR^b$, wherein $R^a$ and $R^b$ may independently be hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $Z^3$ may be N or $CR^c$, wherein $R^c$ is hydrogen, deuterium, or a substituted or unsubstituted C1 to C10 alkyl group, $R^{11}$, $R^{12}$, $R^{13}$, $R^{14}$, and $R^{15}$ may be the same or different and may independently be hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof wherein $R^{12}$ and $R^{13}$ and $R^{14}$ and $R^{15}$ may independently be present or are linked to each other to provide a fused aromatic ring, n may be 0 or 1, and

* may be a linking point.

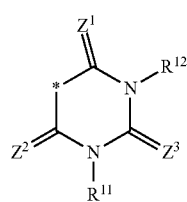

[Chemical Formula 5B]

In Chemical Formula 5B, $Z^1$ may be O, S, Se, or Te, $Z^2$ may be O, S, Se, Te, or $CR^aR^b$, wherein $R^a$ and $R^b$ may independently be hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $Z^3$ may be O, S, Se, Te, or $C(R^a)(CN)$, wherein $R^a$ is hydrogen, a cyano group (—CN), or a C1 to C10 alkyl group, $R^{11}$ and $R^{12}$ may independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* may be a linking point.

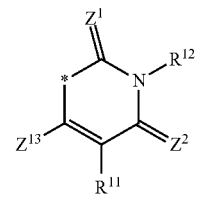

[Chemical Formula 5C]

In Chemical Formula 5C, $Z^1$ may be O, S, Se, or Te, $Z^2$ may be O, S, Se, Te, or $CR^aR^b$, wherein $R^a$ and $R^b$ may independently be hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $R^{11}$, $R^{12}$, and $R^{13}$ may be the same or different and may independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* may be a linking point.

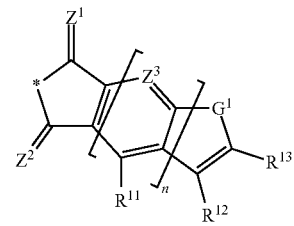

[Chemical Formula 5D]

In Chemical Formula 5D, $Z^1$ may be O, S, Se, or Te, $Z^2$ may be O, S, Se, Te, or $CR^aR^b$, wherein $R^a$ and $R^b$ may independently be hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $Z^3$ may be N or $CR^c$, wherein $R^c$ may be hydrogen or a substituted or unsubstituted C1 to C10 alkyl group, $G^1$ may be O, S, Se, Te, $SiR^xR^y$, or $GeR^zR^y$, wherein $R^x$, $R^y$, $R^z$, and $R^w$ may be the same or different and may independently be hydrogen, deuterium, a halogen, a substituted or unsubstituted C1 to C20 alkyl group, or a substituted or unsubstituted C6 to C20 aryl group, $R^{11}$, $R^{12}$, and $R^{13}$ may be the same or different and may independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, wherein $R^{12}$ and $R^{13}$ may independently be present or are linked to each other to provide a fused aromatic ring, n may be 0 or 1, and

* may be a linking point.

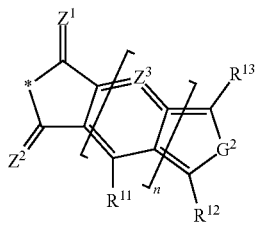

[Chemical Formula 5E]

In Chemical Formula 5E, $Z^1$ may be O, S, Se, or Te, $Z^2$ may be O, S, Se, Te, or $CR^aR^b$, wherein $R^a$ and $R^b$ may independently be hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $Z^3$ may be N or $CR^c$, wherein $R^c$ may be hydrogen or a substituted or unsubstituted C1 to C10 alkyl group, $G^2$ may be O, S, Se, Te, $SiR^xR^y$, or $GeR^zR^w$, wherein $R^x$, $R^y$, $R^z$, and $R^w$ may be the same or different and may independently be hydrogen, deuterium, a halogen, a substituted or unsubstituted C1 to C20 alkyl group, or a substituted or unsubstituted C6 to C20 aryl group, $R^{11}$, $R^{12}$, and $R^{13}$ may be the same or different and may independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, n may be 0 or 1, and

* may be a linking point.

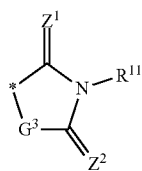

[Chemical Formula 5F]

In Chemical Formula 5F, $Z^1$ may be O, S, Se, or Te, $Z^2$ may be O, S, Se, Te, or $CR^aR^b$, wherein $R^a$ and $R^b$ may independently be hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $R^{11}$ may be hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and $G^3$ may be O, S, Se, Te, $SiR^xR^y$, or $GeR^zR^w$, wherein $R^x$, $R^y$, $R^z$, and $R^w$ may be the same or different and may independently be hydrogen, deuterium, a halogen, a substituted or unsubstituted C1 to C20 alkyl group, or a substituted or unsubstituted C6 to C20 aryl group.

In some embodiments, the compound may have a maximum absorption wavelength ($\lambda_{max}$) in a wavelength range of greater than or equal to about 500 nm and less than or equal to about 600 nm in a thin film state.

In some embodiments, the compound may exhibit a light absorption curve having a full width at half maximum (FWHM) in a thin film state of about 50 nm to about 110 nm.

In some embodiments, in Chemical Formula 1,

L may be a single bond, and $Ar^1$ and $Ar^2$ independently may be a substituted or unsubstituted C6 to C30 arene group or a substituted or unsubstituted C3 to C30 heteroarene group.

In some embodiments, in Chemical Formula 1, $R^1$ and $R^2$ independently may be hydrogen, deuterium, or a substituted or unsubstituted C1 to C30 alkyl group, and $Ar^1$ and $Ar^2$ independently may be a substituted or unsubstituted C6 to C30 arene group.

In some embodiments, in Chemical Formula 1, $X^2$ may be $-(CR^fR^g)_{n1}-$, $-(CR^{ff}R^{gg})-$, $-(C(R^m)=C(R^n))-$, $-(C(R^{mm})=C(R^{nn}))-$, or $-(C(R^p)=N))-$, wherein $R^f$, $R^g$, $R^m$, $R^n$, and $R^p$ are independently hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, at least one pair of $R^{ff}$ and $R^{gg}$, or $R^{mm}$ and $R^{nn}$ may be linked with each other to provide a ring structure, and n1 of $-(CR^fR^g)_{n1}-$ is 1 or 2.

In some embodiments, in Chemical Formula 1, $Ar^3$ may be a cyclic group represented by one of Chemical Formula 5A to Chemical Formula 5B:

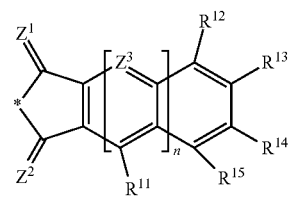

[Chemical Formula 5A]

wherein, in Chemical Formula 5A, $Z^1$ and $Z^2$ independently may be O, S, Se, or Te, n may be 0, $R^{12}$, $R^{13}$, $R^{14}$, and $R^{15}$ independently may be hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), or a cyano-containing group, and

* may be a linking point,

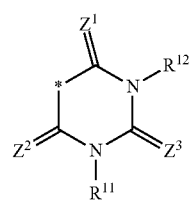

[Chemical Formula 5B]

wherein, in Chemical Formula 5B, $Z^1$ and $Z^2$ independently may be O, S, Se, or Te, $Z^3$ may be O, S, Se, Te, or $C(R^a)(CN)$, wherein $R^a$ is hydrogen, a cyano group (—CN), or a C1 to C10 alkyl group, $Z^3$ may be different than $Z^1$ and $Z^2$, $R^{11}$ and $R^{12}$ independently may be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* may be a linking point.

According to another embodiment, a photoelectric device (e.g., organic photoelectric device) includes a first electrode and a second electrode facing each other, and an active layer between the first electrode and the second electrode and including the compound represented by Chemical Formula 1.

According to another embodiment, an image sensor including the photoelectric device is provided.

In some embodiments, the image sensor may include a semiconductor substrate integrated with a plurality of first photo-sensing devices configured to sense light in a blue wavelength region and a plurality of second photo-sensing devices configured to sense light in a red wavelength region, and the photoelectric device may be on the semiconductor substrate and configured to sense light in a green wavelength region.

In some embodiments, the first photo-sensing device and the second photo-sensing device may be stacked in a vertical direction on a semiconductor substrate.

In some embodiments, the image sensor may further include a color filter layer including a blue filter configured to selectively transmit light in a blue wavelength region and a red filter configured to selectively transmit light in a red wavelength region.

In some embodiments, the image sensor may include a green photoelectric device that is the photoelectric device, a blue photoelectric device configured to sense light in a blue wavelength region, and a red photoelectric device configured to sense light in a red wavelength region, which may be stacked.

According to another embodiment, an electronic device including the image sensor is provided.

A compound capable of selectively absorbing light in a green wavelength region and excellent in thermal stability and charge mobility is provided. The wavelength selectivity in the green wavelength region by the compound may be increased to improve efficiency of the device, and a photoelectric device, an image sensor, and an electronic device in which performance is not degraded even in a high-temperature process are provided.

DETAILED DESCRIPTION

Figure 1:
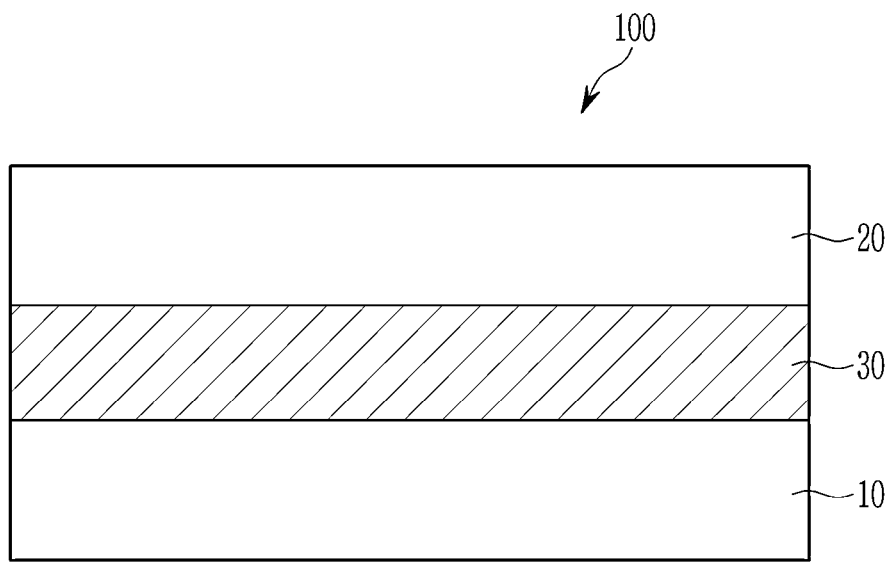
FIG. 1 is a cross-sectional view showing a photoelectric device according to an embodiment.

Hereinafter, embodiments are described in detail so that those of ordinary skill in the art can easily implement them. However, a structure that is actually applied may be implemented in various different forms, and is not limited to the embodiments described herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

As used herein, "at least one of A, B, or C," "one of A, B, C, or a combination thereof" and "one of A, B, C, and a combination thereof" refer to each constituent element, and a combination thereof (e.g., A; B; C; A and B; A and C; B and C; or A, B and C).

As used herein, when specific definition is not otherwise provided, "substituted" refers to replacement of a hydrogen of a compound or a functional group by a halogen atom (F, Br, Cl or I), a hydroxy group, a nitro group, a cyano group, an azido group, an amidino group, an amine group (—NR'R", wherein R' and R" are the same or different, and a hydrogen atom, a C1 to C20 alkyl group or a C6 to C30 aryl group), a hydrazino group, a hydrazono group, a carbonyl group, a carbamyl group, a thiol group, an ester group, a carboxyl group or a salt thereof, sulfonic acid group or a salt thereof, a phosphoric acid group or a salt thereof, a C1 to C20 alkyl group, a C1 to C20 alkoxy group, a C2 to C20 alkenyl group, a C2 to C20 alkynyl group, a C6 to C30 aryl group, a C7 to C30 arylalkyl group, a C2 to C20 heteroaryl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, or a combination thereof.

The "arene group" refers to a hydrocarbon ring group having an aromatic ring, and includes monocyclic and multicyclic hydrocarbon ring groups, and additional rings of the multicyclic hydrocarbon ring group may be an aromatic ring or a non-aromatic ring. The arene group may be a C6 to C30 arene group, a C6 to C20 arene group, or a C6 to C10 arene group.

"Heteroarene group" refers to an arene group including 1 to 3 heteroatoms selected from N, O, S, P, and Si in the ring. The heteroarene group may be a C3 to C30 heteroarene group, a C3 to C20 heteroarene group, or a C3 to C10 heteroarene group.

As used herein, "hydrocarbon cyclic group" may be a C3 to C30 hydrocarbon cyclic group. The hydrocarbon cyclic group may be an aromatic hydrocarbon cyclic group (e.g., C6 to C30 arene group, C6 to C20 arene group, or C6 to C10 arene group or C6 to C30 aryl group, C6 to C20 aryl group, or C6 to C10 aryl group), an alicyclic hydrocarbon cyclic group (e.g., C3 to C30 cycloalkyl group, C5 to C30 cycloalkyl group, C3 to C20 cycloalkyl group or C3 to C10 cycloalkyl group), or a fused ring group thereof. For example, the fused ring group may refer to a fused ring of an aromatic ring (arene ring) and a non-aromatic ring (alicyclic ring), for example a fused ring in which at least one aromatic ring (arene ring) such as a C6 to C30 arene group, a C6 to C20 arene group, or a C6 to C10 arene group or a C6 to C30 aryl group, a C6 to C20 aryl group, or a C6 to C10 aryl group and at least one non-aromatic ring (alicyclic ring) such as a C3 to C30 cycloalkyl group, a C3 to C20 cycloalkyl group, or a C3 to C10 cycloalkyl group are fused to each other.

As used herein, the "heterocyclic group" may be a C2 to C30 heterocyclic group. The heterocyclic group may be a cyclic group in which at least one, for example 1 to 3 carbons of an aromatic hydrocarbon cyclic group (e.g., a C6 to C30 arene group, a C6 to C20 arene group, or a C6 to C10 arene group or a C6 to C30 aryl group, a C6 to C20 aryl group, or a C6 to C10 aryl group), an alicyclic hydrocarbon cyclic group (e.g., a C3 to C30 cycloalkyl group, a C3 to C20 cycloalkyl group, or a C3 to C10 cycloalkyl group), and a fused ring group thereof are replaced by a heteroatom selected from N, O, S, P, and Si. In addition, at least one carbon atom of the heterocyclic group may be replaced by a thiocarbonyl group (C=S).

As used herein, when specific definition is not otherwise provided, "hetero" refers to one including 1 to 3 heteroatoms selected from N, O, S, P, and Si.

As used herein, "alkyl group" refers to a monovalent linear or branched saturated hydrocarbon group, for example a methyl group, an ethyl group, a propyl group, an isopropyl group, an n-butyl group, an isobutyl group, a t-butyl group, a pentyl group, a hexyl group, and the like.

As used herein, "cycloalkyl group" refers to a monovalent hydrocarbon cyclic group in which the atoms of the cycle are carbon, for example a cyclopropyl group, a cyclobutyl group, a cyclopentyl group, or a cyclohexyl group.

As used herein, "aryl group" refers to a cyclic functional group wherein all elements of the cycle have p-orbitals which form conjugation, and may be a monocyclic, polycyclic or fused ring polycyclic (e.g., rings sharing adjacent pairs of carbon atoms) functional group.

As used herein, when a definition is not otherwise provided, "cyano-containing group" refers to a monovalent group such as a C1 to C30 alkyl group, a C2 to C30 alkenyl group, or a C2 to C30 alkynyl group where at least one hydrogen is substituted with a cyano group. The cyano-containing group also refers to a divalent group such as =$CR^{x'}$—$(CR^xR^y)_p$—$CR^y(CN)_2$ wherein $R^x$, $R^y$, $R^{x'}$, and $R^{y'}$ are each independently hydrogen or a C1 to C10 alkyl group and p is an integer of 0 to 10 (or 1 to 10). Specific examples of the cyano-containing group may be a dicyanomethyl group, a dicyanovinyl group, a cyanoethynyl group, and the like. As used herein, the cyano-containing group does not include a functional group including a cyano group (—CN) alone.

As used herein, when a definition is not otherwise provided, "aromatic hydrocarbon group" may include a C6 to C30 arene group such as a phenyl group and a naphthyl group, a C6 to C30 aryl group, and a C6 to C30 arylene group, but is not limited thereto.

As used herein, when a definition is not otherwise provided, "aliphatic hydrocarbon group" may include a C1 to C15 alkyl group such as a methyl group, an ethyl group, a propyl group, and the like, a C1 to C15 alkylene group, a C2 to C15 alkenyl group such as an ethenyl group or a propenyl group, a C2 to C15 alkynyl group such as an ethynyl group or a propynyl group, but is not limited thereto.

As used herein, when a definition is not otherwise provided, "aromatic ring" refers to a C6 to C10 hydrocarbon cyclic group (e.g., a C6 to C10 aryl group) providing a conjugated structure or a C2 to C10 heterocyclic group (e.g., a C2 to C10 heteroaryl group) providing a conjugated structure.

As used herein, when a definition is not otherwise provided, "spiro structure" may be a substituted or unsubstituted C5 to C30 hydrocarbon ring group, a substituted or unsubstituted C2 to C30 heterocyclic group, or a fused ring thereof, which shares one atom with the ring containing $X^1$, $X^2$, or L in Chemical Formula 1. The C5 to C30 hydrocarbon cyclic group may be for example a substituted or unsubstituted C5 to C30 cycloalkyl group (e.g., a substituted or unsubstituted C5 to C20 cycloalkyl group or a substituted or unsubstituted C5 to C10 cycloalkyl group) or a substituted or unsubstituted C6 to C30 aryl group (e.g., a substituted or unsubstituted C6 to C20 aryl group, or a substituted or unsubstituted C6 to C10 aryl group) and the substituted or unsubstituted C2 to C30 heterocyclic group may be for example a substituted or unsubstituted C2 to C20 heterocycloalkyl group (e.g., a substituted or unsubstituted C2 to C10 heterocycloalkyl group) or a substituted or unsubstituted C2 to C20 heteroaryl group (e.g., a substituted or unsubstituted C2 to C10 heteroaryl group).

As used herein, when a definition is not otherwise provided, "fused ring" is a fused ring of two or more substituted or unsubstituted C5 to C30 hydrocarbon ring groups, a fused ring of two or more substituted or unsubstituted C2 to C30 heterocyclic groups, or a fused ring of a substituted or unsubstituted C5 to C30 hydrocarbon ring group and a substituted or unsubstituted C2 to C30 heterocyclic group (e.g., a fluorenyl group). Herein, the hydrocarbon cyclic group and the hetero cyclic group are as defined above.

As used herein, when a definition is not otherwise provided, "combination" refers to a mixture of two or more, substitution in which one substituent is substituted with another substituent, fusion with each other, or a linkage to each other by a single bond or a C1 to C10 alkylene group.

When the term "about" is used in this specification in connection with a numerical value, it is intended that the associated numerical value includes a manufacturing or operational tolerance (e.g., +10%) around the stated numerical value.

Hereinafter, a compound according to an embodiment is described. The compound is represented by Chemical Formula 1.

[Chemical Formula 1]

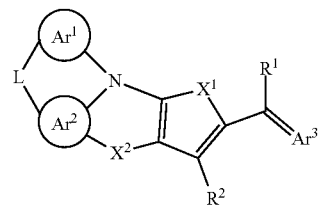

In Chemical Formula 1,

Ar$^1$ and Ar$^2$ may independently be a substituted or unsubstituted C6 to C30 arene group, a substituted or unsubstituted C3 to C30 heteroarene group, or a condensed ring thereof, X$^1$ may be —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —CR$^f$R$^g$—, or —CR$^{ff}$R$^{gg}$—, wherein R$^{a1}$, R$^{a2}$, R$^b$, R$^c$, R$^d$, R$^e$, R$^f$, and R$^g$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of R$^{bb}$ and R$^{cc}$, R$^{dd}$ and R$^{ee}$, or R$^{ff}$ and R$^{gg}$ is linked with each other to provide a ring structure, X$^2$ may be —O—, —S—, —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —(CR$^f$R$^g$)$_{n1}$—, —(CR$^{ff}$R$^{gg}$)—, —(C(R$^m$)=C(R$^n$))—, —(C(R$^{mm}$)=C(R$^{nn}$))—, or —(C(R$^p$)=N))—, wherein R$^{a1}$, R$^{a2}$, R$^b$, R$^c$, R$^d$, R$^e$, R$^f$, R$^g$, R$^m$, R$^n$, and R$^p$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, at least one pair of R$^{bb}$ and R$^{cc}$, R$^{dd}$ and R$^{ee}$, R$^{ff}$ and R$^{gg}$, or R$^{mm}$ and R$^{nn}$ is linked with each other to provide a ring structure, and n1 of —(CR$^f$R$^g$)$_{n1}$— is 1 or 2, L may be —O—, —S—, —Se—, —Te—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —(CR$^f$R$^g$)$_{n1}$—, —(CR$^{ff}$R$^{gg}$)—, —(C(R$^m$)=C(R$^n$))—, —(C(R$^{mm}$)=C(R$^{nn}$))—, —(C(R$^p$)=N))—, or a single bond, wherein R$^{a1}$, R$^{a2}$, R$^b$, R$^c$, R$^d$, R$^e$, R$^f$, R$^g$, R$^m$, R$^n$, and R$^p$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, at least one pair of R$^{bb}$ and R$^{cc}$, R$^{dd}$ and R$^{ee}$, R$^{ff}$ and R$^{gg}$, or R$^{mm}$ and R$^{nn}$ is linked with each other to provide a ring structure, and n1 of —(CR$^f$R$^g$)$_{n1}$— is 1 or 2, when L is —NR$^{a1}$—, —BR$^{a2}$—, —SiR$^b$R$^c$—, —GeR$^d$R$^e$—, —(CR$^f$R$^g$)$_{n1}$—, —(C(R$^m$)=C(R$^n$))—, or —(C(R$^p$)=N))—, L is optionally linked with Ar$^1$ or Ar$^2$ to provide a ring structure, Ar$^3$ may be a substituted or unsubstituted C6 to C30 hydrocarbon cyclic group having at least one functional group selected from C=O, C=S, C=Se, and C=Te, a substituted or unsubstituted C2 to C30 heterocyclic group having at least one functional group selected from C=O, C=S, C=Se, and C=Te, or a fused ring thereof, and R$^1$ and R$^2$ may independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, a pentafluorosulfanyl group (—SF$_5$), a hydroxyl group, an amine group, a hydrazine group, a hydrazone group, a carboxyl group or a salt thereof; a sulfonic acid group or a salt thereof, a phosphoric acid group or a salt thereof, —SiR$^a$R$^b$R$^c$ (wherein R$^a$, R$^b$, and R$^c$ may independently be hydrogen or a substituted or unsubstituted C1 to C10 alkyl group), or a combination thereof.

The compound represented by Chemical Formula 1 includes an electron donor moiety including a first ring moiety including nitrogen (N) and L and an X$^1$-containing second ring moiety; and an electron acceptor moiety represented by Ar$^3$; wherein the first ring moiety including the nitrogen (N) and L and the X$^1$-containing second ring moiety are fused to each other by a third ring moiety including nitrogen (N) and X$^2$ to provide a fused ring.

In Chemical Formula 1, by fusing the first ring moiety including the nitrogen (N) and L and the X$^1$-containing second ring moiety, by the third ring moiety including nitrogen (N) and X$^2$ to provide a fused ring, stability of the molecular structure of the compound may be improved, decomposition of the compound in the deposition process may be limited and/or prevented, so that the reliability of the device may be improved. In addition, in the first ring moiety including nitrogen (N) and L, Ar$^1$ and Ar$^2$ are linked by L, so that stability of the molecular structure may be further improved.

The compound represented by Chemical Formula 1 has an electron donor moiety including a fused ring of a first ring moiety including nitrogen (N) and L of a specific structure and the X$^1$-containing second ring moiety, and thereby an absorption wavelength may be adjusted in a green wavelength range (about 500 nm to about 600 nm), and high absorption characteristics may be exhibited in the wavelength range, and an absorption coefficient may be increased.

The compound of Chemical Formula 1 may be represented by Chemical Formula 2A.

[Chemical Formula 2A]

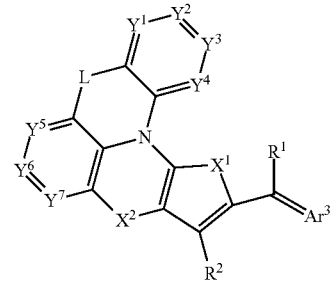

In Chemical Formula 2A,

X$^1$, X$^2$, L, Ar$^3$, R$^1$, and R$^2$ are the same as in Chemical Formula 1, and Y$^1$ to Y$^7$ may independently be N or CR$^k$, wherein R$^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent R$^k$'s are linked to each other to provide a substituted or unsubstituted C6 to C30 arene group, a substituted or unsubstituted C3 to C30 heteroarene group, or a condensed ring thereof.

In an embodiment, in Chemical Formula 2A, Y$^4$ may be N or CR$^k$, wherein R$^k$ is a halogen, a cyano group, a C1 to C10 haloalkyl group, or a C1 to C10 cyanoalkyl group. In this case, Y$^4$, N, X$^1$, and functional groups (C=O, C=S, C=Se, or C=Te) present in Ar³ increase an intramolecular interaction, thereby increasing the absorption intensity at a specific wavelength.

In an embodiment, in Chemical Formula 2A, $Y^7$ may be N or $CR^k$, wherein $R^k$ is a halogen, a cyano group, a C1 to C10 haloalkyl group, or a C1 to C10 cyanoalkyl group and $X^2$ may be —O—, —S—, —Se—, —Te—, —S(=O)—, —S(=O)$_2$—, —NR$^{a1}$—, —BR$^{a2}$—, —SiR$^b$R$^c$—, —GeR$^d$R$^e$—, —(CR$^f$R$^g$)$_{n1}$—, —(C(R$^m$)=C(R$^n$))—, or —(C(R$^p$)=N))—, wherein R$^{a1}$, R$^{a2}$, R$^b$, R$^c$, R$^d$, R$^e$, R$^f$, R$^g$, R$^m$, R$^n$, and R$^p$ may independently be a halogen, a C1 to C20 haloalkyl group, or a C1 to C20 cyanoalkyl group. In this case, $Y^7$ and $X^2$ may increase an intramolecular interaction, thereby improving the absorption intensity at a specific wavelength.

The compound represented by Chemical Formula 2A may be represented by Chemical Formula 2A-a to Chemical Formula 2A-f depending on the type of L.

[Chemical Formula 2A-a]

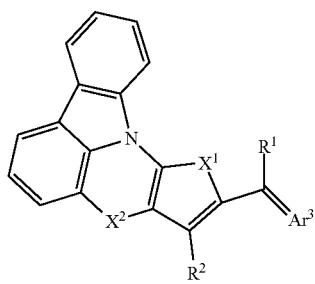

[Chemical Formula 2A-b]

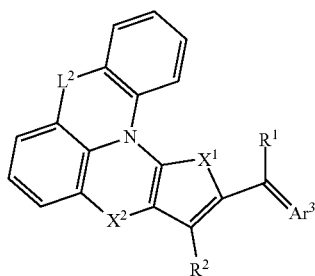

[Chemical Formula 2A-c]

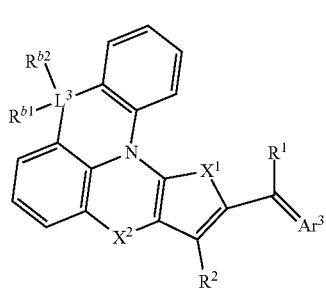

[Chemical Formula 2A-d]

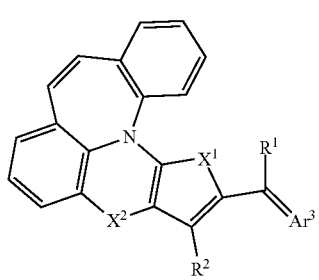

[Chemical Formula 2A-e]

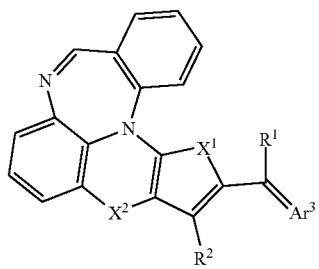

[Chemical Formula 2A-f]

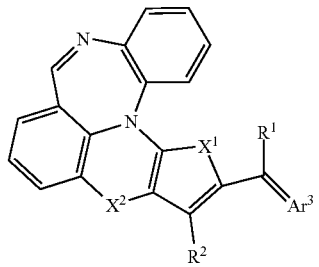

In Chemical Formula 2A-a to Chemical Formula 2A-f, $X^1$, $X^2$, Ar³, $R^1$, and $R^2$ are the same as in Chemical Formula 1, $L^2$ is —O—, —S—, —Se—, —Te—, —NR$^{a1}$—, or —BR$^{a2}$—, wherein R$^{a1}$ and R$^{a2}$ may independently be hydrogen, deuterium, a halogen, a substituted or unsubstituted C1 to C20 alkyl group, or a substituted or unsubstituted C6 to C20 aryl group, $L^3$ is Si, Ge, or C, $R^{b1}$ and $R^{b2}$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

In Chemical Formula 2A-a to Chemical Formula 2A-f, CH of a 6-membered ring structure (e.g., a benzene ring) may be replaced by N, and at least one (e.g., 1, 2 or 3) of N may be included.

In Chemical Formula 2A, at least one (CR$^k$) of $Y^1$ and $Y^5$ and L (—NR$^{a1}$—, —BR$^{a2}$—, —SiR$^b$R$^c$—, —GeR$^d$R$^e$—, —(CR$^f$R$^g$)$_n$—, —(C(R$^m$)=C(R$^n$))—, or —(C(R$^p$)=N))—) may be linked to each other to provide a fused ring. This structure may be represented by Chemical Formula 2A-1 or Chemical Formula 2A-2.

[Chemical Formula 2A-1]

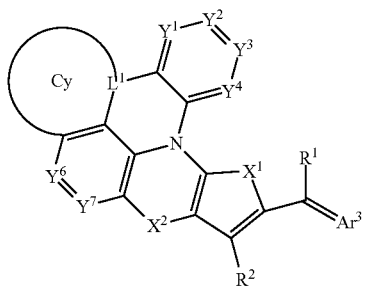

In Chemical Formula 2A-1, $X^1$, $X^2$, $Ar^3$, $R^1$, and $R^2$ are the same as in Chemical Formula 1, $L^1$ may be N, B, Si, Ge, or C, $Y^1$ to $Y^4$, $Y^6$, and $Y^7$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, and Cy may be a substituted or unsubstituted C6 to C30 arene group, for example a substituted or unsubstituted C6 to C20 arene group or a substituted or unsubstituted C6 to C10 arene group; a substituted or unsubstituted C3 to C30 heteroarene group, for example a substituted or unsubstituted C3 to C20 heteroarene group or a substituted or unsubstituted C3 to C10 heteroarene group; a substituted or unsubstituted C5 to C30 cycloalkene group, for example a substituted or unsubstituted C5 to C20 cycloalkene group or a substituted or unsubstituted C5 to C10 cycloalkene group; a substituted or unsubstituted C5 to C30 heterocycloalkene group, for example a substituted or unsubstituted C5 to C20 heterocycloalkene group or a substituted or unsubstituted C5 to C10 heterocycloalkene group; or a condensed ring thereof.

[Chemical Formula 2A-2]

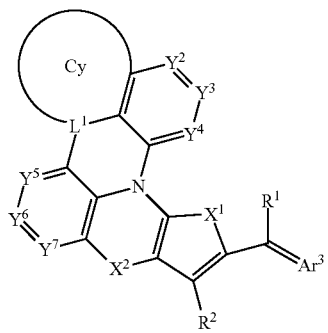

In Chemical Formula 2A-2, $X^1$, $X^2$, $Ar^3$, $R^1$, and $R^2$ are the same as in Chemical Formula 1, $L^1$ may be N, B, Si, Ge, or C, $Y^2$ to $Y^7$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, and Cy may be a substituted or unsubstituted C6 to C30 arene group, for example a substituted or unsubstituted C6 to C20 arene group or a substituted or unsubstituted C6 to C10 arene group; a substituted or unsubstituted C3 to C30 heteroarene group, for example a substituted or unsubstituted C3 to C20 heteroarene group or a substituted or unsubstituted C3 to C10 heteroarene group; a substituted or unsubstituted C5 to C30 cycloalkene group, for example a substituted or unsubstituted C5 to C20 cycloalkene group or a substituted or unsubstituted C5 to C10 cycloalkene group; a substituted or unsubstituted C5 to C30 heterocycloalkene group, for example a substituted or unsubstituted C5 to C20 heterocycloalkene group or a substituted or unsubstituted C5 to C10 heterocycloalkene group; or a condensed ring thereof.

In an embodiment, Cy of Chemical Formula 2A-1 and Chemical Formula 2A-2 may be an arene group, a heteroarene group, a cycloalkene group, or a heterocycloalkene group, and they may have a 5-member to 10-member ring structure. The heteroarene group or heterocycloalkene group may include N in the ring.

When Cy of Chemical Formula 2A-1 has a 6-membered ring structure, the compound of Chemical Formula 2A may be represented by Chemical Formula 2A-11a or Chemical Formula 2A-11b.

[Chemical Formula 2A-11a]

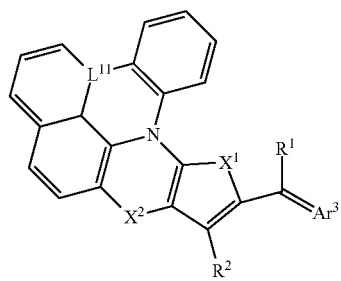

[Chemical Formula 2A-11b]

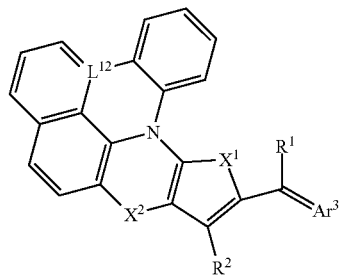

In Chemical Formula 2A-11a and Chemical Formula 2A-11b, $X^1$, $X^2$, $Ar^3$, $R^1$, and $R^2$ are the same as in Chemical Formula 1, $L^{11}$ may be B or N, $L^{12}$ may be Si, Ge, or C, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, CH of a 6-membered ring structure (for example, a benzene ring and/or a cyclohexadiene ring) in Chemical Formula 2A-11a and Chemical Formula 2A-11b may be replaced by N, and one or more (e.g., 1, 2, or 3) N may be included in one 6-member ring structure.

When Cy of Chemical Formula 2A-1 has two fused 6-membered ring structures (a hexagonal ring including $L^4$ and $L^{11}$ and a benzene ring fused thereto in Chemical Formula 2A-12), the compound of Chemical Formula 2A-1 may be represented by Chemical Formula 2A-12.

[Chemical Formula 2A-12]

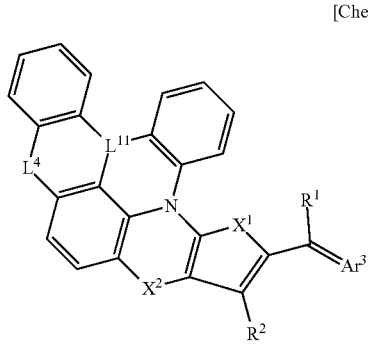

In Chemical Formula 2A-12, $X^1$, $X^2$, $Ar^3$, $R^1$, and $R^2$ are the same as in Chemical Formula 1, $L^4$ may be —O—, —S—, —Se—, —Te—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —(CR$^f$R$^g$)$_{n1}$—, —(CR$^{ff}$R$^{gg}$)—, —(C(R$^m$)=C(R$^n$))—, —(C(R$^{mm}$)=C(R$^{nn}$))—, —(C(R$^p$)=N))—, or a single bond, wherein $R^{a1}$, $R^{a2}$, $R^b$, $R^c$, $R^d$, $R^e$, $R^f$, $R^g$, $R^m$, $R^n$, and $R^p$ may independently be hydrogen, deuterium, a halogen, a substituted or unsubstituted C1 to C20 alkyl group, or a substituted or unsubstituted C6 to C20 aryl group, at least one pair of $R^{bb}$ and $R^{cc}$, $R^{dd}$ and $R^{ee}$, $R^{ff}$ and $R^{gg}$, or $R^{mm}$ and $R^{nn}$ is linked with each other to provide a ring structure, and n1 of —(CR$^f$R$^g$)$_{n1}$— is 1 or 2, $L^{11}$ may be B or N, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, in Chemical Formula 2A-12, CH of a 6-membered ring structure (e.g., a benzene ring) may be replaced by N, and at least one (e.g., 1, 2 or 3) of N may be included.

When Cy of Chemical Formula 2A-2 has a 6-membered ring structure, it may be represented by Chemical Formula 2A-21a and Chemical Formula 2A-21b.

[Chemical Formula 2A-21a]

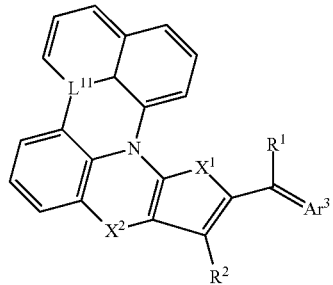

[Chemical Formula 2A-21b]

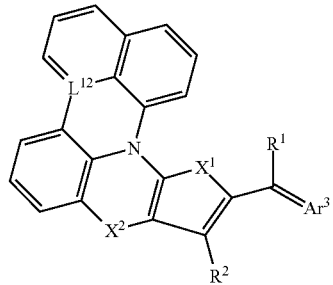

In Chemical Formula 2A-21a and Chemical Formula 2A-21b, $X^1$, $X^2$, $Ar^3$, $R^1$, and $R^2$ are the same as in Chemical Formula 1, $L^{12}$ may be Si, Ge, or C, $L^{11}$ may be B or N, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to one embodiment, CH of a 6-membered ring structure (for example, a benzene ring and/or a cyclohexadiene ring) in Chemical Formula 2A-21a and Chemical Formula 2A-21b may be replaced by N, and one or more (e.g., 1, 2, or 3) N may be included in one 6-member ring structure.

When Cy of Chemical Formula 2A-2 has two fused 6-membered ring structures (a hexagonal ring including $L^4$ and $L^{11}$ and a benzene ring fused thereto in Chemical Formula 2A-22), the compound of Chemical Formula 2A-2 may be represented by Chemical Formula 2A-22.

[Chemical Formula 2A-22]

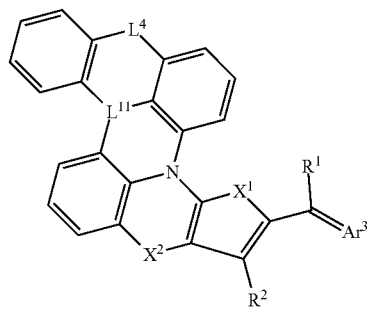

In Chemical Formula 2A-22,

X$^1$, X$^2$, Ar$^3$, R$^1$, and R$^2$ are the same as in Chemical Formula 1,

L$^4$ may be —O—, —S—, —Se—, —Te—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —(CR$^f$R$^g$)$_{n1}$—, —(CR$^{ff}$R$^{gg}$)—, —(C(R$^m$)=C(R$^n$))—, —(C(R$^{mm}$)=C(R$^{nn}$))—, —(C(R$^p$)=N))—, or a single bond, wherein R$^{a1}$, R$^{a2}$, R$^b$, R$^c$, R$^d$, R$^e$, R$^f$, R$^g$, R$^m$, R$^n$, and R$^p$ may independently be hydrogen, deuterium, a halogen, a substituted or unsubstituted C1 to C20 alkyl group, or a substituted or unsubstituted C6 to C20 aryl group, at least one pair of R$^{bb}$ and R$^{cc}$, R$^{dd}$ and R$^{ee}$, R$^{ff}$ and R$^{gg}$, or R$^{mm}$ and R$^{nn}$ is linked with each other to provide a ring structure, and n1 of —(CR$^f$R$^g$)$_{n1}$— is 1 or 2, L$^{11}$ may be B or N, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, in Chemical Formula 2A-22, CH of a 6-membered ring structure (e.g., a benzene ring) may be replaced by N, and at least one (e.g., 1, 2 or 3) of N may be included.

According to an embodiment, in Chemical Formula 2A, Y$^1$ (CR$^k$) and L (—NR$^{a1}$—, —BR$^{a2}$—, —SiR$^b$R$^c$—, —GeR$^d$R$^e$—, —(CR$^f$R$^g$)$_n$—, —(C(R$^m$)=C(R$^n$))—, or —(C(R$^p$)=N))—) may be linked to each other to provide a first fused ring and Y$^5$ (CR$^k$) and L (—NR$^{a1}$—, —BR$^{a2}$—, —SiR$^b$R$^c$—, —GeR$^d$R$^e$—, —(CR$^f$R$^g$)$_n$—, —(C(R$^m$)=C(R$^n$))—, or —(C(R$^p$)=N))—) may be linked to each other to provide a second fused ring. When the first fused ring and the second fused ring each have a 6-membered ring structure, it may be represented by Chemical Formula 2A-3a or Chemical Formula 2A-3b.

In Chemical Formula 2A-3a and Chemical Formula 2A-3b,

X$^1$, X$^2$, Ar$^3$, R$^1$, and R$^2$ are the same as in Chemical Formula 1,

L$^{11}$ may be B or N,

L$^{12}$ may be Si, Ge, or C, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, CH of a 6-membered ring structure (for example, a benzene ring and/or a cyclohexadiene ring) in Chemical Formula 2A-3a or Chemical Formula 2A-3b may be replaced by N, and one or more (e.g., 1, 2, or 3) N may be included in one 6-member ring structure.

In Chemical Formula 2A, when Y$^1$ to Y$^4$ are CR$^k$ and adjacent R$^k$'s are linked to each other to provide a fused ring (a substituted or unsubstituted C6 to C30 arene group, a substituted or unsubstituted C3 to C30 heteroarene group, a substituted or unsubstituted C5 to C30 cycloalkene group, a substituted or unsubstituted C5 to C30 cycloalkene group, or a combination thereof), it may be represented by one of Chemical Formula 2A-41 to Chemical Formula 2A-44.

[Chemical Formula 2A-3a]

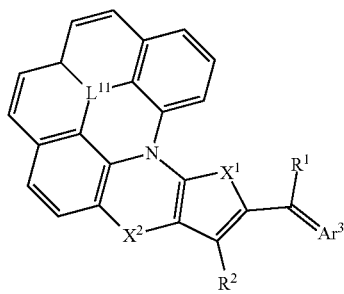

[Chemical Formula 2A-3b]

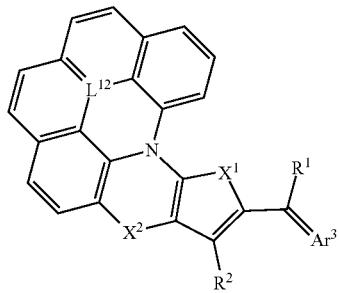

[Chemical Formula 2A-41]

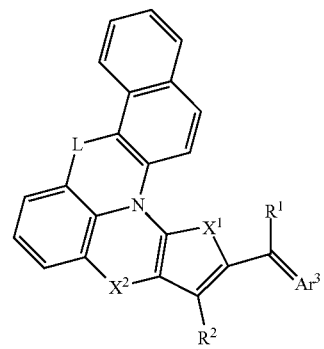

[Chemical Formula 2A-42]

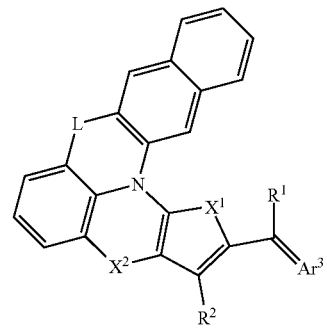

[Chemical Formula 2A-43]

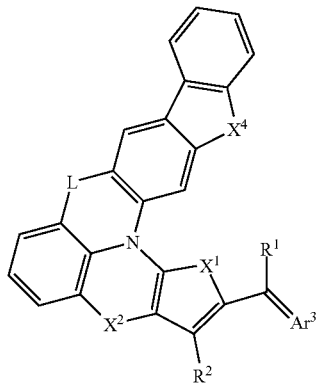

[Chemical Formula 2A-44]

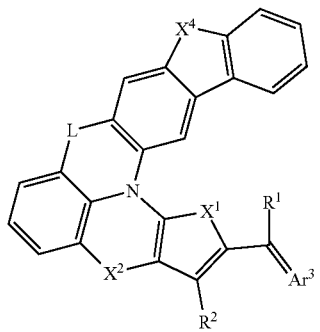

[Chemical Formula 2A-45]

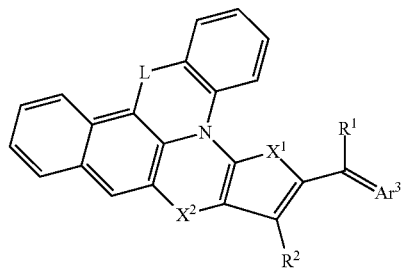

[Chemical Formula 2A-46]

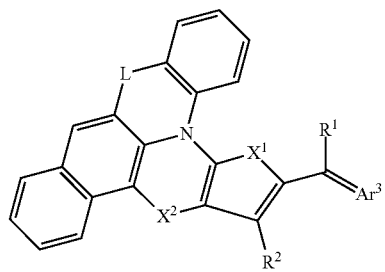

[Chemical Formula 2A-47]

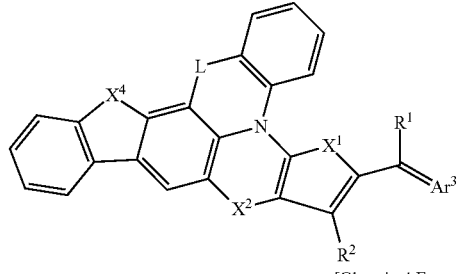

[Chemical Formula 2A-48]

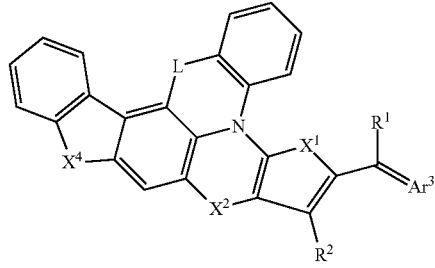

In Chemical Formula 2A-41 to Chemical Formula 2A-44, $X^1$, $X^2$, L, $Ar^3$, $R^1$, and $R^2$ are the same as in Chemical Formula 1, $X^4$ may be —O—, —S—, —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —CR$^f$R$^g$—, —CR$^{ff}$R$^{gg}$—, —CR$^h$=CR$^i$— and —CR$^{hh}$=CR$^{ii}$—, wherein R$^{a1}$, R$^{a2}$, R$^b$, R$^c$, R$^d$, R$^e$, R$^f$, R$^g$, R$^h$, R$^i$ and R$^j$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of R$^{bb}$ and R$^{cc}$, R$^{dd}$ and R$^{ee}$, R$^{ff}$ and R$^{gg}$, or R$^{hh}$ and R$^{ii}$ is linked with each other to provide a ring structure, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

In Chemical Formula 2A-41 to Chemical Formula 2A-44, CH of the aromatic ring may be replaced by N, and one or more (e.g., 1, 2, or 3) N may be included.

In Chemical Formula 2A, when $Y^5$ to $Y^7$ are CR$^k$ and adjacent R$^k$'s are linked to each other to provide a fused ring (a substituted or unsubstituted C6 to C30 arene group, a substituted or unsubstituted C3 to C30 heteroarene group, a substituted or unsubstituted C5 to C30 cycloalkane group, a substituted or unsubstituted C5 to C30 cycloalkene group, or a combination thereof), it may be represented by one of Chemical Formula 2A-45 to Chemical Formula 2A-48.

In Chemical Formula 2A-45 to Chemical Formula 2A-48, $X^1$, $X^2$, L, $Ar^3$, $R^1$, and $R^2$ are the same as in Chemical Formula 1, $X^4$ may be —O—, —S—, —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —CR$^f$R$^g$—, —CR$^{ff}$R$^{gg}$—, —CR$^h$=CR$^i$— and —CR$^{hh}$=CR$^{ii}$—, wherein R$^{a1}$, R$^{a2}$, R$^b$, R$^c$, R$^d$, R$^e$, R$^f$, R$^g$, R$^h$, R$^i$ and R$^j$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of R$^{bb}$ and R$^{cc}$, R$^{dd}$ and R$^{ee}$, R$^{ff}$ and R$^{gg}$, or R$^{hh}$ and R$^{ii}$ is linked with each other to provide a ring structure, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

In Chemical Formula 2A-45 to Chemical Formula 2A-48, CH of the aromatic ring may be replaced by N, and one or more (e.g., 1, 2, or 3) N may be included.

The compound of Chemical Formula 1 may be represented by Chemical Formula 2B.

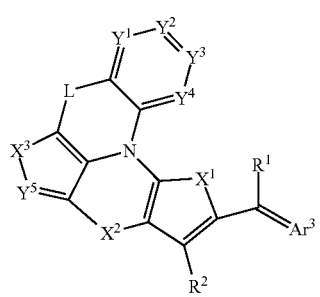

[Chemical Formula 2B]

In Chemical Formula 2B, $X^1$, $X^2$, L, $Ar^3$, $R^1$, and $R^2$ are the same as in Chemical Formula 1, $Y^1$ to $Y^5$ may independently be N or $CR^k$, wherein $R^k$ may be hydrogen, deuterium; a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, and $X^3$ may be —O—, —S—, —Se—, —Te—, —S(=O)—, —S(=O)$_2$—, —$NR^{a1}$—, —$BR^{a2}$—, —$SiR^bR^c$—, —$SiR^{bb}R^{cc}$—, —$GeR^dR^e$—, —$GeR^{dd}R^{ee}$—, —$CR^fR^g$—, or —$CR^{ff}R^{gg}$—, wherein $R^{a1}$, $R^{a2}$, $R^b$, $R^c$, $R^d$, $R^e$, $R^f$, and $R^g$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of $R^{bb}$ and $R^{cc}$, $R^{dd}$ and $R^{ee}$, or $R^{ff}$ and $R^{gg}$ is linked to each other to provide a ring structure.

In an embodiment, in Chemical Formula 2B, $Y^4$ may be N or $CR^k$, wherein $R^k$ is a halogen, a cyano group, a C1 to C10 haloalkyl group, or a C1 to C10 cyanoalkyl group. In this case, $Y^4$, N, $X^1$, and functional groups (C=O, C=S, C=Se, or C=Te) present in $Ar^3$ increase an intramolecular interaction, thereby increasing the absorption intensity at a specific wavelength.

In an embodiment, in Chemical Formula 2B, $Y^5$ is N or $CR^k$, wherein $R^k$ is a halogen, a cyano group, a C1 to C10 haloalkyl group, or a C1 to C10 cyanoalkyl group and $X^2$ is —O—, —S—, —Se—, —Te—, —S(=O)—, —S(=O)$_2$—, —$NR^{a1}$—, —$BR^{a2}$—, —$SiR^bR^c$—, —$GeR^dR^e$—, —$(CR^fR^g)_{n1}$—, —$(C(R^m)=C(R^n))$—, or —$(C(R^p)=N)$—, wherein $R^{a1}$, $R^{a2}$, $R^b$, $R^c$, $R^d$, $R^e$, $R^f$, $R^g$, $R^m$, $R^n$, and $R^p$ may independently be a halogen, a C1 to C20 haloalkyl group, or a C1 to C20 cyanoalkyl group. In this case, $Y^5$ and $X^2$ may increase an intramolecular interaction, thereby improving the absorption intensity at a specific wavelength.

The compound represented by Chemical Formula 2B may be represented by Chemical Formula 2B-a to Chemical Formula 2B-f depending on the type of L.

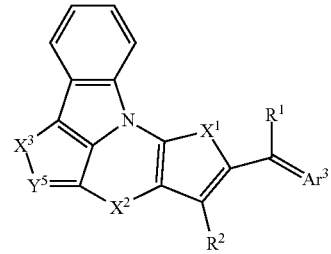

[Chemical Formula 2B-a]

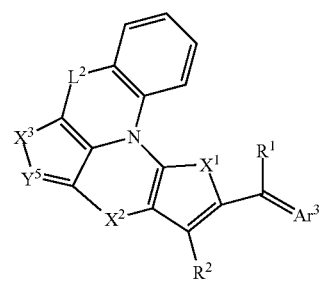

[Chemical Formula 2B-b]

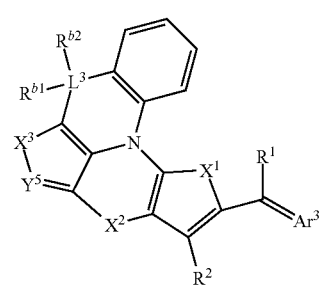

[Chemical Formula 2B-c]

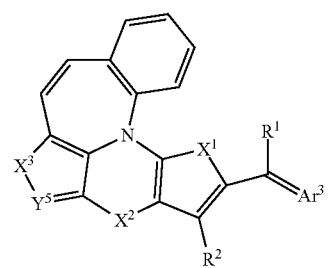

[Chemical Formula 2B-d]

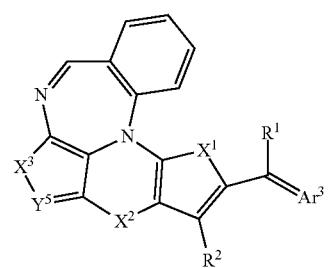

[Chemical Formula 2B-e]

[Chemical Formula 2B-f]

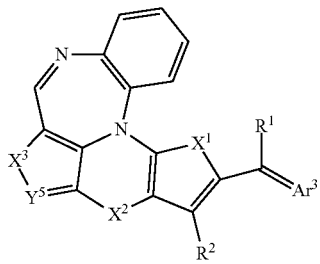

In Chemical Formula 2B-a to Chemical Formula 2B-f,
$X^1$, $X^2$, $Ar^3$, $R^1$, and $R^2$ are the same as in Chemical Formula 1,
$Y^5$ and $X^3$ are the same as in Chemical Formula 2B, $L^2$ may be —O—, —S—, —Se—, —Te—, —$NR^{a1}$—, or —$BR^{a2}$—, wherein $R^{a1}$ and $R^{a2}$ may independently be hydrogen, deuterium, a halogen, a substituted or unsubstituted C1 to C20 alkyl group, or a substituted or unsubstituted C6 to C20 aryl group,
$L^3$ may be Si, Ge, or C,
$R^{b1}$ and $R^{b2}$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and
hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

In Chemical Formula 2B-a to Chemical Formula 2B-f, CH of a 6-membered ring structure (e.g., a benzene ring) may be replaced by N, and at least one (e.g., 1, 2 or 3) of N may be included.

In Chemical Formula 2B, L (—$NR^{a1}$—, —$BR^{a2}$—, —$SiR^bR^c$—, —$GeR^dR^e$—, —$(CR^fR^g)_n$—, —$(C(R^m)=C(R^n))$—, or —$(C(R^p)=N))$—) and $X^3$ (—$NR^{a1}$—, —$BR^{a2}$—, —$SiR^bR^c$—, —$GeR^dR^e$— or —$CR^fR^g$—) may be linked to each other to provide a fused ring. This structure may be represented by Chemical Formula 2B-1.

[Chemical Formula 2B-1]

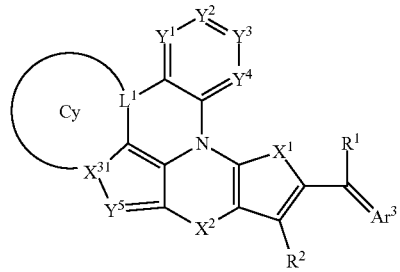

In Chemical Formula 2B-1,
$X^1$, $X^2$, $Ar^3$, $R^1$, and $R^2$ are the same as in Chemical Formula 1,
$L^1$ may be N, B, Si, Ge, or C,
$X^{31}$ may be N, $SiR^b$, $GeR^d$, $CR^f$, Si, Ge, or C, wherein $R^b$, $R^d$, and $R^f$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group,
$Y^1$ to $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, and
Cy may be a substituted or unsubstituted C6 to C30 arene group, for example a substituted or unsubstituted C6 to C20 arene group or a substituted or unsubstituted C6 to C10 arene group; a substituted or unsubstituted C3 to C30 heteroarene group, for example a substituted or unsubstituted C3 to C20 heteroarene group or a substituted or unsubstituted C3 to C10 heteroarene group; a substituted or unsubstituted C5 to C30 cycloalkene group, for example a substituted or unsubstituted C5 to C20 cycloalkene group or a substituted or unsubstituted C5 to C10 cycloalkene group; a substituted or unsubstituted C5 to C30 heterocycloalkene group, for example a substituted or unsubstituted C5 to C20 heterocycloalkene group or a substituted or unsubstituted C5 to C10 heterocycloalkene group; or a condensed ring thereof.

In Chemical Formula 2B, L (—$NR^{a1}$—, —$BR^{a2}$—, —$SiR^bR^c$—, —$GeR^dR^e$—, —$(CR^fR^g)_n$—, —$(C(R^m)=C(R^n))$—, or —$(C(R^p)=N))$—) and $Y^1$ ($CR^k$) may be linked to each other to provide a fused ring. This structure may be represented by Chemical Formula 2B-2.

[Chemical Formula 2B-2]

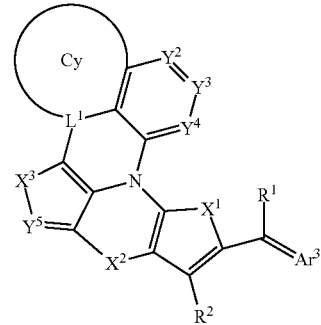

In Chemical Formula 2B-2,
$X^1$, $X^2$, $Ar^3$, $R^1$, and $R^2$ are the same as in Chemical Formula 1,
$X^3$ is the same as in Chemical Formula 2B,
$L^1$ may be N, B, Si, Ge, or C,
$Y^2$ to $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, and Cy may be a substituted or unsubstituted C6 to C30 arene group, for example a substituted or unsubstituted C6 to C20 arene group or a substituted or unsubstituted C6 to C10 arene group; a substituted or unsubstituted C3 to C30 heteroarene group, for example a substituted or unsubstituted C3 to C20 heteroarene group or a substituted or unsubstituted C3 to C10 heteroarene group; a substituted or unsubstituted C5 to C30 cycloalkene group, for example a substituted or unsubstituted C5 to C20 cycloalkene group or a substituted or unsubstituted C5 to C10 cycloalkene group; a substituted or unsubstituted C5 to C30 heterocycloalkene group, for example a substituted or unsubstituted C5 to C20 heterocycloalkene group or a substituted or unsubstituted C5 to C10 heterocycloalkene group; or a condensed ring thereof.

In an embodiment, Cy of Chemical Formulas 2B-1 and 2B-2 may be an arene group, a heteroarene group, a cycloalkene group, or a heterocycloalkene group, and they may have a 5-membered to 10-membered ring structure. The heteroarene group or heterocycloalkene group may include N in the ring.

When Cy of Chemical Formula 2B-1 has a 6-membered ring structure, the compound of Chemical Formula 2B may be represented by Chemical Formula 2B-11a or Chemical Formula 2B-11b.

[Chemical Formula 2B-11a]

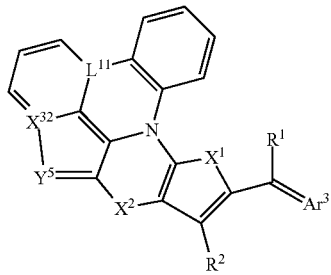

[Chemical Formula 2B-11b]

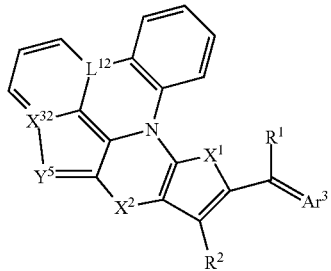

In Chemical Formula 2B-11a and Chemical Formula 2B-11b, $X^1$, $X^2$, $Ar^3$, $R^1$, and $R^2$ are the same as in Chemical Formula 1, $Y^5$ are the same as in Chemical Formula 2B, $L^{11}$ may be B or N, $L^{12}$ may be Si, Ge, or C, $X^{32}$ may be Si, Ge, or C, $X^{33}$ may be N, $SiR^b$, $GeR^d$, or $CR^f$, wherein $R^b$, $R^d$, and $R^f$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to one embodiment, CH of a 6-membered ring structure (for example, a benzene ring and/or a cyclohexadiene ring) in Chemical Formula 2B-11a and Chemical Formula 2B-11b may be replaced by N, and one or more (e.g., 1, 2, or 3) N may be included in one 6-member ring structure.

When Cy of Chemical Formula 2B-1 has two fused 6-membered ring structures (a hexagonal ring including $L^4$ and $L^{11}$ and a benzene ring fused thereto in Chemical Formula 2B-12), the compound of Chemical Formula 2B-1 may be represented by Chemical Formula 2B-12.

[Chemical Formula 2B-12]

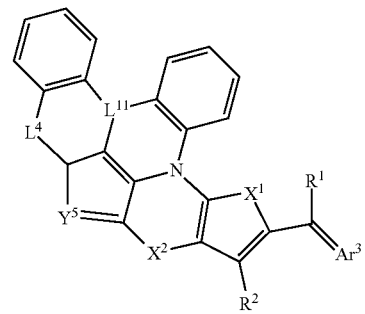

In Chemical Formula 2B-12, $X^1$, $X^2$, $Ar^3$, $R^1$, and $R^2$ are the same as in Chemical Formula 1, $Y^5$ are the same as in Chemical Formula 2B, $L^4$ may be —O—, —S—, —Se—, —Te—, —$NR^{a1}$—, —$BR^{a2}$—, —$SiR^bR^c$—, —$SiR^{bb}R^{cc}$—, —$GeR^dR^e$—, —$GeR^{dd}R^{ee}$—, —$(CR^fR^g)_{n1}$—, —$(CR^{ff}R^{gg})$—, —$(C(R^m)=C(R^n))$—, —$(C(R^{mm})=C(R^{nn}))$—, —$(C(R^p)=N))$—, or a single bond, wherein $R^{a1}$, $R^{a2}$, $R^b$, $R^c$, $R^d$, $R^e$, $R^f$, $R^g$, $R^m$, $R^n$, and $R^p$ may independently be hydrogen, deuterium, a halogen, a substituted or unsubstituted C1 to C20 alkyl group and a substituted or unsubstituted C6 to C20 aryl group, at least one pair of $R^{bb}$ and $R^{cc}$, $R^{dd}$ and $R^{ee}$, $R^{ff}$ and $R^{gg}$, or $R^{mm}$ and $R^{nn}$ is linked with each other to provide a ring structure, and n1 of —$(CR^fR^g)_{n1}$— is 1 or 2, $L^{11}$ may be B or N, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, in Chemical Formula 2B-12, CH of a 6-membered ring structure (e.g., a benzene ring) may be replaced by N, and at least one (e.g., 1, 2 or 3) of N may be included.

When Cy of Chemical Formula 2B-2 has a 6-membered ring structure, it may be represented by Chemical Formula 2B-21a or Chemical Formula 2B-21b.

[Chemical Formula 2B-21a]

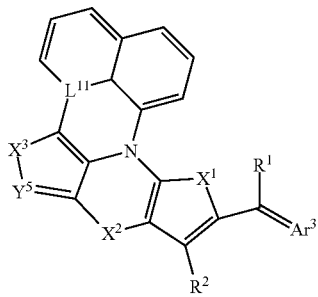

[Chemical Formula 2B-21b]

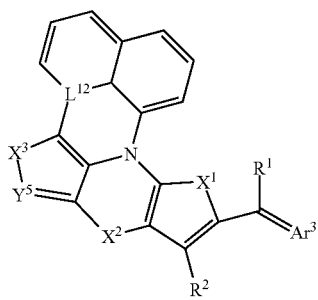

In Chemical Formula 2B-21a and Chemical Formula 2B-21b, $X^1$, $X^2$, $Ar^3$, $R^1$, and $R^2$ are the same as in Chemical Formula 1, $X^3$ and $Y^5$ are the same as in Chemical Formula 2B, $L^{11}$ may be B or N, $L^{12}$ may be Si, Ge, or C, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, CH of a 6-membered ring structure (for example, a benzene ring and/or a cyclohexadiene ring) in Chemical Formula 2B-21a and Chemical Formula 2B-21b may be replaced by N, and one or more (e.g., 1, 2, or 3) N may be included in one 6-member ring structure.

When Cy of Chemical Formula 2B-2 has two fused 6-membered ring structures (a hexagonal ring including $L^4$ and $L^{11}$ and a benzene ring fused thereto in Chemical Formula 2B-22), the compound of Chemical Formula 2B-2 may be represented by Chemical Formula 2B-22.

[Chemical Formula 2B-22]

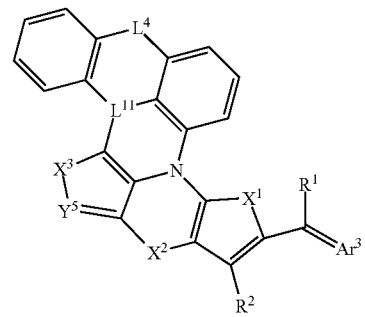

In Chemical Formula 2B-22, $X^1$, $X^2$, $Ar^3$, $R^1$, and $R^2$ are the same as in Chemical Formula 1, $X^3$ and $Y^5$ are the same as in Chemical Formula 2B, $L^4$ may be —O—, —S—, —Se—, —Te—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —(CR$^f$R$^g$)$_{n1}$—, —(CR$^{ff}$R$^{gg}$)—, —(C(R$^m$)=C(R$^n$))—, —(C(R$^{mm}$)=C(R$^{nn}$)—, —(C(R$^p$)=N))—, or a single bond, wherein R$^{a1}$, R$^{a2}$, R$^b$, R$^c$, R$^d$, R$^e$, R$^f$, R$^g$, R$^m$, R$^n$, and R$^p$ may independently be hydrogen, deuterium, a halogen, a substituted or unsubstituted C1 to C20 alkyl group, or a substituted or unsubstituted C6 to C20 aryl group, at least one pair of R$^{bb}$ and R$^{cc}$, R$^{dd}$ and R$^{ee}$, R$^{ff}$ and R$^{gg}$, or R$^{mm}$ and R$^{nn}$ is linked with each other to provide a ring structure, and n1 of —(CR$^f$R$^g$)$_{n1}$— is 1 or 2, $L^{11}$ may be B or N, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, CH of a 6-membered ring structure (for example, a benzene ring and/or a cyclohexadiene ring) in Chemical Formula 2B-22 may be replaced by N, and one or more (e.g., 1, 2, or 3) N may be included in one 6-member ring structure.

According to an embodiment, in Chemical Formula 2B, $Y^1$ (CR$^k$) and L (—NR$^{a1}$—, —BR$^{a2}$—, —SiR$^b$R$^c$—, —GeR$^d$R$^e$—, —(CR$^f$R$^g$)$_n$—, —(C(R$^m$)=C(R$^n$))— or —(C(R$^p$)=N))—) may be linked to each other to provide a first fused ring and $X^3$ (—NR$^{a1}$—, —BR$^{a2}$—, —SiR$^b$R$^c$—, —GeR$^d$R$^e$— or —CR$^f$R$^g$— and L (—NR$^{a1}$—, —BR$^{a2}$—, —SiR$^b$R$^c$—, —GeR$^d$R$^e$—, —(CR$^f$R$^g$)$_n$—, —(C(R$^m$)=C(R$^n$))—, or —(C(R$^p$)=N))—) may be linked to each other to provide a second fused ring. When the first fused ring and the second fused ring each have a 6-membered ring structure, it may be represented by Chemical Formula 2B-3a or Chemical Formula 2B-3b.

[Chemical Formula 2B-3a]

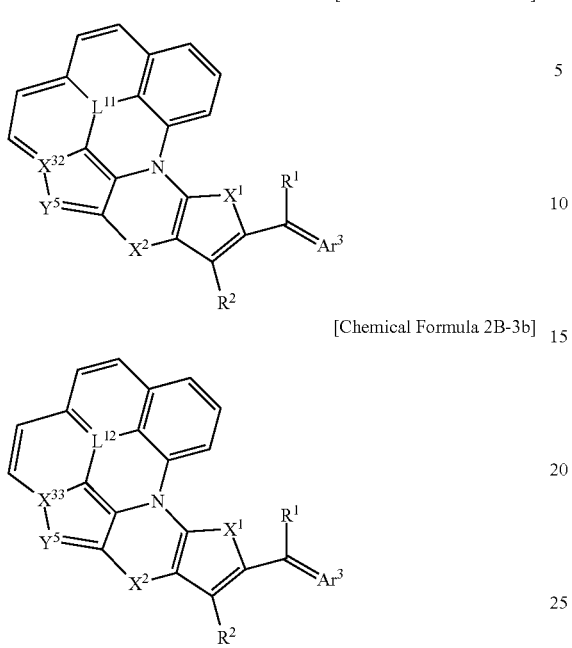

[Chemical Formula 2B-3b]

[Chemical Formula 2B-41]

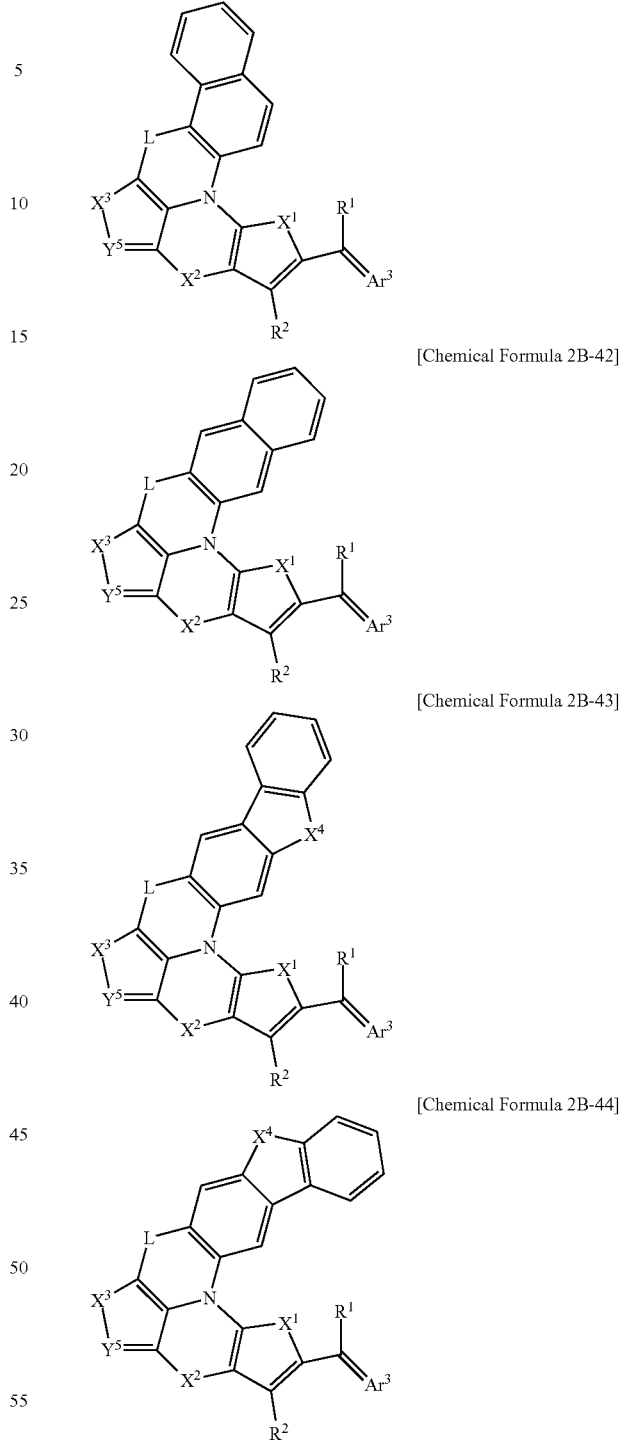

[Chemical Formula 2B-42]

[Chemical Formula 2B-43]

[Chemical Formula 2B-44]

In Chemical Formula 2B-3a and Chemical Formula 2B-3b, $X^1$, $X^2$, $Ar^3$, $R^1$, and $R^2$ are the same as in Chemical Formula 1, $Y^5$ are the same as in Chemical Formula 2B, $L^{11}$ may be B or N, $L^{12}$ may be Si, Ge, or C, $X^{32}$ may be Si, Ge, or C, $X^{33}$ may be N, $SiR^b$, $GeR^d$, or $CR^f$, wherein $R^b$, $R^d$, and $R^f$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, CH of a 6-membered ring structure (for example, a benzene ring and/or a cyclohexadiene ring) in Chemical Formula 2B-3a and Chemical Formula 2B-3b may be replaced by N, and one or more (e.g., 1, 2, or 3) N may be included in one 6-member ring structure.

In Chemical Formula 2B, when $Y^1$ to $Y^4$ are $CR^k$ and adjacent $R^k$'s are linked to each other to provide a fused ring (a substituted or unsubstituted C6 to C30 arene group, a substituted or unsubstituted C3 to C30 heteroarene group, a substituted or unsubstituted C5 to C30 cycloalkene group, a substituted or unsubstituted C5 to C30 cycloalkene group, or a combination thereof), it may be represented by one of Chemical Formula 2B-41 to Chemical Formula 2B-44.

In Chemical Formula 2B-41 to Chemical Formula 2B-44, $X^1$, $X^2$, L, $Ar^3$, $R^1$, and $R^2$ are the same as in Chemical Formula 1, $X^3$ and $Y^5$ are the same as in Chemical Formula 2B, $X^4$ may be —O—, —S—, —Se—, —Te—, —S(=O)—, —S(=O)$_2$—, —$NR^{a1}$—, —$BR^{a2}$—, —$SiR^bR^c$—, —$SiR^{bb}R^{cc}$—, —$GeR^dR^e$—, —$GeR^{dd}R^{ee}$—, —$CR^fR^g$—, —$CR^{ff}R^{gg}$—, —$CR^h$=$CR^i$—, or —$CR^{hh}$=$CR^{ii}$—, wherein $R^{a1}$, $R^{a2}$, $R^b$, $R^c$, $R^d$, $R^e$, $R^f$, $R^g$, $R^h$, $R^i$, and $R^j$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of $R^{bb}$ and $R^{cc}$, $R^{dd}$ and $R^{ee}$, $R^{ff}$ and $R^{gg}$, or $R^{hh}$ and $R^{ii}$ is linked with each other to provide a ring structure, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, in Chemical Formula 2B-41 to Chemical Formula 2B-44, CH of the aromatic ring may be replaced by N, and one or more (e.g., 1, 2, or 3) N may be included.

In addition, in Chemical Formula 2B, when $X^3$ and $Y^5$ are linked to each other to provide a fused ring (a substituted or unsubstituted C6 to C30 arene group, a substituted or unsubstituted C3 to C30 heteroarene group, a substituted or unsubstituted C5 to C30 cycloalkene group, a substituted or unsubstituted C5 to C30 cycloalkene group, or a combination thereof), it may be represented by one of Chemical Formula 2B-45 to Chemical Formula 2B-50.

[Chemical Formula 2B-45]

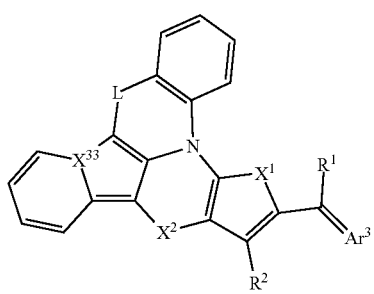

[Chemical Formula 2B-46]

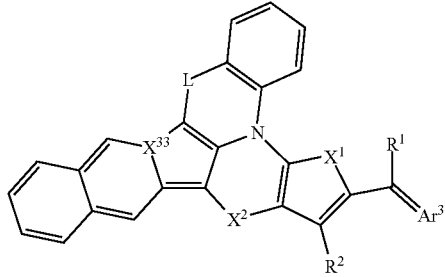

[Chemical Formula 2B-47]

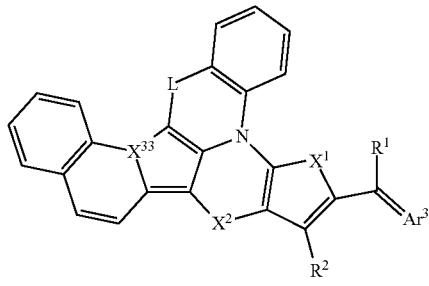

[Chemical Formula 2B-48]

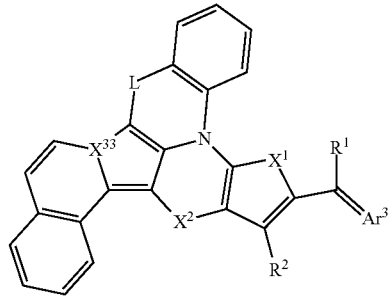

[Chemical Formula 2B-49]

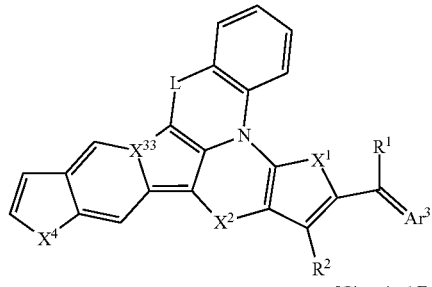

[Chemical Formula 2B-50]

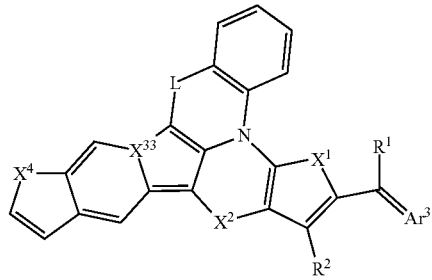

In Chemical Formula 2B-45 to Chemical Formula 2B-50, $X^1$, $X^2$, L, $Ar^3$, $R^1$, and $R^2$ are the same as in Chemical Formula 1, $X^{33}$ may be N, $SiR^b$, $GeR^d$, or $CR^f$, wherein $R^b$, $R^d$, and $R^f$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, $X^4$ may be —O—, —S—, —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —CR$^f$R$^g$—, —CR$^{ff}$R$^{gg}$—, —CR$^h$=CR$^i$—, or —CR$^{hh}$=CR$^{ii}$—, wherein $R^{a1}$, $R^{a2}$, $R^b$, $R^c$, $R^d$, $R^e$, $R^f$, $R^g$, $R^h$, $R^i$, and $R^j$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of $R^{bb}$ and $R^{cc}$, $R^{dd}$ and $R^{ee}$, $R^{ff}$ and $R^{gg}$, or $R^{hh}$ and $R^{ii}$ is linked with each other to provide a ring structure, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, CH of the aromatic ring in Chemical Formula 2B-45 to Chemical Formula 2B-50 may be replaced by N, and one or more (e.g., 1, 2, or 3) N may be included.

The compound of Chemical Formula 1 may be represented by Chemical Formula 2C.

[Chemical Formula 2C]

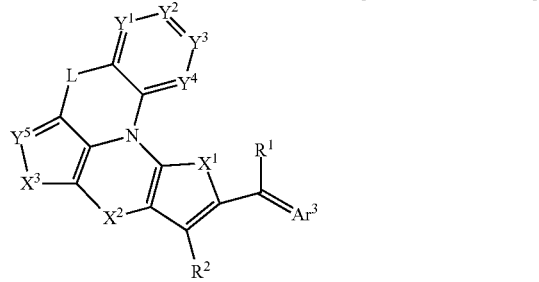

In Chemical Formula 2C, $X^1$, $X^2$, L, $Ar^3$, $R^1$, and $R^2$ are the same as in Chemical Formula 1, $Y^1$ to $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, and $X^3$ may be —O—, —S—, —Se—, —Te—, —S(=O)—, —S(=O)$_2$—, —$NR^{a1}$—, —$BR^{a2}$—, —$SiR^bR^c$—, —$SiR^{bb}R^{cc}$—, —$GeR^dR^e$—, —$GeR^{dd}R^{ee}$—, —$CR^fR^g$—, or —$CR^{ff}R^{gg}$—, wherein $R^{a1}$, $R^{a2}$, $R^b$, $R^c$, $R^d$, $R^e$, $R^f$, and $R^g$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of $R^{bb}$ and $R^{cc}$, $R^{dd}$ and $R^{ee}$, or $R^{ff}$ and $R^{gg}$ is linked to each other to provide a ring structure.

In an embodiment, in Chemical Formula 20, $Y^4$ may be N or $CR^k$, wherein $R^k$ is a halogen, a cyano group, a C1 to C10 haloalkyl group, or a C1 to C10 cyanoalkyl group. In this case, $Y^4$, N, $X^1$, and functional groups (C=O, C=S, C=Se, or C=Te) present in $Ar^3$ increase an intramolecular interaction, thereby increasing the absorption intensity at a specific wavelength.

In an embodiment, in Chemical Formula 2C, $X^3$ may be —O—, —S—, —Se—, —Te—, —S(=O)—, —S(=O)$_2$—, —$NR^{a1}$—, —$BR^{a2}$—, —$SiR^bR^c$—, —$GeR^dR^e$—, or —$CR^fR^g$—, wherein $R^{a1}$, $R^{a2}$, $R^b$, $R^c$, $R^d$, $R^e$, $R^f$, and $R^g$ may independently be a halogen, a C1 to C20 haloalkyl group, or a C1 to C20 cyanoalkyl group and $X^2$ may be —O—, —S—, —Se—, —Te—, —S(=O)—, —S(=O)$_2$—, —$NR^{a1}$—, —$BR^{a2}$—, —$SiR^bR^c$—, —$GeR^dR^e$—, —$(CR^fR^g)_{n1}$—, —$(C(R^m)=C(R^n))$—, or —$(C(R^p)=N)$—, wherein $R^{a1}$, $R^{a2}$, $R^b$, $R^c$, $R^d$, $R^e$, $R^f$, $R^g$, $R^m$, $R^n$, and $R^p$ may independently be a halogen, a C1 to C20 haloalkyl group, or a C1 to C20 cyanoalkyl group. In this case, $X^3$ and $X^2$ may increase an intramolecular interaction, thereby improving the absorption intensity at a specific wavelength.

The compound represented by Chemical Formula 2C may be represented by Chemical Formula 2C-a to Chemical Formula 2C-f depending on the type of L.

[Chemical Formula 2C-a]

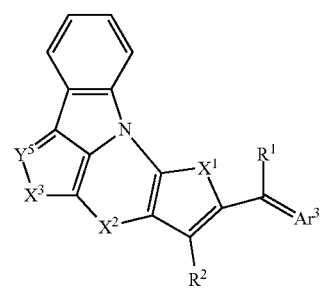

[Chemical Formula 2C-b]

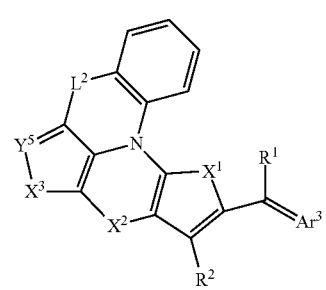

[Chemical Formula 2C-c]

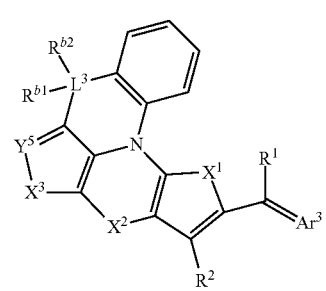

[Chemical Formula 2C-d]

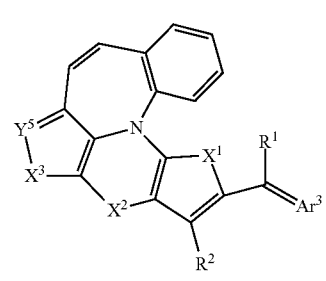

[Chemical Formula 2C-e]

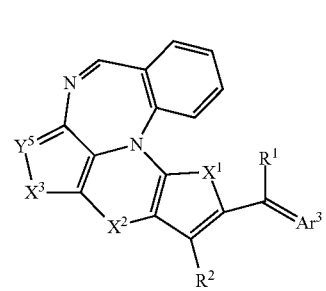

[Chemical Formula 2C-f]

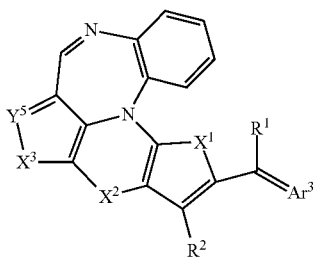

In Chemical Formula 2C-a to Chemical Formula 2C-f,
$X^1$, $X^2$, $Ar^3$, $R^1$, and $R^2$ are the same as in Chemical Formula 1,
$Y^5$ and $X^3$ are the same as in Chemical Formula 2C,
$L^2$ may be —O—, —S—, —Se—, —Te—, —$NR^{a1}$—, or —$BR^{a2}$—, wherein $R^{a1}$ and $R^{a2}$ may independently be hydrogen, deuterium, a halogen, a substituted or unsubstituted C1 to C20 alkyl group, or a substituted or unsubstituted C6 to C20 aryl group,
$L^3$ may be C, Si, or Ge,
$R^{b1}$ and $R^{b2}$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

In Chemical Formula 2C-a to Chemical Formula 2C-f, CH of the aromatic ring may be replaced by N, and one or more (e.g., 1, 2, or 3) N may be included.

In Chemical Formula 2C, L (—$NR^{a1}$—, —$BR^{a2}$—, —$SiR^bR^c$—, —$GeR^dR^e$—, —$(CR^fR^g)_n$—, —$(C(R^m)=C(R^n))$—, or —$(C(R^p)=N))$—) and $Y^5$ ($CR^k$) may be linked to each other to provide a fused ring. This structure may be represented by Chemical Formula 2C-1.

[Chemical Formula 2C-1]

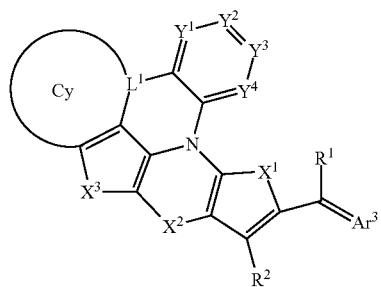

In Chemical Formula 2C-1,
$X^1$, $X^2$, $Ar^3$, $R^1$, and $R^2$ are the same as in Chemical Formula 1,
$X^3$ is the same as in Chemical Formula 2C,
$L^1$ may be N, B, Si, Ge, or C,
$Y^1$ to $Y^4$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, and Cy may be a substituted or unsubstituted C6 to C30 arene group, for example a substituted or unsubstituted C6 to C20 arene group or a substituted or unsubstituted C6 to C10 arene group; a substituted or unsubstituted C3 to C30 heteroarene group, for example a substituted or unsubstituted C3 to C20 heteroarene group or a substituted or unsubstituted C3 to C10 heteroarene group; a substituted or unsubstituted C5 to C30 cycloalkene group, for example a substituted or unsubstituted C5 to C20 cycloalkene group or a substituted or unsubstituted C5 to C10 cycloalkene group; a substituted or unsubstituted C5 to C30 heterocycloalkene group, for example a substituted or unsubstituted C5 to C20 heterocycloalkene group or a substituted or unsubstituted C5 to C10 heterocycloalkene group; or a condensed ring thereof.

In Chemical Formula 2C, L (—$NR^{a1}$—, —$BR^{a2}$—, —$SiR^bR^c$—, —$GeR^dR^e$—, —$(CR^fR^g)_n$—, —$(C(R^m)=C(R^n))$—, or —$(C(R^p)=N))$—) and $Y^1$ ($CR^k$) may be linked to each other to provide a fused ring. This structure may be represented by Chemical Formula 2C-2.

[Chemical Formula 2C-2]

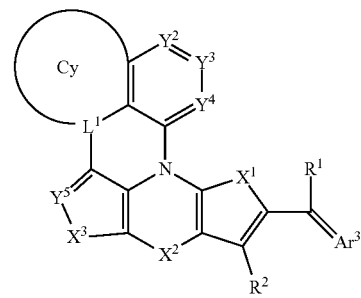

In Chemical Formula 2C-2,
$X^1$, $X^2$, $Ar^3$, $R^1$, and $R^2$ are the same as in Chemical Formula 1,
$X^3$ and $Y^5$ are the same as in Chemical Formula 2C,
$L^1$ may be N, B, Si, Ge, or C,
$Y^2$ to $Y^4$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group; a substituted or unsubstituted C5 to C30 cycloalkene group, for example a substituted or unsubstituted C5 to C20 cycloalkene group or a substituted or unsubstituted C5 to C10 cycloalkene group; a substituted or unsubstituted C5 to C30 heterocycloalkene group, for example a substituted or unsubstituted C5 to C20 heterocycloalkene group or a substituted or unsubstituted C5 to C10 heterocycloalkene group; or a condensed ring thereof, and Cy may be a substituted or unsubstituted C6 to C30 arene group, for example a substituted or unsubstituted C6 to C20 arene group or a substituted or unsubstituted C6 to C10 arene group; a substituted or unsubstituted C3 to C30 heteroarene group, for example a substituted or unsubstituted C3 to C20 heteroarene group or a substituted or unsubstituted C3 to C10 heteroarene group; or a condensed ring thereof.

In an embodiment, Cy of Chemical Formulas 2C-1 and 2C-2 may be an arene group, a heteroarene group, a cycloalkene group, or a heterocycloalkene group, and they may have a 5-membered to 10-membered ring structure. The heteroarene group or heterocycloalkene group may include N in the ring.

When Cy of Chemical Formula 2C-1 has a 6-membered ring structure, the compound represented by Chemical Formula 2C may be represented by Chemical Formula 2C-11a or Chemical Formula 2C-11b.

[Chemical Formula 2C-11a]

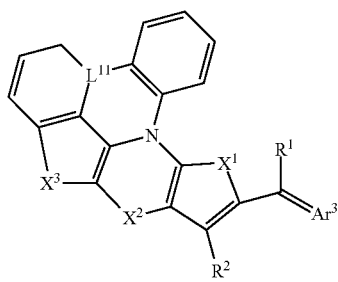

[Chemical Formula 2C-11b]

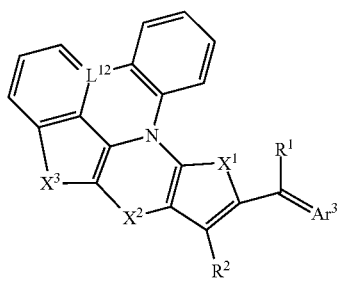

In Chemical Formula 2C-11a and Chemical Formula 2C-11b, $X^1$, $X^2$, $Ar^3$, $R^1$, and $R^2$ are the same as in Chemical Formula 1, $X^3$ is the same as in Chemical Formula 2C, $L^{11}$ is B or N, $L^{12}$ is Si, Ge, or C, hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, CH of a 6-membered ring structure (for example, a benzene ring and/or a cyclohexadiene ring) in Chemical Formula 2C-11a and Chemical Formula 2C-11b may be replaced by N, and one or more (e.g., 1, 2, or 3) N may be included in one 6-member ring structure.

When Cy of Chemical Formula 2C-1 has two fused 6-membered ring structures (a hexagonal ring including $L^4$ and $L^{11}$ and a benzene ring fused thereto in Chemical Formula 2C-12), the compound of Chemical Formula 2C-1 may be represented by Chemical Formula 2C-12.

[Chemical Formula 2C-12]

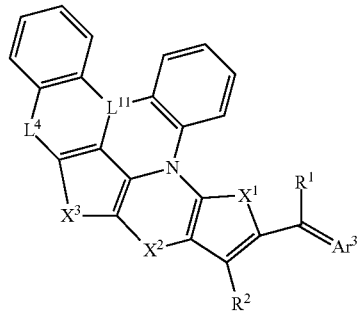

In Chemical Formula 2C-12, $X^1$, $X^2$, $Ar^3$, $R^1$, and $R^2$ are the same as in Chemical Formula 1, $X^3$ are the same as in Chemical Formula 2C, $L^4$ may be —O—, —S—, —Se—, —Te—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —(CR$^f$R$^g$)$_{n1}$—, —(CR$^{ff}$R$^{gg}$)—, —(C(R$^m$)=C(R$^n$))—, —(C(R$^{mm}$)=C(R$^{nn}$))—, —(C(R$^p$)=N))—, or a single bond, wherein R$^{a1}$, R$^{a2}$, R$^b$, R$^c$, R$^d$, R$^e$, R$^f$, R$^g$, R$^m$, R$^n$, and R$^p$ may independently be hydrogen, deuterium, a halogen, a substituted or unsubstituted C1 to C20 alkyl group, or a substituted or unsubstituted C6 to C20 aryl group, at least one pair of R$^{bb}$ and R$^{cc}$, R$^{dd}$ and R$^{ee}$, R$^{ff}$ and R$^{gg}$, or R$^{mm}$ and R$^{nn}$ is linked with each other to provide a ring structure, and n1 of —(CR$^f$R$^g$)$_{n1}$— is 1 or 2, $L^{11}$ may be B or N, hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, in Chemical Formula 2C-12, CH of a 6-membered ring structure (e.g., a benzene ring) may be replaced by N, and at least one (e.g., 1, 2 or 3) of N may be included.

When Cy of Chemical Formula 20-2 has a 6-membered ring structure, the compound of Chemical Formula 2C-2 may be represented by Chemical Formula 2C-21a or Chemical Formula 2C-21b.

[Chemical Formula 2C-21a]

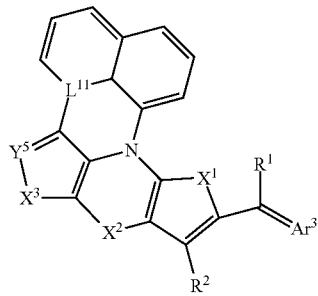

-continued

[Chemical Formula 2C-21b]

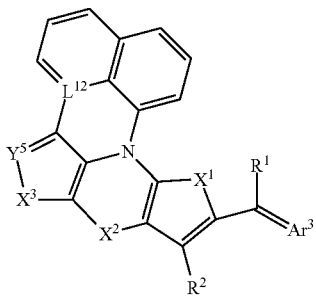

In Chemical Formula 2C-21a and Chemical Formula 2C-21b,
$X^1$, $X^2$, $Ar^3$, $R^1$, and $R^2$ are the same as in Chemical Formula 1,
$X^3$ and $Y^5$ are the same as in Chemical Formula 2C,
$L^{11}$ may be B or N,
$L^{12}$ may be Si, Ge, or C, and
hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, CH of a 6-membered ring structure (for example, a benzene ring and/or a cyclohexadiene ring) in Chemical Formula 20-21a and Chemical Formula 2C-21b may be replaced by N, and one or more (e.g., 1, 2, or 3) N may be included in one 6-member ring structure.

When Cy of Chemical Formula 2C-2 has two fused 6-membered ring structures (a hexagonal ring including $L^4$ and $L^{11}$ and a benzene ring fused thereto in Chemical Formula 2C-22), the compound of Chemical Formula 20-2 may be represented by Chemical Formula 2C-22.

[Chemical Formula 2C-22]

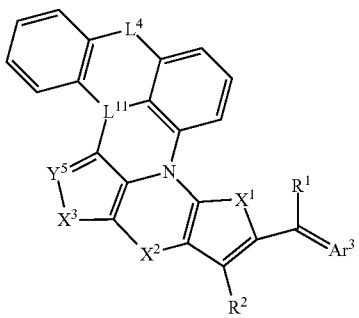

In Chemical Formula 2C-22,
$X^1$, $X^2$, $Ar^3$, $R^1$, and $R^2$ are the same as in Chemical Formula 1,
$X^3$ and $Y^5$ are the same as in Chemical Formula 2C,
$L^4$ may be —O—, —S—, —Se—, —Te—, —$NR^{a1}$—, —$BR^{a2}$—, —$SiR^bR^c$—, —$SiR^{bb}R^{cc}$—, —$GeR^dR^e$—, —$GeR^{dd}R^{ee}$—, —$(CR^fR^g)_{n1}$—, —$(CR^fR^{gg})$—, —$(C(R^m)=C(R^n))$—, —$(C(R^{mm})=C(R^n))$—, —$(C(R^p)=N))$—, or a single bond, wherein $R^{a1}$, $R^{a2}$, $R^b$, $R^c$, $R^d$, $R^e$, $R^f$, $R^g$, $R^m$, $R^n$, and $R^p$ may independently be hydrogen, deuterium, a halogen, a substituted or unsubstituted C1 to C20 alkyl group, or a substituted or unsubstituted C6 to C20 aryl group, at least one pair of $R^{bb}$ and $R^{cc}$, $R^{dd}$ and $R^{ee}$, $R^{ff}$ and $R^{gg}$, or $R^{mm}$ and $R^{nn}$ is linked with each other to provide a ring structure, and n1 of —$(CR^fR^g)_{n1}$— is 1 or 2,
$L^{11}$ may be B or N, and
hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or -unsubstituted C6 to C20 aryl group, and a substituted or unsubstituted C6 to C20 aryloxy group.

According to an embodiment, CH of a 6-membered ring structure (for example, a benzene ring and/or a cyclohexadiene ring) in Chemical Formula 2C-22 may be replaced by N, and one or more (e.g., 1, 2, or 3) N may be included in one 6-member ring structure.

According to an embodiment, in Chemical Formula 2C, $Y^5$ ($CR^k$) and L (—$NR^{a1}$—, —$BR^{a2}$—, —$SiR^bR^c$—, —$GeR^dR^e$—, —$(CR^fR^g)_n$—, —$(C(R^m)=C(R^n))$—, or —$(C(R^p)=N))$—) may be linked to each other to provide a first fused ring and $Y^1$ ($CR^k$) and L (—$NR^{a1}$—, —$BR^{a2}$—, —$SiR^bR^c$—, —$GeR^dR^e$—, —$(CR^fR^g)_n$—, —$(C(R^m)=C(R^n))$—, or —$(C(R^p)=N))$—) may be linked to each other to provide a second fused ring. When the first fused ring and the second fused ring each have a 6-membered ring structure, it may be represented by Chemical Formula 2C-3a or Chemical Formula 2C-3b.

[Chemical Formula 2C-3a]

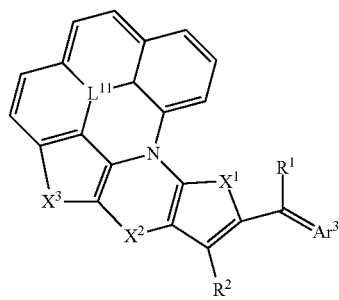

[Chemical Formula 2C-3b]

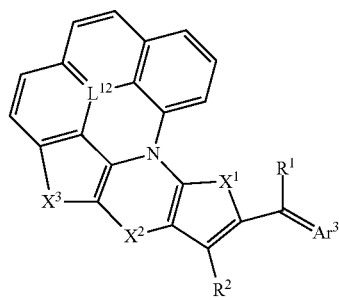

In Chemical Formula 2C-3a and Chemical Formula 2C-3b,
$X^1$, $X^2$, $Ar^3$, $R^1$, and $R^2$ are the same as in Chemical Formula 1,
$X^3$ are the same as in Chemical Formula 2C,
$L^{11}$ may be B or N,
$L^{12}$ may be Si, Ge, or C, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, CH of a 6-membered ring structure (for example, a benzene ring and/or a cyclohexadiene ring) in Chemical Formula 2C-3a and Chemical Formula 2C-3b may be replaced by N, and one or more (e.g., 1, 2, or 3) N may be included in one 6-member ring structure.

In Chemical Formula 20, when $Y^1$ to $Y^4$ are $CR^k$ and adjacent $R^k$'s are linked to each other to provide a fused ring (a substituted or unsubstituted C6 to C30 arene group, a substituted or unsubstituted C3 to C30 heteroarene group, a substituted or unsubstituted C5 to C30 cycloalkene group, a substituted or unsubstituted C5 to C30 cycloalkene group, or a combination thereof), it may be represented by one of Chemical Formula 2C-41 to Chemical Formula 2C-44.

[Chemical Formula 2C-41]

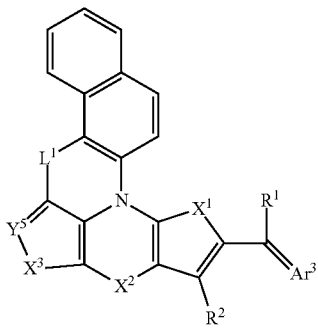

[Chemical Formula 2C-42]

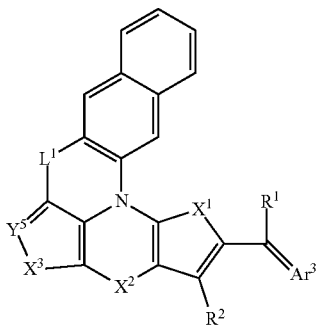

[Chemical Formula 2C-43]

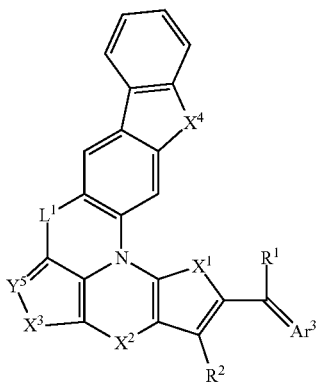

[Chemical Formula 2C-44]

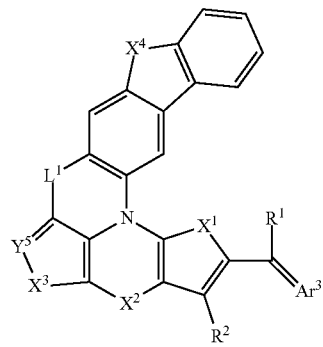

In Chemical Formula 2C-41 to Chemical Formula 2C-44, $X^1$, $X^2$, L, $Ar^3$, $R^1$, and $R^2$ are the same as in Chemical Formula 1, $X^3$ and $Y^5$ are the same as in Chemical Formula 2C, $X^4$ may be —O—, —S—, —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —CR$^f$R$^g$—, —CR$^{ff}$R$^{gg}$—, —CR$^h$=CR$^i$—, or —CR$^{hh}$=CR$^{ii}$—, wherein R$^{a1}$, R$^{a2}$, R$^b$, R$^c$, R$^d$, R$^e$, R$^f$, R$^g$, R$^h$, R$^i$ and R$^j$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of R$^{bb}$ and R$^{cc}$, R$^{dd}$ and R$^{ee}$, R$^{ff}$ and R$^{gg}$, or R$^{hh}$ and R$^{ii}$ is linked with each other to provide a ring structure, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, in Chemical Formula 2C-41 to Chemical Formula 2C-44, CH of the aromatic ring may be replaced by N, and one or more (e.g., 1, 2, or 3) N may be included.

In addition, in Chemical Formula 2C, when $X^3$ and $Y^5$ are linked to each other to provide a fused ring (a substituted or unsubstituted C6 to C30 arene group, a substituted or unsubstituted C3 to C30 heteroarene group, a substituted or unsubstituted C5 to C30 cycloalkene group, a substituted or unsubstituted C5 to C30 cycloalkene group, or a combination thereof), it may be represented by one of Chemical Formula 2C-45 to Chemical Formula 20-50.

[Chemical Formula 2C-45]

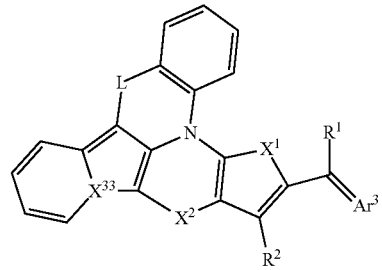

[Chemical Formula 2C-46]

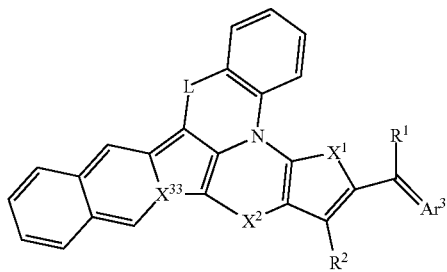

[Chemical Formula 2C-47]

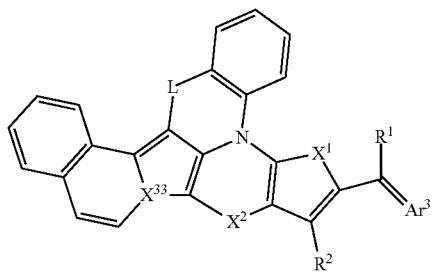

[Chemical Formula 2C-48]

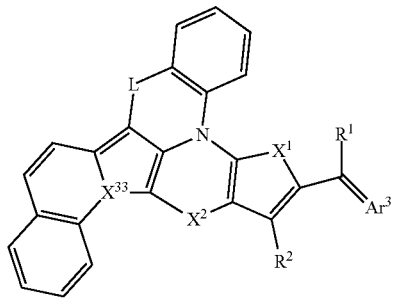

[Chemical Formula 2C-49]

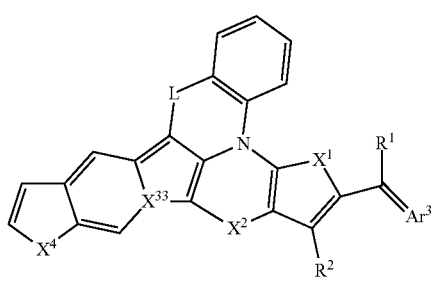

[Chemical Formula 2C-50]

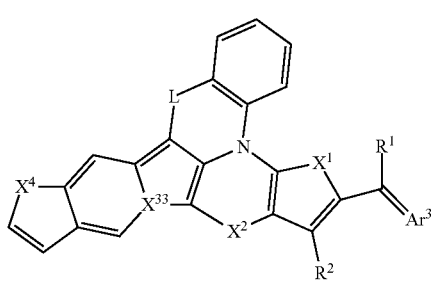

In Chemical Formula 2C-45 or Chemical Formula 2C-50, $X^1$, $X^2$, L, $Ar^3$, $R^1$, and $R^2$ are the same as in Chemical Formula 1, $X^{33}$ may be N, $SiR^b$, $GeR^d$, or $CR^f$, wherein $R^b$, $R^d$, and $R^f$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, $X^4$ may be —O—, —S—, —Se—, —Te—, —S(=O)—, —S(=O)$_2$—, —$NR^{a1}$—, —$BR^{a2}$—, —$SiR^bR^c$—, —$SiR^{bb}R^{cc}$—, —$GeR^dR^e$—, —$GeR^{dd}R^{ee}$—, —$CR^fR^g$—, —$CR^{ff}R^{gg}$—, —$CR^h$=$CR^i$—, or —$CR^{hh}$=$CR^{ii}$—, wherein $R^{a1}$, $R^{a2}$, $R^b$, $R^c$, $R^d$, $R^e$, $R^f$, $R^g$, $R^h$, $R^i$ and $R^j$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of $R^{bb}$ and $R^{cc}$, $R^{dd}$ and $R^{ee}$, $R^{ff}$ and $R^{gg}$, or $R^{hh}$ and $R^{ii}$ is linked with each other to provide a ring structure, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, in Chemical Formula 2C-45 to Chemical Formula 20-50, CH of the aromatic ring may be replaced by N, and one or more (e.g., 1, 2, or 3) N may be included.

The compound of Chemical Formula 1 may be represented by Chemical Formula 2D.

[Chemical Formula 2D]

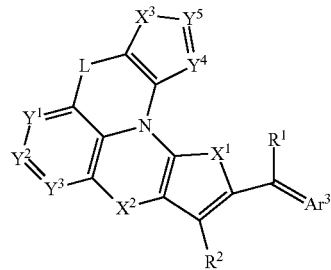

In Chemical Formula 2D, $X^1$, $X^2$, L, $Ar^3$, $R^1$, and $R^2$ are the same as in Chemical Formula 1, $Y^1$ to $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, and $X^3$ may be —O—, —S—, —Se—, —Te—, —S(=O)—, —S(=O)$_2$—, —$NR^{a1}$—, —$BR^{a2}$—, —$SiR^bR^c$—, —$SiR^{bb}R^{cc}$—, —$GeR^dR^e$—, —$GeR^{dd}R^{ee}$—, —$CR^fR^g$—, or —$CR^{ff}R^{gg}$—, wherein $R^{a1}$, $R^{a2}$, $R^b$, $R^c$, $R^d$, $R^e$, $R^f$, and $R^g$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of $R^{bb}$ and $R^{cc}$, $R^{dd}$ and $R^{ee}$, or $R^{ff}$ and $R^{gg}$ is linked to each other to provide a ring structure.

In an embodiment, in Chemical Formula 2D, $Y^4$ may be N or $CR^k$, wherein $R^k$ is a halogen, a cyano group, a C1 to C10 haloalkyl group, or a C1 to C10 cyanoalkyl group. In this case, $Y^4$, N, $X^1$, and functional groups (C=O, C=S, C=Se, or C=Te) present in $Ar^3$ increase an intramolecular interaction, thereby increasing the absorption intensity at a specific wavelength.

In an embodiment, in Chemical Formula 2D, $Y^3$ may be N or $CR^k$, wherein $R^k$ is a halogen, a cyano group, a C1 to C10 haloalkyl group, or a C1 to C10 cyanoalkyl group and $X^2$ may be —O—, —S—, —Se—, —Te—, —S(=O)—, —S(=O)$_2$—, —$NR^{a1}$—, —$BR^{a2}$—, —$SiR^bR^c$—, —$GeR^dR^e$—, —$(CR^fR^g)_{n1}$—, —$(C(R^m)=C(R^n))$—, or —$(C(R^p)=N))$— (wherein $R^{a1}$, $R^{a2}$, $R^b$, $R^c$, $R^d$, $R^e$, $R^f$, $R^g$, $R^m$, $R^n$, and $R^p$ may independently be a halogen, a C1 to C20 haloalkyl group, or a C1 to C20 cyanoalkyl group. In this case, $Y^3$ and $X^2$ may increase an intramolecular interaction, thereby improving the absorption intensity at a specific wavelength.

The compound represented by Chemical Formula 2D may be represented by Chemical Formula 2D-a to Chemical Formula 2D-f depending on the type of L.

[Chemical Formula 2D-a]

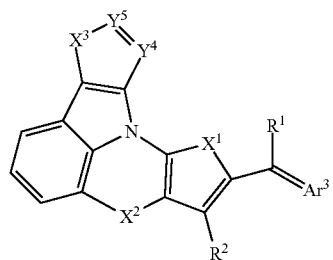

[Chemical Formula 2D-b]

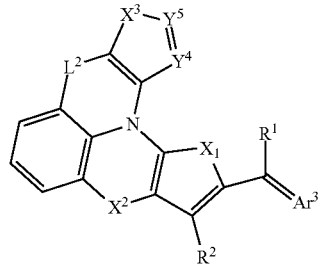

[Chemical Formula 2D-c]

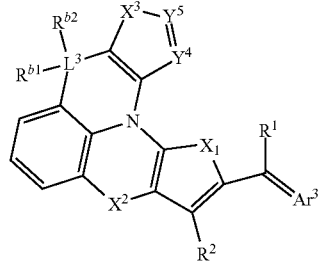

[Chemical Formula 2D-d]

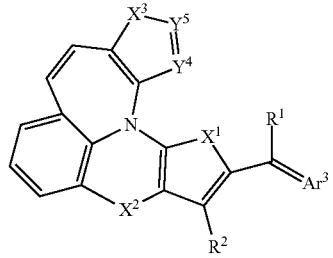

[Chemical Formula 2D-e]

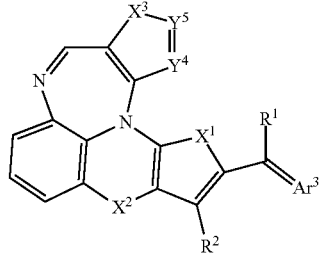

[Chemical Formula 2D-f]

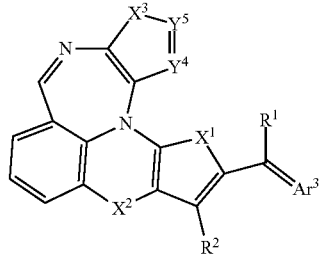

In Chemical Formula 2D-a to Chemical Formula 2D-f,
$X^1$, $X^2$, $Ar^3$, $R^1$, and $R^2$ are the same as in Chemical Formula 1,
$X^3$ is the same as in Chemical Formula 2D,
$Y^4$ and $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof,
$L^2$ may be —O—, —S—, —Se—, —Te—, —$NR^{a1}$—, or —$BR^{a2}$—, wherein $R^{a1}$ and $R^{a2}$ may independently be hydrogen, deuterium, a halogen, a substituted or unsubstituted C1 to C20 alkyl group, or a substituted or unsubstituted C6 to C20 aryl group,
$L^3$ may be Si, Ge, or C,
$R^{b1}$ and $R^{b2}$ may be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and
hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

In Chemical Formula 2D, $Y^1$ ($CR^k$) and L (—$NR^{a1}$—, —$BR^{a2}$—, —$SiR^bR^c$—, —$GeR^dR^e$—, —$(CR^fR^g)_n$—, —$(C(R^m)=C(R^n))$—, or —$(C(R^p)=N))$—) may be linked to each other to provide a fused ring. This structure may be represented by Chemical Formula 2D-1.

[Chemical Formula 2D-1]

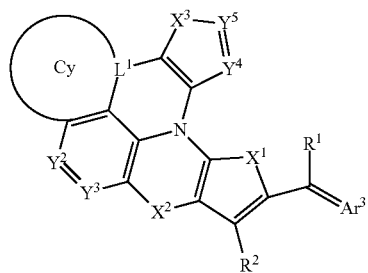

In Chemical Formula 2D-1, $X^1$, $X^2$, $Ar^3$, $R^1$, and $R^2$ are the same as in Chemical Formula 1, $X^3$ is the same as in Chemical Formula 2D, $L^1$ may be N, B, Si, Ge, or C, $Y^2$ to $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, Cy may be a substituted or unsubstituted C6 to C30 arene group, for example a substituted or unsubstituted C6 to C20 arene group or a substituted or unsubstituted C6 to C10 arene group; a substituted or unsubstituted C3 to C30 heteroarene group, for example a substituted or unsubstituted C3 to C20 heteroarene group or a substituted or unsubstituted C3 to C10 heteroarene group; a substituted or unsubstituted C5 to C30 cycloalkene group, for example a substituted or unsubstituted C5 to C20 cycloalkene group or a substituted or unsubstituted C5 to C10 cycloalkene group; a substituted or unsubstituted C5 to C30 heterocycloalkene group, for example a substituted or unsubstituted C5 to C20 heterocycloalkene group or a substituted or unsubstituted C5 to C10 heterocycloalkene group; or a condensed ring thereof.

In Chemical Formula 2D, $X^3$ (—$NR^{a1}$—, —$BR^{a2}$—, —$SiR^bR^c$—, —$GeR^dR^e$—, or —$CR^fR^g$—) and L (—$NR^{a1}$—, —$BR^{a2}$—, —$SiR^bR^c$—, —$GeR^dR^e$—, —$(CR^fR^g)_n$—, —$(C(R^m)=C(R^n))$—, or —$(C(R^p)=N))$—) may be linked to each other to provide a fused ring. This structure may be represented by Chemical Formula 2D-2.

[Chemical Formula 2D-2]

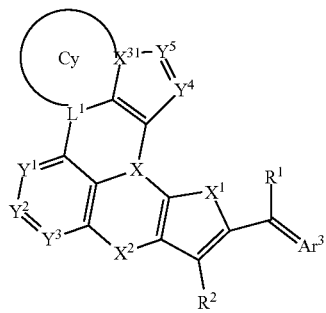

In Chemical Formula 2D-2, $X^1$, $X^2$, $Ar^3$, $R^1$, and $R^2$ are the same as in Chemical Formula 1, $X^{31}$ may be N, $SiR^b$, $GeR^d$, $CR^f$, Si, Ge, or C, wherein $R^b$, $R^d$, and $R^f$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, $L^1$ may be N, B, Si, Ge, or C, $Y^1$ to $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, and Cy may be a substituted or unsubstituted C6 to C30 arene group, for example a substituted or unsubstituted C6 to C20 arene group or a substituted or unsubstituted C6 to C10 arene group; a substituted or unsubstituted C3 to C30 heteroarene group, for example a substituted or unsubstituted C3 to C20 heteroarene group or a substituted or unsubstituted C3 to C10 heteroarene group; a substituted or unsubstituted C5 to C30 cycloalkene group, for example a substituted or unsubstituted C5 to C20 cycloalkene group or a substituted or unsubstituted C5 to C10 cycloalkene group; a substituted or unsubstituted C5 to C30 heterocycloalkene group, for example a substituted or unsubstituted C5 to C20 heterocycloalkene group or a substituted or unsubstituted C5 to C10 heterocycloalkene group; or a condensed ring thereof.

In an embodiment, Cy of Chemical Formulas 2D-1 and 2D-2 may be an arene group, a heteroarene group, a cycloalkene group, or a heterocycloalkene group, and they may have a 5-membered to 10-membered ring structure. The heteroarene group or heterocycloalkene group may include N in the ring.

When Cy of Chemical Formula 2D-1 has a 6-membered ring structure, the compound of Chemical Formula 2D may be represented by Chemical Formula 2D-11a or Chemical Formula 2D-11b.

[Chemical Formula 2D-11a]

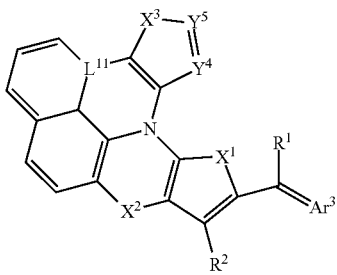

[Chemical Formula 2D-11b]

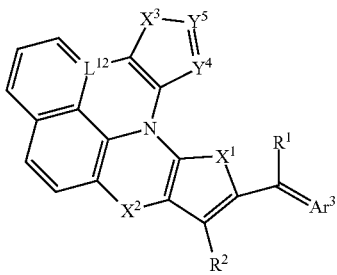

In Chemical Formula 2D-11a and Chemical Formula 2D-11b, $X^1$, $X^2$, $Ar^3$, $R^1$, and $R^2$ are the same as in Chemical Formula 1, $X^3$ is the same as in Chemical Formula 2D, $Y^4$ and $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, $L^{11}$ may be B or N, $L^{12}$ may be Si, Ge, or C, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, CH of a 6-membered ring structure (for example, a benzene ring and/or a cyclohexadiene ring) in Chemical Formula 2D-11a and Chemical Formula 2D-11b may be replaced by N, and one or more (e.g., 1, 2, or 3) N may be included in one 6-member ring structure.

When Cy of Chemical Formula 2D-1 has two fused 6-membered ring structures (a hexagonal ring including $L^4$ and $L^{11}$ and a benzene ring fused thereto in Chemical Formula 2D-12), the compound of Chemical Formula 2D-1 may be represented by Chemical Formula 2D-12.

[Chemical Formula 2D-12]

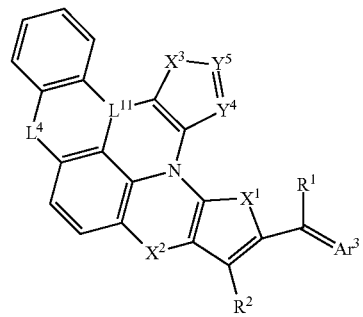

In Chemical Formula 2D-12, $X^1$, $X^2$, $Ar^3$, $R^1$, and $R^2$ are the same as in Chemical Formula 1, $X^3$ is the same as in Chemical Formula 2D, $Y^4$ and $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, $L^4$ may be —O—, —S—, —Se—, —Te—, —$NR^{a1}$—, —$BR^{a2}$—, —$SiR^bR^c$—, —$SiR^{bb}R^{cc}$—, —$GeR^dR^e$—, —$GeR^{dd}R^{ee}$—, —$(CR^fR^g)_{n1}$—, —$(CR^{ff}R^{gg})$—, —$(CR^m)=C(R^n)$—, —$(C(R^{mm})=C(R^{nn})$—, —$(C(R^p)=N))$—, or a single bond, wherein $R^{a1}$, $R^{a2}$, $R^b$, $R^c$, $R^d$, $R^e$, $R^f$, $R^g$, $R^m$, $R^n$, and $R^p$ may independently be hydrogen, deuterium, a halogen, a substituted or unsubstituted C1 to C20 alkyl group, or a substituted or unsubstituted C6 to C20 aryl group, at least one pair of $R^{bb}$ and $R^{cc}$, $R^{dd}$ and $R^{ee}$, $R^{ff}$ and $R^{gg}$, or $R^{mm}$ and $R^{nn}$ is linked with each other to provide a ring structure, and n1 of —$(CR^fR^g)_{n1}$— is 1 or 2, $L^{11}$ may be B or N, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, in Chemical Formula 2D-12, CH of a 6-membered ring structure (e.g., a benzene ring) may be replaced by N, and at least one (e.g., 1, 2 or 3) of N may be included.

When Cy of Chemical Formula 2D-2 has a 6-membered ring structure, it may be represented by Chemical Formula 2D-21a or Chemical Formula 2D-21b.

[Chemical Formula 2D-21a]

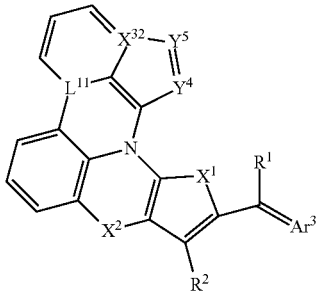

[Chemical Formula 2D-21b]

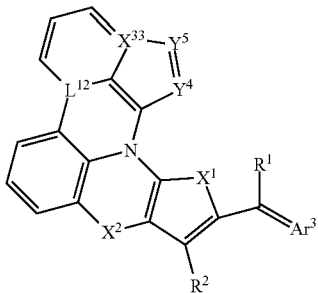

In Chemical Formula 2D-21a and Chemical Formula 2D-21b, $X^1$, $X^2$, $Ar^3$, $R^1$, and $R^2$ are the same as in Chemical Formula 1, $Y^4$ and $Y^5$ are the same as in Chemical Formula 2D, $L^{11}$ may be B or N, $L^{12}$ may be Si, Ge, or C, $X^{32}$ may be Si, Ge, or C, $X^{33}$ is N, $SiR^b$, $GeR^d$, or $CR^f$, wherein $R^b$, $R^d$, and $R^f$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, CH of a 6-membered ring structure (for example, a benzene ring and/or a cyclohexadiene ring) in Chemical Formula 2D-21a and Chemical Formula 2D-21b may be replaced by N, and one or more (e.g., 1, 2, or 3) N may be included in one 6-member ring structure.

When Cy of Chemical Formula 2D-2 has two fused 6-membered ring structures (a hexagonal ring including $L^4$ and $L^{11}$ and a benzene ring fused thereto in Chemical Formula 2D-22), the compound of Chemical Formula 2D-2 may be represented by Chemical Formula 2D-22.

[Chemical Formula 2D-22]

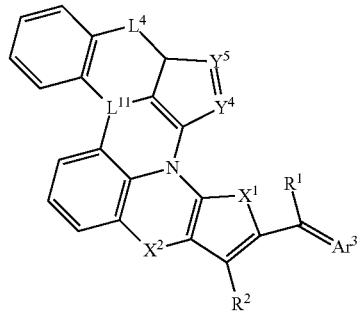

In Chemical Formula 2D-22, $X^1$, $X^2$, $Ar^3$, $R^1$, and $R^2$ are the same as in Chemical Formula 1, $Y^4$ and $Y^5$ are the same as in Chemical Formula 2D, $L^4$ may be —O—, —S—, —Se—, —Te—, —$NR^{a1}$—, —$BR^{a2}$—, —$SiR^bR^c$—, —$SiR^{bb}R^{cc}$—, —$GeR^dR^e$—, —$GeR^{dd}R^{ee}$—, —$(CR^fR^g)_{n1}$—, —$(CR^{ff}R^{gg})$—, —$(C(R^m)=C(R^n))$—, —$(C(R^{mm})=C(R^n))$—, —$(C(R^p)=N))$—, or a single bond, wherein $R^{a1}$, $R^{a2}$, $R^b$, $R^c$, $R^d$, $R^e$, $R^f$, $R^g$, $R^m$, $R^n$, or $R^p$ may independently be hydrogen, deuterium, a halogen, a substituted or unsubstituted C1 to C20 alkyl group, or a substituted or unsubstituted C6 to C20 aryl group, at least one pair of $R^{bb}$ and $R^{cc}$, $R^{dd}$ and $R^{ee}$, $R^{ff}$ and $R^{gg}$, or $R^{mm}$ and $R^{nn}$ is linked with each other to provide a ring structure, and n1 of —$(CR^fR^g)_{n1}$— is 1 or 2, $L^{11}$ may be B or N, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, in Chemical Formula 2D-22, CH of the aromatic ring may be replaced by N, and one or more (e.g., 1, 2, or 3) N may be included.

According to an embodiment, in Chemical Formula 2D, $Y^1$ ($CR^k$) and L (—$NR^{a1}$—, —$BR^{a2}$—, —$SiR^bR^c$—, —$GeR^dR^e$—, —$(CR^fR^g)_n$—, —$(C(R^m)=C(R^n))$—, or —$(C(R^p)=N))$—) may be linked to each other to provide a first fused ring and $X^3$ (—$NR^{a1}$—, —$BR^{a2}$—, —$SiR^bR^c$—, —$GeR^dR^e$—, or —$CR^fR^g$—) and L (—$NR^{a1}$—, —$BR^{a2}$—, —$SiR^bR^c$—, —$GeR^dR^e$—, —$(CR^fR^g)$—, —$(C(R^m)=C(R^n))$—, or —$(C(R^p)=N))$—) may be linked to each other to provide a second fused ring. When the first fused ring and the second fused ring each have a 6-membered ring structure, it may be represented by Chemical Formula 2D-3a or Chemical Formula 2D-3b.

[Chemical Formula 2D-3a]

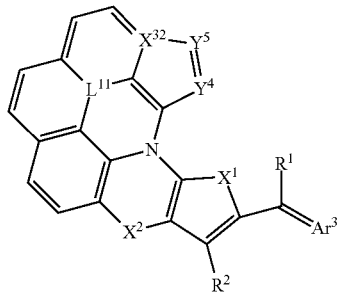

[Chemical Formula 2D-3b]

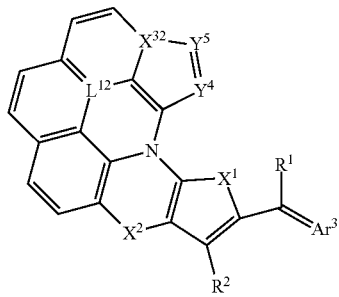

In Chemical Formula 2D-3a and Chemical Formula 2D-3b, $X^1$, $X^2$, $Ar^3$, $R^1$, and $R^2$ are the same as in Chemical Formula 1, $L^{11}$ may be B or N, $L^{12}$ may be Si, Ge, or C, $X^{32}$ may be Si, Ge, or C, $X^{33}$ may be N, $SiR^b$, $GeR^d$, or $CR^f$, wherein $R^b$, $R^d$ and $R^f$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and $Y^4$ and $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof.

According to an embodiment, CH of a 6-membered ring structure (for example, a benzene ring and/or a cyclohexadiene ring) in Chemical Formula 2D-3a and Chemical Formula 2D-3b may be replaced by N, and one or more (e.g., 1, 2, or 3) N may be included in one 6-member ring structure.

In addition, in Chemical Formula 2D, when $X^3$ and $Y^5$ or $Y^4$ and $Y^5$ are linked to each other to provide a fused ring (a substituted or unsubstituted C6 to C30 arene group, a substituted or unsubstituted C3 to C30 heteroarene group, a substituted or unsubstituted C5 to C30 cycloalkene group, a substituted or unsubstituted C5 to C30 cycloalkene group, or a combination thereof), it may be represented by one of Chemical Formula 2D-41 to Chemical Formula 2D-46.

[Chemical Formula 2D-41]

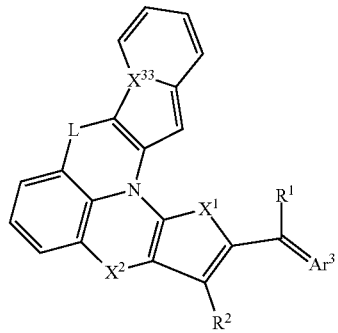

[Chemical Formula 2D-42]

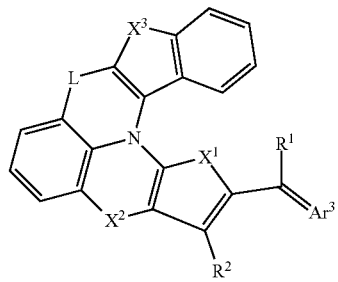

[Chemical Formula 2D-43]

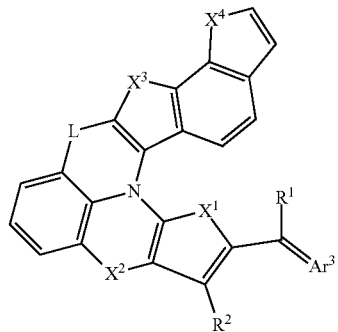

[Chemical Formula 2D-44]

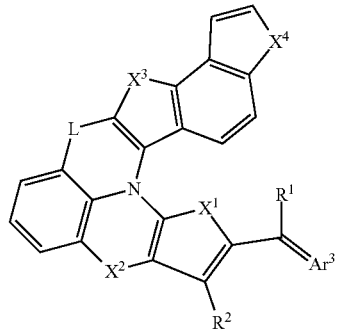

-continued

[Chemical Formula 2D-45]

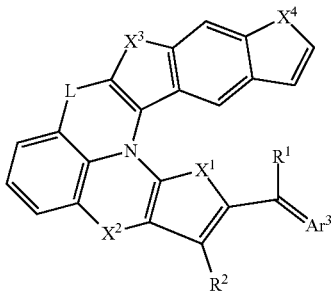

[Chemical Formula 2D-46]

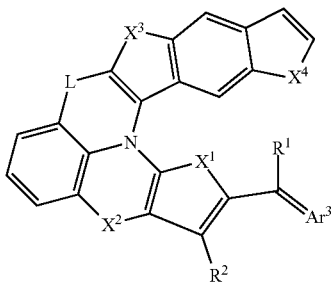

In Chemical Formula 2D-41 to Chemical Formula 2D-46, $X^1$, $X^2$, L, $Ar^3$, $R^1$, and $R^2$ are the same as in Chemical Formula 1, $X^{33}$ may be N, $SiR^b$, $GeR^d$, or $CR^f$, wherein $R^b$, $R^d$ and $R^f$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, $X^4$ may be —O—, —S—, —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —CR$^f$R$^g$—, —CR$^{ff}$R$^{gg}$—, —CR$^h$=CR$^i$—, or —CR$^{hh}$=CR$^{ii}$—, wherein R$^{a1}$, R$^{a2}$, R$^b$, R$^c$, R$^d$, R$^e$, R$^f$, R$^g$, R$^h$, R$^i$ and R$^j$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of R$^{bb}$ and R$^{cc}$, R$^{dd}$ and R$^{ee}$, R$^{ff}$ and R$^{gg}$, or R$^{hh}$ and R$^{ii}$ is linked with each other to provide a ring structure, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, in Chemical Formula 2D-41 to Chemical Formula 2D-46, CH of an aromatic ring may be replaced by N, and one or more (e.g., 1, 2, or 3) N may be included in one 6-member ring structure.

In addition, in Chemical Formula 2D, when adjacent two of $Y^1$ to $Y^3$ are linked to each other to provide a fused ring (a substituted or unsubstituted C6 to C30 arene group, a substituted or unsubstituted C3 to C30 heteroarene group, a substituted or unsubstituted C5 to C30 cycloalkene group, a substituted or unsubstituted C5 to C30 cycloalkene group, or a combination thereof), it may be represented by one of Chemical Formula 2D-47 to Chemical Formula 2D-50.

[Chemical Formula 2D-47]

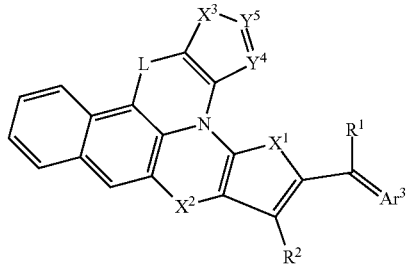

[Chemical Formula 2D-48]

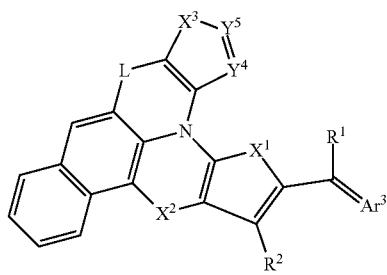

[Chemical Formula 2D-49]

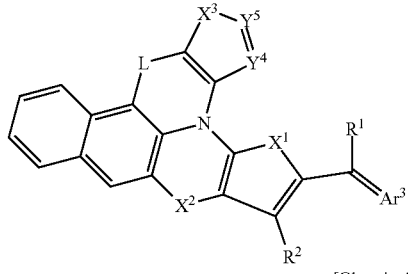

[Chemical Formula 2D-50]

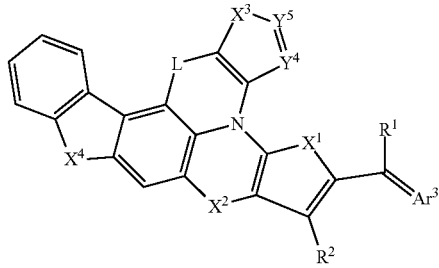

In Chemical Formula 2D-47 to Chemical Formula 2D-50, $X^1$, $X^2$, L, $Ar^3$, $R^1$, and $R^2$ are the same as in Chemical Formula 1, $X^3$, $Y^4$, and $Y^5$ are the same as in Chemical Formula 2D, $X^4$ may be —O—, —S—, —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —CR$^f$R$^g$—, —CR$^{ff}$R$^{gg}$—, —CR$^h$=CR$^i$—, or —CR$^{hh}$=CR$^{ii}$—, wherein R$^{a1}$, R$^{a2}$, R$^b$, R$^c$, R$^d$, R$^e$, R$^f$, R$^g$, R$^h$, R$^i$ and R$^j$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of R$^{bb}$ and R$^{cc}$, $R^{dd}$ and $R^{ee}$, $R^{ff}$ and $R^{gg}$, or $R^{hh}$ and $R^{ii}$ is linked with each other to provide a ring structure, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, in Chemical Formula 2D-47 to Chemical Formula 2D-50, CH of the aromatic ring may be replaced by N, and one or more (e.g., 1, 2, or 3) N may be included.

The compound of Chemical Formula 1 may be represented by Chemical Formula 2E.

[Chemical Formula 2E]

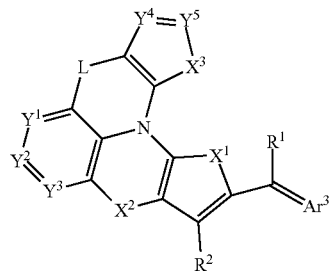

In Chemical Formula 2E, $X^1$, $X^2$, L, $Ar^3$, $R^1$, and $R^2$ are the same as in Chemical Formula 1, $Y^1$ to $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, and $X^3$ may be —O—, —S—, —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —CR$^f$R$^g$—, or —CR$^{ff}$R$^{gg}$—, wherein $R^{a1}$, $R^{a2}$, $R^b$, $R^c$, $R^d$, $R^e$, $R^f$, and $R^g$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of $R^{bb}$ and $R^{cc}$, $R^{dd}$ and $R^{ee}$, or $R^{ff}$ and $R^{gg}$ is linked to each other to provide a ring structure.

In an embodiment, in Chemical Formula 2E, $X^3$ may be —O—, —S—, —Se—, —Te—, —S(=O)—, —S(=O)$_2$—, —NR$^{a1}$—, —BR$^{a2}$—, —SiR$^b$R$^c$—, —GeR$^d$R$^e$—, or —CR$^f$R$^g$—, wherein $R^{a1}$, $R^{a2}$, $R^b$, $R^c$, $R^d$, $R^e$, $R^f$, and $R^g$ may independently be a halogen, a C1 to C20 haloalkyl group, or a C1 to C20 cyanoalkyl group. In this case, $X^3$, N, $X^1$, and functional groups (C=O, C=S, C=Se, or C=Te) present in $Ar^3$ increase an intramolecular interaction, thereby increasing the absorption intensity at a specific wavelength.

In an embodiment, in Chemical Formula 2E, $Y^3$ is N or $CR^k$, wherein $R^k$ is a halogen, a cyano group, a C1 to C10 haloalkyl group, or a C1 to C10 cyanoalkyl group and $X^2$ is —O—, —S—, —Se—, —Te—, —S(=O)—, —S(=O)$_2$—, —NR$^{a1}$—, —BR$^{a2}$—, —SiR$^b$R$^c$—, —GeR$^d$R$^e$—, —(CR$^f$R$^g$)$_{n1}$—, —(C(R$^m$)=C(R$^n$))—, or —(C(R$^p$)=N))—, wherein $R^{a1}$, $R^{a2}$, $R^b$, $R^c$, $R^d$, $R^e$, $R^f$, $R^g$, $R^m$, $R^n$, and $R^p$ may independently be a halogen, a C1 to C20 haloalkyl group, or a C1 to C20 cyanoalkyl group. In this case, $Y^3$ and $X^2$ may increase an intramolecular interaction, thereby improving the absorption intensity at a specific wavelength.

The compound represented by Chemical Formula 2E may be represented by Chemical Formula 2E-a to Chemical Formula 2E-f depending on the type of L.

[Chemical Formula 2E-a]

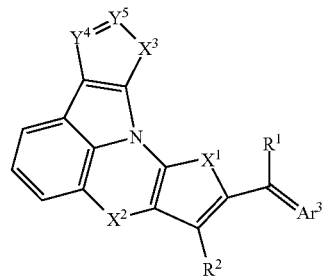

[Chemical Formula 2E-b]

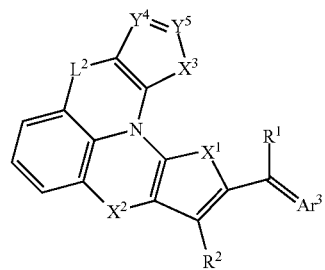

[Chemical Formula 2E-c]

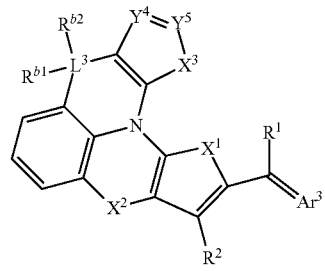

[Chemical Formula 2E-d]

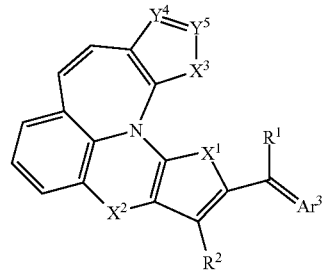

[Chemical Formula 2E-e]

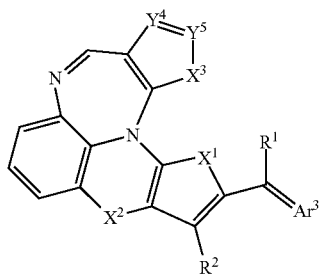

[Chemical Formula 2E-f]

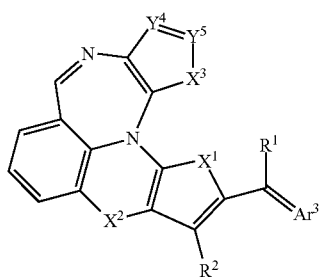

In Chemical Formula 2E-a to Chemical Formula 2E-f, $X^1$, $X^2$, $Ar^3$, $R^1$, and $R^2$ are the same as in Chemical Formula 1, $X^3$ is the same as in Chemical Formula 2E, $Y^4$ and $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, $L^2$ may be —O—, —S—, —Se—, —Te—, —$NR^{a1}$—, or —$BR^{a2}$—, wherein $R^{a1}$ and $R^{a2}$ may independently be hydrogen, deuterium, a halogen, a substituted or unsubstituted C1 to C20 alkyl group, or a substituted or unsubstituted C6 to C20 aryl group, $L^3$ may be Si, Ge, or C, $R^{b1}$ and $R^{b2}$ may be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

In Chemical Formula 2E, $Y^1$ ($CR^k$) and L (—$NR^{a1}$—, —$BR^{a2}$—, —$SiR^bR^c$—, —$GeR^dR^e$—, —$(CR^fR^g)_n$—, —$(CR^m)$=$C(R^n)$)—, or —$(C(R^p)$=$N)$)—) may be linked to each other to provide a fused ring. This structure may be represented by Chemical Formula 2E-1.

[Chemical Formula 2E-1]

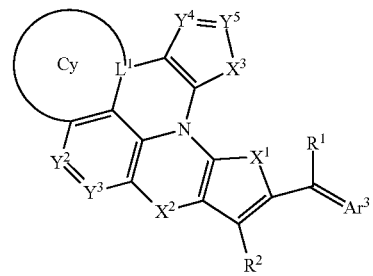

In Chemical Formula 2E-1, $X^1$, $X^2$, $Ar^3$, $R^1$, and $R^2$ are the same as in Chemical Formula 1, $X^3$ is the same as in Chemical Formula 2E, $L^1$ may be N, B, Si, Ge, or C, $Y^2$ to $Y^5$ may independently be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, a substituted or unsubstituted C3 to C30 heteroarene group, or a condensed ring thereof, Cy may be a substituted or unsubstituted C6 to C30 arene group, for example a substituted or unsubstituted C6 to C20 arene group or a substituted or unsubstituted C6 to C10 arene group; a substituted or unsubstituted C3 to C30 heteroarene group, for example a substituted or unsubstituted C3 to C20 heteroarene group or a substituted or unsubstituted C3 to C10 heteroarene group; a substituted or unsubstituted C5 to C30 cycloalkene group, for example a substituted or unsubstituted C5 to C20 cycloalkene group or a substituted or unsubstituted C5 to C10 cycloalkene group; a substituted or unsubstituted C5 to C30 heterocycloalkene group, for example a substituted or unsubstituted C5 to C20 heterocycloalkene group or a substituted or unsubstituted C5 to C10 heterocycloalkene group; or a condensed ring thereof.

In Chemical Formula 2E, $Y^4$ ($CR^k$) and L (—$NR^{a1}$—, —$BR^{a2}$—, —$SiR^bR^c$—, —$GeR^dR^e$—, —$(CR^fR^g)_n$—, —$(C(R^m)$=$C(R^n)$)— or —$(C(R^p)$=$N)$)—) may be linked to each other to provide a fused ring. This structure may be represented by Chemical Formula 2E-2.

[Chemical Formula 2E-2]

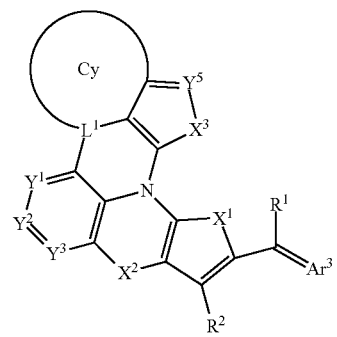

In Chemical Formula 2E-2,

X$^1$, X$^2$, Ar$^3$, R$^1$, and R$^2$ are the same as in Chemical Formula 1,

X$^3$ is the same as in Chemical Formula 2E,

L$^1$ may be N, B, Si, Ge, or C,

Y$^1$ to Y$^3$ and Y$^5$ may independently be N or CR$^k$, wherein R$^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent R$^k$'s are linked to each other to provide a substituted or unsubstituted C6 to C30 arene group, a substituted or unsubstituted C3 to C30 heteroarene group, or a condensed ring thereof, and Cy may be a substituted or unsubstituted C6 to C30 arene group, for example a substituted or unsubstituted C6 to C20 arene group or a substituted or unsubstituted C6 to C10 arene group; a substituted or unsubstituted C3 to C30 heteroarene group, for example a substituted or unsubstituted C3 to C20 heteroarene group or a substituted or unsubstituted C3 to C10 heteroarene group; a substituted or unsubstituted C5 to C30 cycloalkene group, for example a substituted or unsubstituted C5 to C20 cycloalkene group or a substituted or unsubstituted C5 to C10 cycloalkene group; a substituted or unsubstituted C5 to C30 heterocycloalkene group, for example a substituted or unsubstituted C5 to C20 heterocycloalkene group or a substituted or unsubstituted C5 to C10 heterocycloalkene group; or a condensed ring thereof.

In an embodiment, Cy of Chemical Formulas 2E-1 and 2E-2 may be an arene group, a heteroarene group, a cycloalkene group, or a heterocycloalkene group, and they may have a 5-membered to 10-membered ring structure. The heteroarene group or heterocycloalkene group may include N in the ring.

When Cy of Chemical Formula 2E-1 has a 6-membered ring structure, the compound of Chemical Formula 2E may be represented by Chemical Formula 2E-11a or Chemical Formula 2E-11b.

[Chemical Formula 2E-11a]

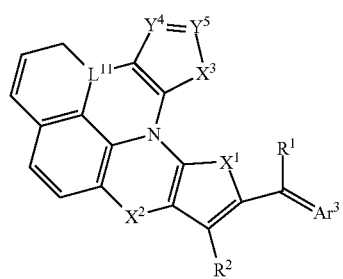

[Chemical Formula 2E-11b]

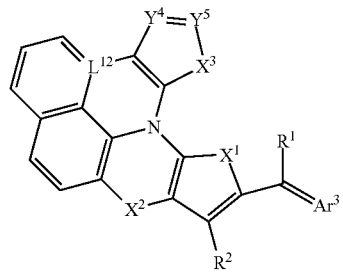

In Chemical Formula 2C-11a and Chemical Formula 2E-11b,

X$^1$, X$^2$, Ar$^3$, R$^1$, and R$^2$ are the same as in Chemical Formula 1,

X$^3$, Y$^4$, and Y$^5$ are the same as in Chemical Formula 2E,

L$^{11}$ may be B or N,

L$^{12}$ may be Si, Ge, or C, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, CH of a 6-membered ring structure (for example, a benzene ring and/or a cyclohexadiene ring) in Chemical Formula 2E-11 may be replaced by N, and one or more (e.g., 1, 2, or 3) N may be included in one 6-member ring structure.

When Cy of Chemical Formula 2E-1 has two fused 6-membered ring structures (a hexagonal ring including L$^4$ and L$^{11}$ and a benzene ring fused thereto in Chemical Formula 2E-12), the compound of Chemical Formula 2E-1 may be represented by Chemical Formula 2E-12.

[Chemical Formula 2E-12]

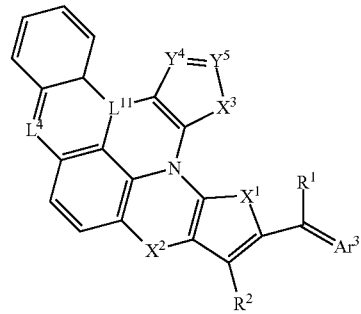

In Chemical Formula 2E-12,

X$^1$, X$^2$, Ar$^3$, R$^1$, and R$^2$ are the same as in Chemical Formula 1,

X$^3$, Y$^4$, and Y$^5$ is the same as in Chemical Formula 2E,

L$^4$ may be —O—, —S—, —Se—, —Te—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —(CR$^f$R$^g$)$_{n1}$—, —(CR$^{ff}$R$^{gg}$)—, —(C(R$^m$)=C(R$^n$)—, —(C(R$^{mm}$)=C(R$^{nn}$))—, —(C(R$^p$)=N))—, or a single bond, wherein R$^{a1}$, R$^{a2}$, R$^b$, R$^c$, R$^d$, R$^e$, R$^f$, R$^g$, R$^m$, R$^n$, and R$^p$ may independently be hydrogen, deuterium, a halogen, a substituted or unsubstituted C1 to C20 alkyl group, or a substituted or unsubstituted C6 to C20 aryl group, at least one pair of R$^{bb}$ and R$^{cc}$, R$^{dd}$ and R$^{ee}$, R$^{ff}$ and R$^{gg}$, or R$^{mm}$ and R$^{nn}$ is linked with each other to provide a ring structure, and n1 of —(CR$^f$R$^g$)$_{n1}$— is 1 or 2, L$^{11}$ may be B or N, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, in Chemical Formula 2E-12, CH of a 6-membered ring structure (e.g., a benzene ring) may be replaced by N, and at least one (e.g., 1, 2 or 3) of N may be included.

When Cy of Chemical Formula 2E-2 has a 6-membered ring structure, it may be represented by Chemical Formula 2E-21a or Chemical Formula 2E-21b.

[Chemical Formula 2E-21a]

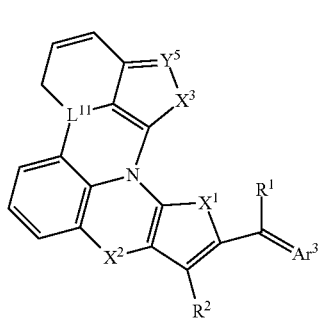

[Chemical Formula 2E-21b]

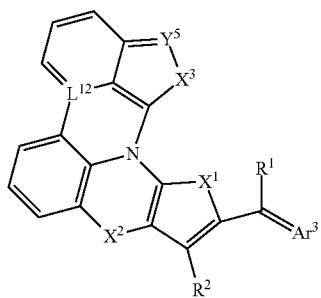

In Chemical Formula 2E-21a and Chemical Formula 2E-21b, $X^1$, $X^2$, $Ar^3$, $R^1$, and $R^2$ are the same as in Chemical Formula 1, $X^3$ and $Y^5$ is the same as in Chemical Formula 2E, $L^{11}$ may be B or N, $L^{12}$ may be Si, Ge, or C, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, CH of a 6-membered ring structure (for example, a benzene ring and/or a cyclohexadiene ring) in Chemical Formula 2E-21a and Chemical Formula 2E-21b may be replaced by N, and one or more (e.g., 1, 2, or 3) N may be included in one 6-member ring structure.

When Cy of Chemical Formula 2E-2 has two fused 6-membered ring structures (a hexagonal ring including $L^4$ and $L^{11}$ and a benzene ring fused thereto in Chemical Formula 2E-22), the compound of Chemical Formula 2E-2 may be represented by Chemical Formula 2E-22.

[Chemical Formula 2E-22]

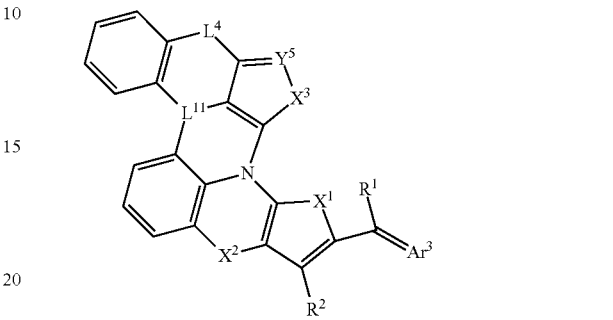

In Chemical Formula 2E-22, $X^1$, $X^2$, $Ar^3$, $R^1$, and $R^2$ are the same as in Chemical Formula 1, $X^3$ and $Y^5$ is the same as in Chemical Formula 2E, $L^4$ may be —O—, —S—, —Se—, —Te—, —$NR^{a1}$—, —$BR^{a2}$—, —$SiR^bR^c$—, —$SiR^{bb}R^{cc}$—, —$GeR^dR^e$—, —$GeR^{dd}R^{ee}$—, —$(CR^fR^g)_{n1}$—, —$(CR^{ff}R^{gg})$—, —$(C(R^m)=C(R^n))$—, —$(C(R^{mm})=C(R^{nn}))$—, —$(C(R^p)=N))$—, or a single bond, wherein $R^{a1}$, $R^{a2}$, $R^b$, $R^c$, $R^d$, $R^e$, $R^f$, $R^g$, $R^m$, $R^n$, and $R^p$ may independently be hydrogen, deuterium, a halogen, a substituted or unsubstituted C1 to C20 alkyl group, or a substituted or unsubstituted C6 to C20 aryl group, at least one pair of $R^{bb}$ and $R^{cc}$, $R^{dd}$ and $R^{ee}$, $R^{ff}$ and $R^{gg}$, or $R^{mm}$ and $R^{nn}$ is linked with each other to provide a ring structure, and n1 of —$(CR^fR^g)_{n1}$— is 1 or 2, $L^{11}$ may be B or N, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, in Chemical Formula 2E-22, CH of the aromatic ring may be replaced by N, and one or more (e.g., 1, 2, or 3) N may be included.

According to an embodiment, in Chemical Formula 2E, $Y^1$ ($CR^k$) and L (—$NR^{a1}$—, —$BR^{a2}$—, —$SiR^bR^c$—, —$GeR^dR^e$—, —$(CR^fR^g)_n$—, —$(C(R^m)=C(R^n))$—, or —$(C(R^p)=N))$—) may be linked to each other to provide a first fused ring and $Y^4$ ($CR^k$) and L (—$NR^{a1}$—, —$BR^{a2}$—, —$SiR^bR^c$—, —$GeR^dR^e$—, —$(CR^fR^g)_n$—, —$(C(R^m)=C(R^n))$—, or —$(C(R^p)=N))$—) may be linked to each other to provide a second fused ring. When the first fused ring and the second fused ring each have a 6-membered ring structure, it may be represented by Chemical Formula 2E-3a or Chemical Formula 2E-3b.

[Chemical Formula 2E-3a]

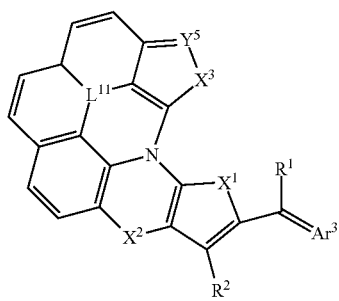

[Chemical Formula 2E-41]

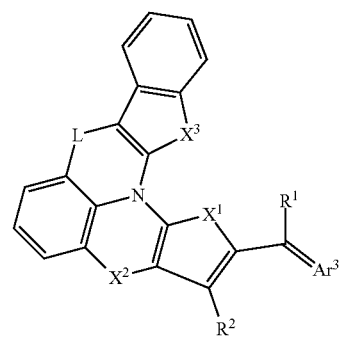

[Chemical Formula 2E-3b]

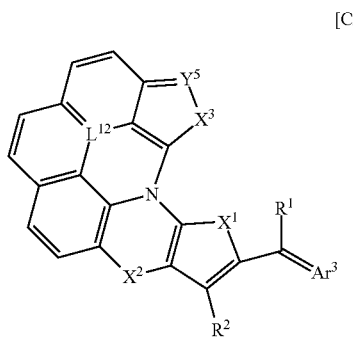

[Chemical Formula 2E-42]

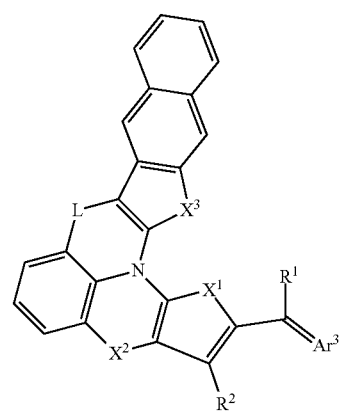

In Chemical Formula 2E-3, $X^1$, $X^2$, $Ar^3$, $R^1$, and $R^2$ are the same as in Chemical Formula 1, $X^3$ is the same as in Chemical Formula 2E, $L^{11}$ may be B or N, $L^{12}$ may be Si, Ge, or C, $Y^5$ may be N or $CR^k$, wherein $R^k$ may be hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group or adjacent $R^k$'s are linked to each other to provide a substituted or unsubstituted C6 to C30 arene group, a substituted or unsubstituted C3 to C30 heteroarene group, or a condensed ring thereof, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

According to an embodiment, CH of a 6-membered ring structure (for example, a benzene ring and/or a cyclohexadiene ring) in Chemical Formula 2E-3a and Chemical Formula 2E-3b may be replaced by N, and one or more (e.g., 1, 2, or 3) N may be included in one 6-member ring structure.

In Chemical Formula 2E, when $Y^4$ and $Y^5$ or $Y^5$ and $X^3$ are linked to each other to provide a fused ring (a substituted or unsubstituted C6 to C30 arene group, a substituted or unsubstituted C3 to C30 heteroarene group, a substituted or unsubstituted C5 to C30 cycloalkene group, a substituted or unsubstituted C5 to C30 cycloalkene group, or a combination thereof), it may be represented by one of Chemical Formula 2E-41 to Chemical Formula 2E-46.

[Chemical Formula 2E-43]

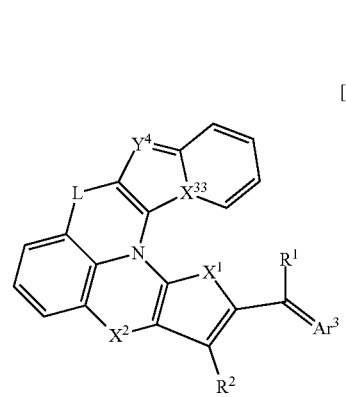

[Chemical Formula 2E-44]

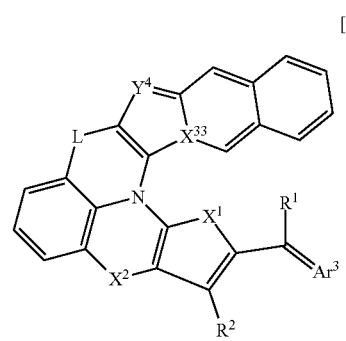

[Chemical Formula 2E-45]

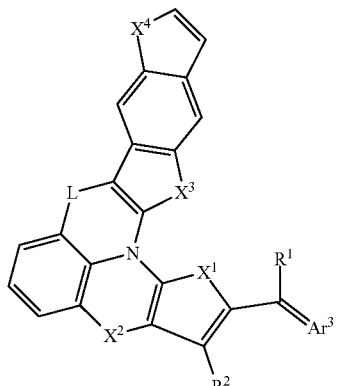

[Chemical Formula 2E-46]

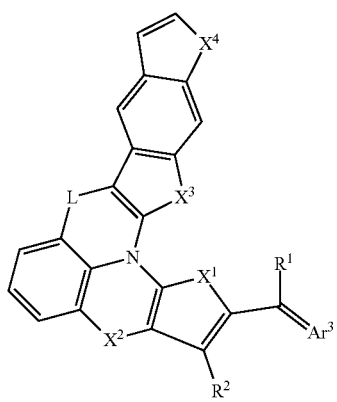

In Chemical Formula 2E-41 to Chemical Formula 2E-46, $X^1$, $X^2$, L, $Ar^3$, $R^1$, and $R^2$ are the same as in Chemical Formula 1, $X^{33}$ may be N, $SiR^b$, $GeR^d$, or $CR^f$, wherein $R^b$, $R^d$, and $R^f$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and $X^3$ and $Y^4$ are the same as in Chemical Formula 2E, $X^4$ may be —O—, —S—, —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —CR$^f$R$^g$—, —CR$^{ff}$R$^{gg}$—, —CR$^h$=CR$^i$—, or —CR$^{hh}$=CR$^{ii}$—, wherein R$^{a1}$, R$^{a2}$, R$^b$, R$^c$, R$^d$, R$^e$, R$^f$, R$^g$, R$^h$, R$^i$ and R$^j$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of R$^{bb}$ and R$^{cc}$, R$^{dd}$ and R$^{ee}$, R$^{ff}$ and R$^{gg}$, or R$^{hh}$ and R$^{ii}$ is linked with each other to provide a ring structure, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

In an embodiment, in Chemical Formula 2E-41 to Chemical Formula 2E-46, CH of the aromatic ring may be replaced by N, and one or more (e.g., 1, 2, or 3) N may be included.

In Chemical Formula 2E, when $Y^1$ to $Y^3$ are $CR^k$ and adjacent $R^k$'s are linked to each other to provide a fused ring (a substituted or unsubstituted C6 to C30 arene group, a substituted or unsubstituted C3 to C30 heteroarene group, a substituted or unsubstituted C5 to C30 cycloalkene group, a substituted or unsubstituted C5 to C30 cycloalkene group, or a combination thereof), it may be represented by one of Chemical Formula 2E-47 to Chemical Formula 2E-50.

[Chemical Formula 2E-47]

[Chemical Formula 2E-48]

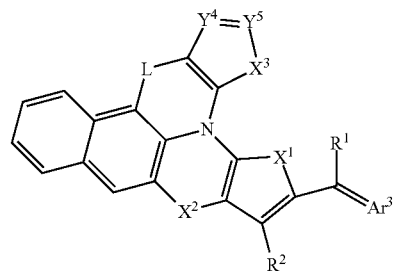

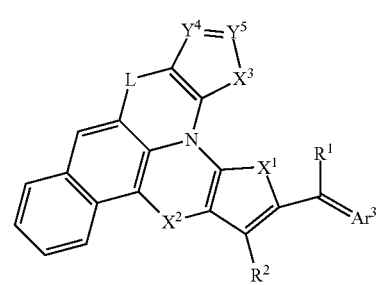

[Chemical Formula 2E-49]

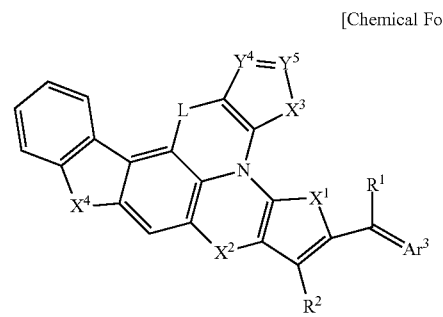

[Chemical Formula 2E-50]

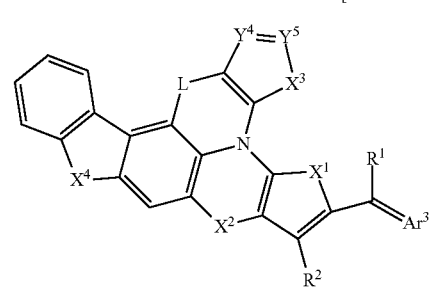

In Chemical Formula 2E-47 to Chemical Formula 2E-50, $X^1$, $X^2$, L, $Ar^3$, $R^1$, and $R^2$ are the same as in Chemical Formula 1, $X^3$, $Y^4$, and $Y^5$ are the same as in Chemical Formula 2E, X⁴ may be —O—, —S—, —Se—, —Te—, —S(=O)—, —S(=O)₂—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —CR$^f$R$^g$—, —CR$^{ff}$R$^{gg}$—, —CR$^h$=CR$^i$—, or —CR$^{hh}$=CR$^{ii}$—, wherein R$^{a1}$, R$^{a2}$, R$^b$, R$^c$, R$^d$, R$^e$, R$^f$, R$^g$, R$^h$, R$^i$ and R$^j$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of R$^{bb}$ and R$^{cc}$, R$^{dd}$ and R$^{ee}$, R$^{ff}$ and R$^{gg}$, or R$^{hh}$ and R$^{ii}$ is linked with each other to provide a ring structure, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group. In an embodiment, in Chemical Formula 2E-47 to Chemical Formula 2E-50, CH of the aromatic ring may be replaced by N, and one or more (e.g., 1, 2, or 3) N may be included.

In X¹, X², and L of Formula 1 and X³ of Chemical Formula 2B, Chemical Formula 2C, and Chemical Formula 2E, the ring structure may be a spiro structure or a fused ring structure. The spiro structure may be a substituted or unsubstituted C5 to C30 hydrocarbon ring group or a substituted or unsubstituted C2 to C30 heterocyclic group. The substituted or unsubstituted C5 to C30 hydrocarbon cyclic group may be for example a substituted or unsubstituted C5 to C30 cycloalkyl group (e.g., a substituted or unsubstituted C3 to C20 cycloalkyl group or a substituted or unsubstituted C3 to C10 cycloalkyl group), or a fused ring of a substituted or unsubstituted C5 to C30 cycloalkyl group (e.g., a substituted or unsubstituted C3 to C20 cycloalkyl group or a substituted or unsubstituted C3 to C10 cycloalkyl group) and a substituted or unsubstituted C6 to C30 aryl group (e.g., a substituted or unsubstituted C6 to C20 aryl group or a substituted or unsubstituted C3 to C10 aryl group). Examples of the fused ring include a fluorenyl group and an indanyl group. The substituted or unsubstituted C2 to C30 heterocyclic group may be for example a substituted or unsubstituted C2 to C30 heterocycloalkyl group (e.g., a substituted or unsubstituted C2 to C20 heterocycloalkyl group or a substituted or unsubstituted C2 to C10 heterocycloalkyl group).

The fused ring structure may have a fused substituted or unsubstituted C5 to C30 hydrocarbon cyclic group, a fused substituted or unsubstituted C2 to C30 heterocyclic group, or a fused ring thereof. The substituted or unsubstituted C5 to C30 hydrocarbon cyclic group may be for example a substituted or unsubstituted C5 to C30 cycloalkyl group (e.g., a substituted or unsubstituted C3 to C20 cycloalkyl group or a substituted or unsubstituted C3 to C10 cycloalkyl group) or a substituted or unsubstituted C6 to C30 aryl group (e.g., a substituted or unsubstituted C6 to C20 aryl group or a substituted or unsubstituted C6 to C10 aryl group) and the substituted or unsubstituted C2 to C30 heterocyclic group may be for example a substituted or unsubstituted C2 to C30 heterocycloalkyl group (e.g., a substituted or unsubstituted C2 to C20 heterocycloalkyl group or a substituted or unsubstituted C2 to C10 heterocycloalkyl group) or a substituted or unsubstituted C2 to C30 heteroaryl group (e.g., a substituted or unsubstituted C2 to C20 heteroaryl group, or a substituted or unsubstituted C2 to C10 heteroaryl group).

The spiro structure may include a moiety represented by Chemical Formula 3.

[Chemical Formula 3]

  (1)

  (2)

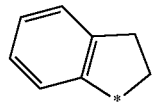  (3)

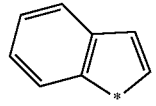  (4)

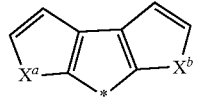  (5)

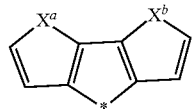  (6)

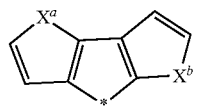  (7)

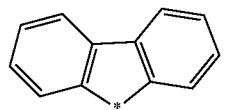  (8)

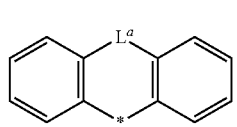  (9)

In Chemical Formula 3,

X$^a$ and X$^b$ may independently be —O—, —S—, —Se—, —Te—, —S(=O)—, —S(=O)₂—, —NR$^{a1}$—, —BR$^{a2}$—, —SiR$^b$R$^c$—, —SiR$^{bb}$R$^{cc}$—, —GeR$^d$R$^e$—, or —GeR$^{dd}$R$^{ee}$—, wherein R$^{a1}$, R$^{a2}$, R$^b$, R$^c$, R$^d$, and R$^e$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and at least one pair of R$^{bb}$ and R$^{cc}$ or R$^{dd}$ and R$^{ee}$ may be linked to each other to provide a ring structure, L$^a$ is —O—, —S—, —Se—, —Te—, —NR$^{a1}$—, —BR$^{a2}$—, —SiR$^b$R$^c$—, —GeR$^d$R$^e$—, —(CR$^f$R$^g$)$_{n1}$—, —(C(R$^p$)=N))—, or a single bond, wherein R$^{a1}$, R$^{a2}$, R$^b$, R$^c$, R$^d$, R$^e$, R$^f$, R$^g$ and R$^p$ may independently be hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and hydrogen of each ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

In Chemical Formula 3, one or more CH present in the aromatic ring of the moieties (3), (4), (5), (6) and (7) may be replaced by N.

In Chemical Formula 1, $Ar^3$ may be represented by Chemical Formula 4.

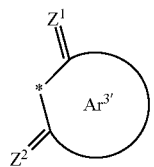

[Chemical Formula 4]

In Chemical Formula 4, $Ar^{3'}$ is a substituted or unsubstituted C6 to C30 aryl group or a substituted or unsubstituted C3 to C30 heteroaryl group, $Z^1$ is O, S, Se, or Te, and $Z^2$ is O, S, Se, Te, or $CR^aR^b$, wherein $R^a$ and $R^b$ may independently be hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group.

In Chemical Formula 1, $Ar^3$ may be a cyclic group represented by one of Chemical Formula 5A to Chemical Formula 5F.

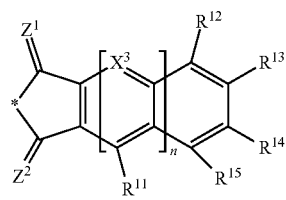

[Chemical Formula 5A]

In Chemical Formula 5A, $Z^1$ may be O, S, Se, or Te, $Z^2$ may be O, S, Se, Te, or $CR^aR^b$, wherein $R^a$ and $R^b$ may independently be hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $Z^3$ may be N or $CR^c$, wherein $R^c$ is hydrogen, deuterium, or a substituted or unsubstituted C1 to C10 alkyl group, $R^{11}$, $R^{12}$, $R^{13}$, $R^{14}$, and $R^{15}$ may be the same or different and may independently be hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof wherein $R^{12}$ and $R^{13}$ and $R^{14}$ and $R^{15}$ may independently be present or are linked to each other to provide a fused aromatic ring, n may be 0 or 1, and

* may be a linking point.

In an embodiment, at least one of $CR^{11}$, $CR^{12}$, $CR^{13}$, $CR^{14}$, and $CR^{15}$ in Chemical Formula 5A may be replaced with nitrogen (N). That is, the substituted or unsubstituted benzene ring moiety of Chemical Formula 5A may include a hetero atom (N).

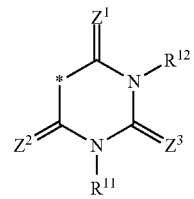

[Chemical Formula 5B]

In Chemical Formula 5B, $Z^1$ may be O, S, Se, or Te, $Z^2$ may be O, S, Se, Te, or $CR^aR^b$, wherein $R^a$ and $R^b$ may independently be hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $Z^3$ may be O, S, Se, Te, or $C(R^a)(CN)$, wherein $R^a$ is hydrogen, a cyano group (—CN), or a C1 to C10 alkyl group, $R^{11}$ and $R^{12}$ may independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* may be a linking point.

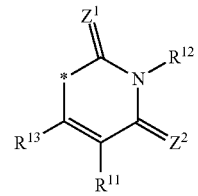

[Chemical Formula 5C]

In Chemical Formula 5C, $Z^1$ may be O, S, Se, or Te, $Z^2$ may be O, S, Se, Te, or $CR^aR^b$, wherein $R^a$ and $R^b$ may independently be hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group, $R^{11}$, $R^{12}$, and $R^{13}$ may be the same or different and may independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group (—CN), or a combination thereof, and

* may be a linking point.

[Chemical Formula 5D]

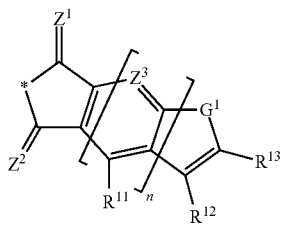

In Chemical Formula 5D,
$Z^1$ may be O, S, Se, or Te,
$Z^2$ may be O, S, Se, Te, or $CR^aR^b$, wherein $R^a$ and $R^b$ may independently be hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group,
$Z^3$ may be N or $CR^c$, wherein $R^c$ may be hydrogen or a substituted or unsubstituted C1 to C10 alkyl group,
$G^1$ may be O, S, Se, Te, $SiR^xR^y$, or $GeR^zR^w$, wherein $R^x$, $R^y$, $R^z$, and $R^w$ are the same or different and may independently be hydrogen, deuterium, a halogen, a substituted or unsubstituted C1 to C20 alkyl group, or a substituted or unsubstituted C6 to C20 aryl group,
$R^{11}$, $R^{12}$, and $R^{13}$ may be the same or different and may independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof, wherein $R^{12}$ and $R^{13}$ may independently be present or are linked to each other to provide a fused aromatic ring,
n may be 0 or 1, and
* may be a linking point.

[Chemical Formula 5E]

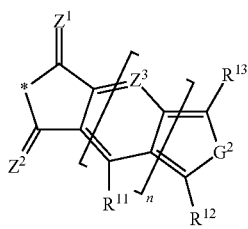

In Chemical Formula 5E,
$Z^1$ may be O, S, Se, or Te,
$Z^2$ may be O, S, Se, Te, or $CR^aR^b$, wherein $R^a$ and $R^b$ may independently be hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group,
$Z^3$ may be N or $CR^c$, wherein $R^c$ may be hydrogen or a substituted or unsubstituted C1 to C10 alkyl group,
$G^2$ may be O, S, Se, Te, $SiR^xR^y$, or $GeR^zR^w$, wherein $R^x$, $R^y$, $R^z$, and $R^w$ are the same or different and may independently be hydrogen, deuterium, a halogen, a substituted or unsubstituted C1 to C20 alkyl group, or a substituted or unsubstituted C6 to C20 aryl group,
$R^{11}$, $R^{12}$, and $R^{13}$ may be the same or different and may independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof,
n may be 0 or 1, and
* may be a linking point.

[Chemical Formula 5F]

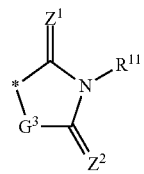

In Chemical Formula 5F,
$Z^1$ may be O, S, Se, or Te,
$Z^2$ may be O, S, Se, Te, or $CR^aR^b$, wherein $R^a$ and $R^b$ may independently be hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group,
$R^{11}$ may be hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, and
$G^3$ may be O, S, Se, Te, $SiR^xR^y$, or $GeR^zR^w$, wherein $R^x$, $R^y$, $R^z$, and $R^w$ are the same or different and may independently be hydrogen, deuterium, a halogen, a substituted or unsubstituted C1 to C20 alkyl group, or a substituted or unsubstituted C6 to C20 aryl group.

The cyclic group represented by Chemical Formula 5A may be a cyclic group represented by Chemical Formula 5A-1 or Chemical Formula 5A-2.

[Chemical Formula 5A-1]

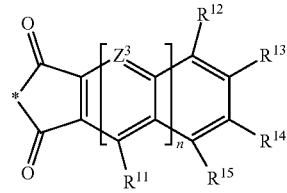

[Chemical Formula 5A-2]

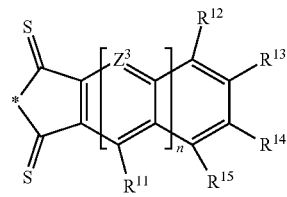

In Chemical Formula 5A-1 and Chemical Formula 5A-2, $Z^3$, n, $R^{11}$, $R^{12}$, $R^{13}$, $R^{14}$, and $R^{15}$ are the same as in Chemical Formula 5A.

The cyclic group represented by Chemical Formula 5A may be a cyclic group represented by Chemical Formula 5A-3 when $R^{12}$ and $R^{13}$ and/or $R^{14}$ and $R^{15}$ are each independently linked to form a fused aromatic ring.

[Chemical Formula 5A-3]

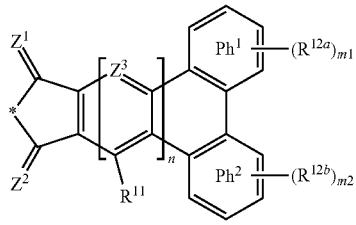

In Chemical Formula 5A-3, $Z^1$, $Z^2$, $Z^3$, $R^{11}$, and n are the same as in Chemical Formula 5A, $R^{12a}$ and $R^{12b}$ may independently be hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, or a combination thereof, m1 and m2 may independently be an integer ranging from 0 to 4, $Ph^1$ and $Ph^2$ refer to a fused benzene ring, and one of $Ph^1$ and $Ph^2$ may be optionally omitted.

The cyclic group represented by Chemical Formula 5B may be, for example, a cyclic group represented by Chemical Formula 5B-1, 5B-2, or 5B-3.

[Chemical Formula 5B-1]

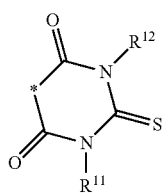

[Chemical Formula 5B-2]

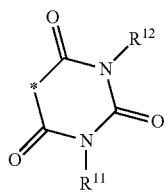

[Chemical Fomula 5B-3]

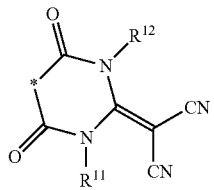

In Chemical Formula 5B-1, 5B-2 and 5B-3, $R^{11}$ and $R^{12}$ are the same as in Chemical Formula 5B.

The cyclic group represented by Chemical Formula 5C may be, for example, a cyclic group represented by Chemical Formula 5C-1 or 50-2.

[Chemical Formula 5C-1]

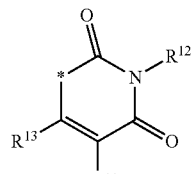

[Chemical Formula 5C-2]

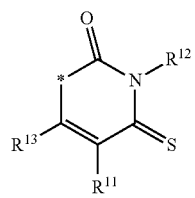

In Chemical Formula 5C-1 and 5C-2, $R^{11}$ to $R^{13}$ are the same as in Chemical Formula 5C.

In Chemical Formula 1, N of the electron donor moiety, $X^1$ of the $X^1$-containing ring, the functional groups (C=O, C=S, C=Se, or C=Te) present in $Ar^3$, which is the electron acceptor moiety increase intramolecular interactions to improve the absorption intensity at a specific wavelength.

Specific examples of the compound represented by Chemical Formula 2A may include compounds of Group 1, but are not limited thereto.

[Group 1]

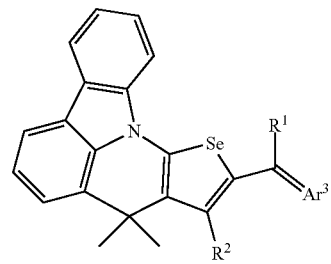

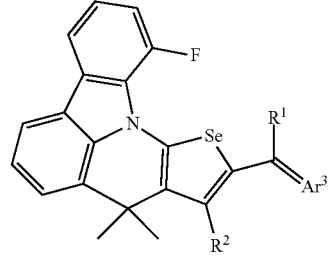

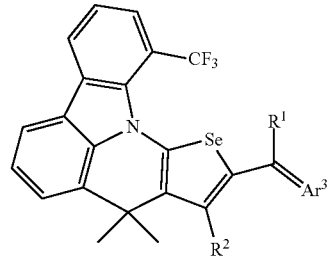

91
-continued
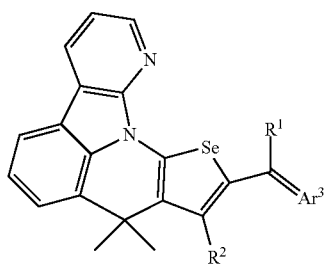
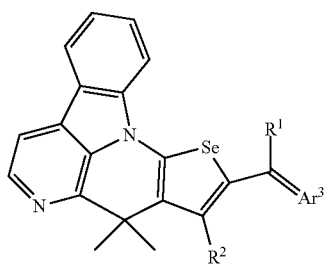
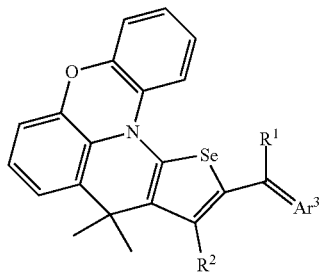
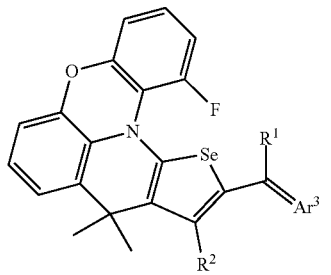
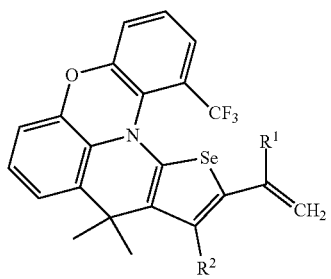
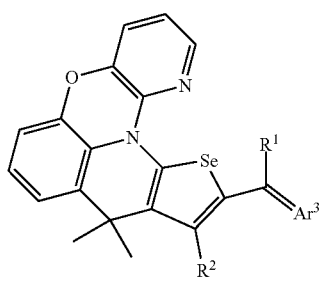
92
-continued
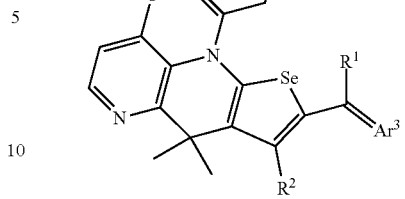
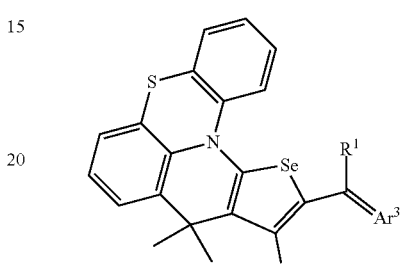
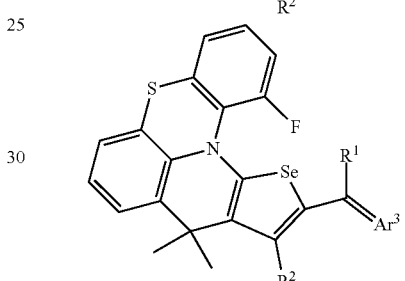
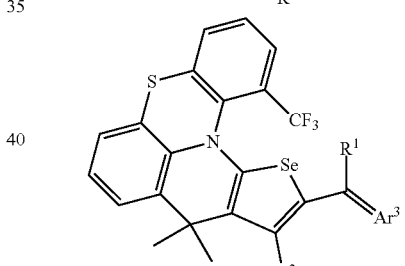
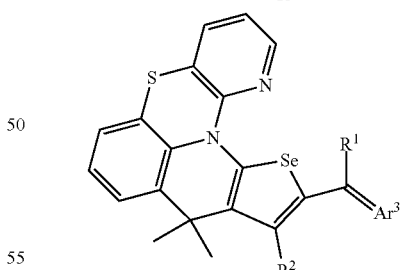
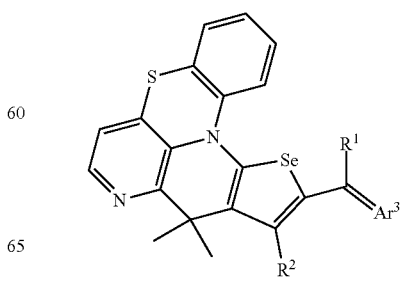

-continued
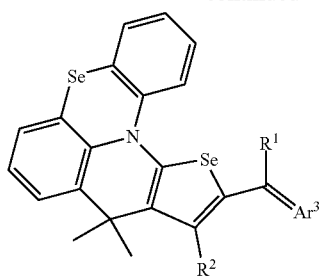
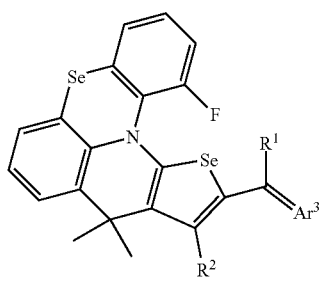
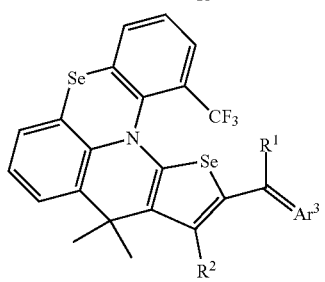
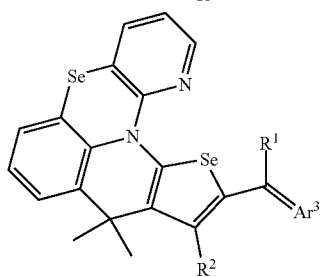
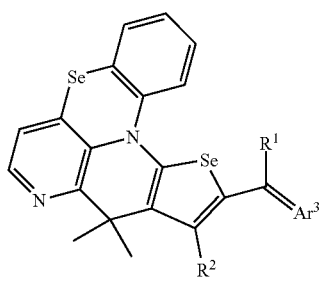
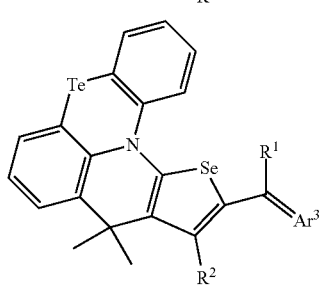
-continued
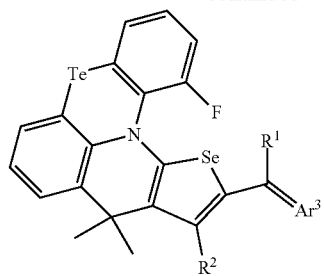
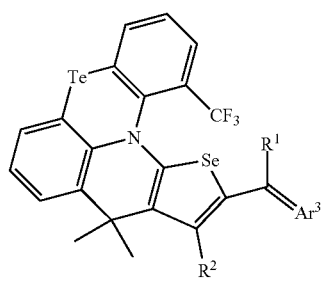
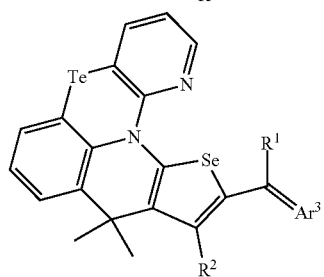
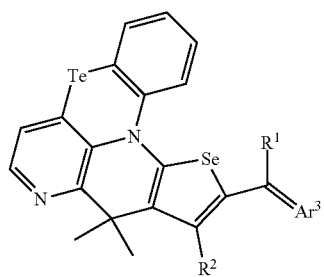
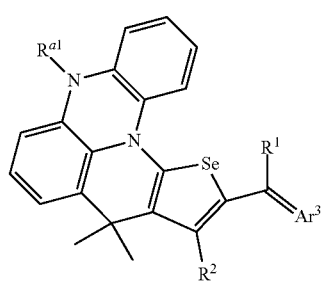
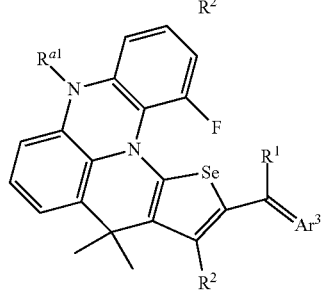

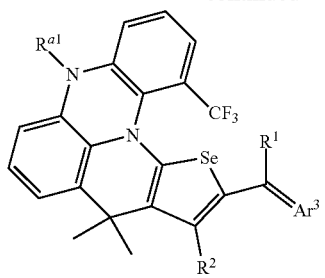
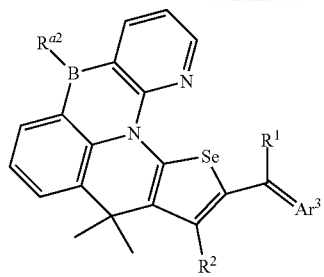
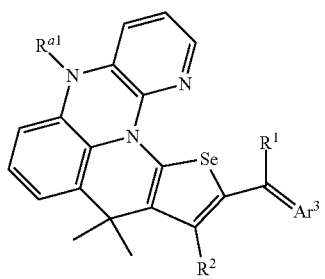
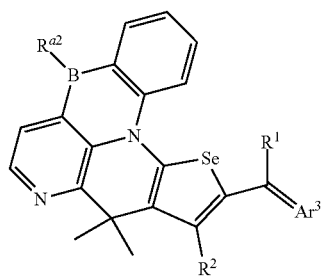
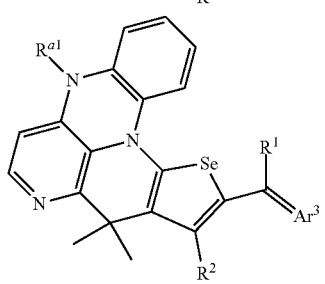
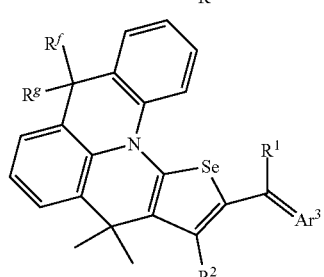
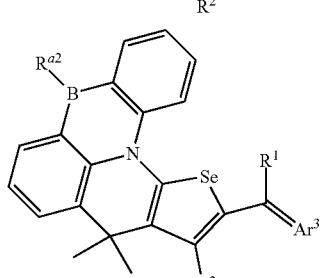
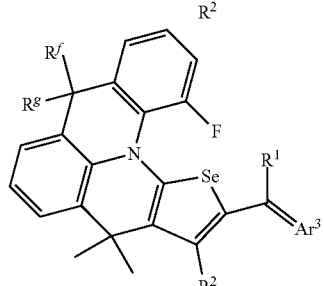
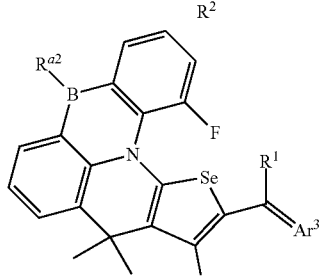
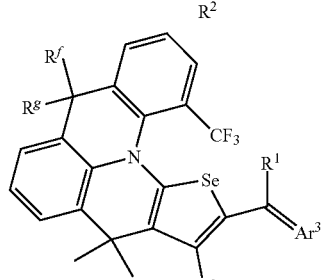
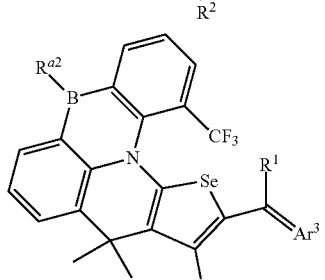
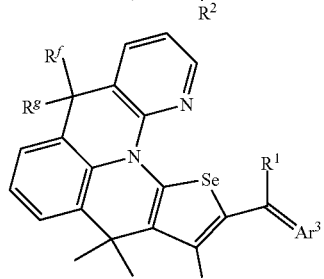

-continued
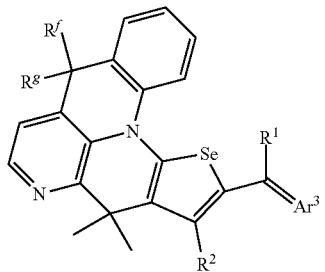
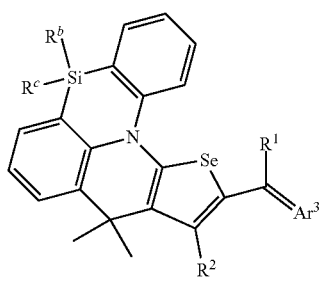
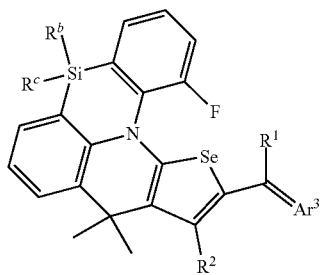
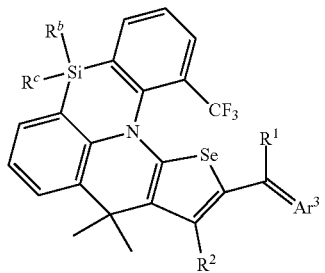
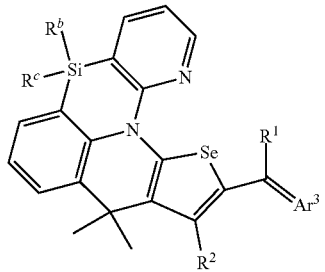
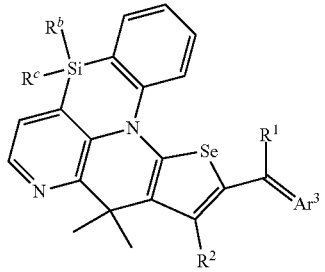
-continued
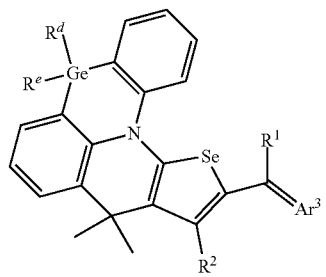
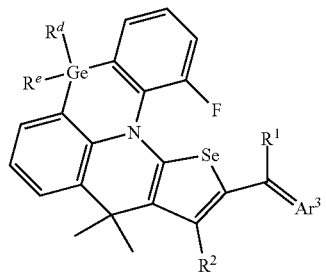
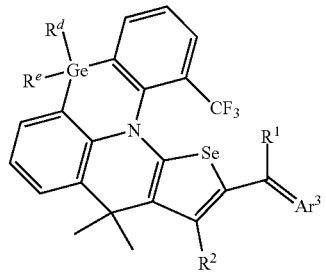
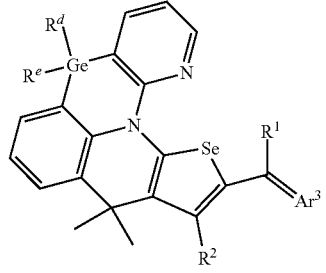
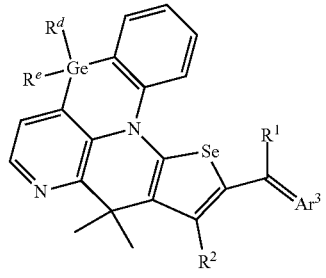
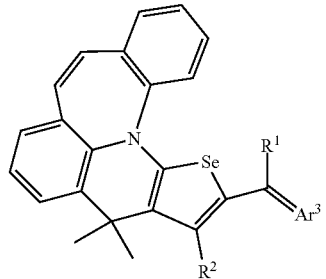

-continued
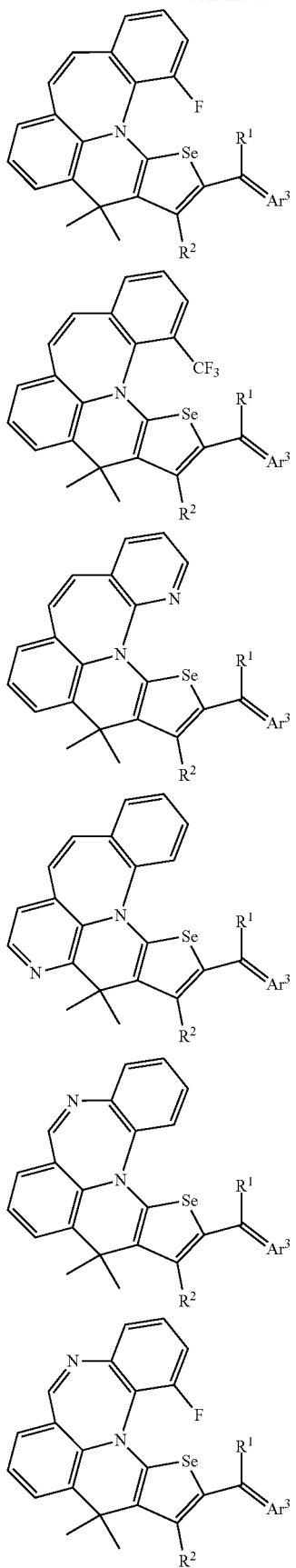
-continued
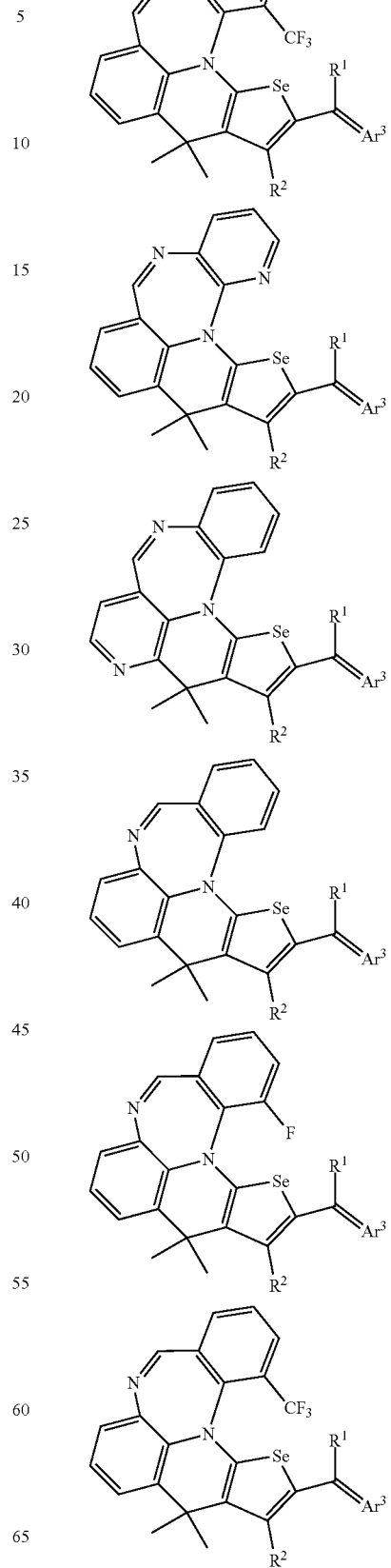

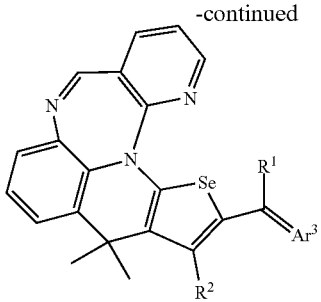

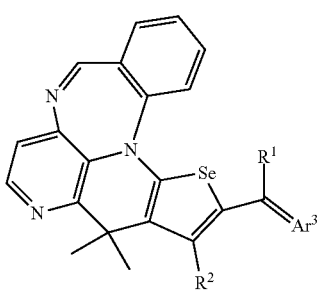

In Group 1, Ar³, R¹, and R² are the same as in Chemical Formula 1, $R^{a1}$, $R^{a2}$, $R^b$, $R^c$, $R^d$, $R^e$, $R^f$, and $R^g$ may independently be hydrogen, deuterium, a halogen, a substituted or unsubstituted C1 to C20 alkyl group, a substituted or unsubstituted C6 to C20 aryl group, or a substituted or unsubstituted C6 to C20 aryloxy group, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

In Group 1, compounds in which $X^1$ is —Se— in Chemical Formula 2A are shown, but the —Se— may be replaced by another linking group of $X^1$ (—Te—, —S(=O)—, —S(=O)$_2$—, —$NR^{a1}$—, —$BR^{a2}$—, —$SiR^bR^c$—, —$SiR^{bb}R^{cc}$—, —$GeR^dR^e$—, —$GeR^{dd}R^{ee}$—, —$CR^fR^g$—, or —$CR^{ff}R^{gg}$—).

In Group 1, compounds in which $X^2$ is —C(CH$_3$)(CH$_3$)— in Chemical Formula 2A are shown, but the —C(CH$_3$)(CH$_3$)— may be replaced by another linking group of $X^2$ (—O—, —S—, —Se—, —Te—, —S(=O)—, —S(=O)$_2$—, —$NR^{a1}$—, —$BR^{a2}$—, —$SiR^bR^c$—, —$SiR^{bb}R^{cc}$—, —$GeR^dR^e$—, —$GeR^{dd}R^{ee}$—, —$(CR^fR^g)_{n1}$—, —$(CR^{ff}R^{gg})$—, —$(C(R^m)=C(R^n))$—, —$(C(R^{mm})=C(R^{nn}))$—, or $(C(R^p)=N))$—).

Structures in which CH present in the benzene ring in Group 1 is replaced by one N are illustrated, but the CH of each ring (benzene ring, azepine, etc.) of Group 1 may be replaced by N, wherein one ring may include one or more N, and a plurality of rings may contain N.

Specific examples of the compound represented by Chemical Formula 2A-11a or Chemical Formula 2A-21a may include compounds of Group 1-1, but are not limited thereto.

[Group 1-1]

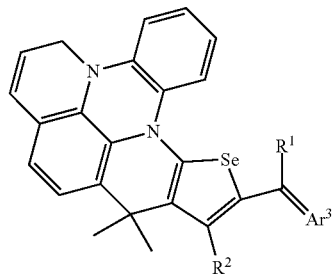

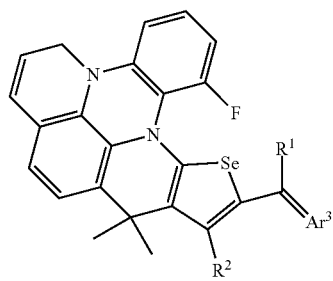

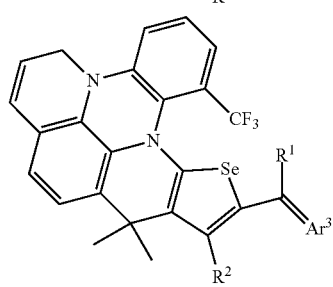

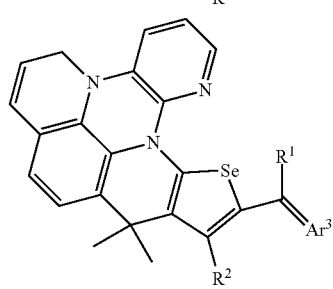

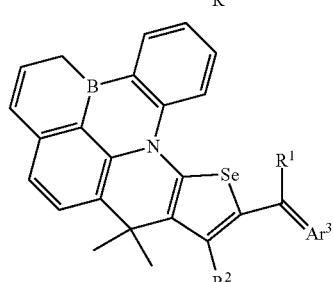

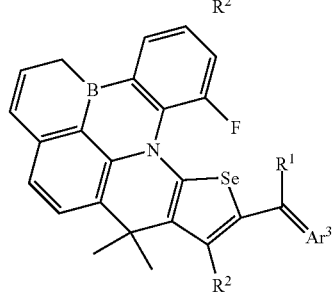

103
-continued
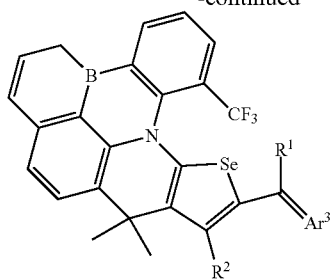
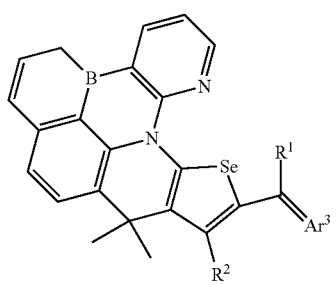
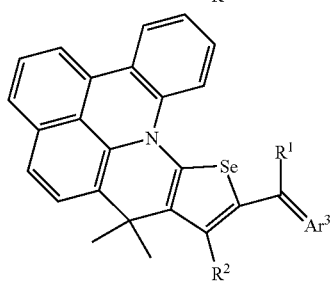
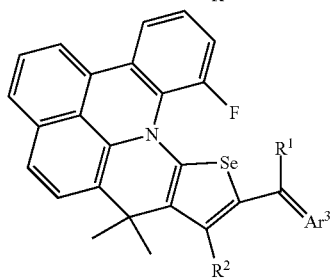
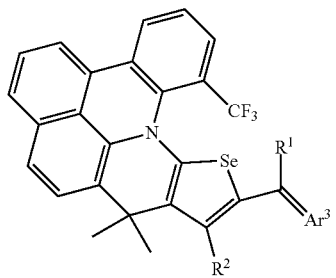
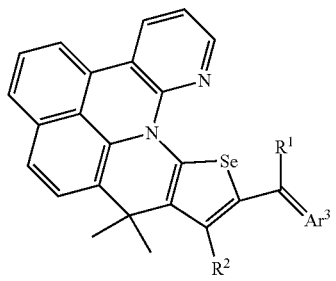
104
-continued
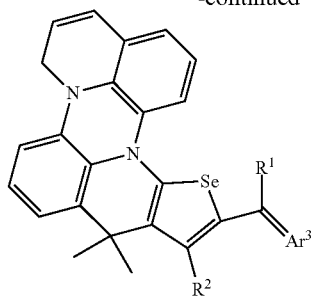
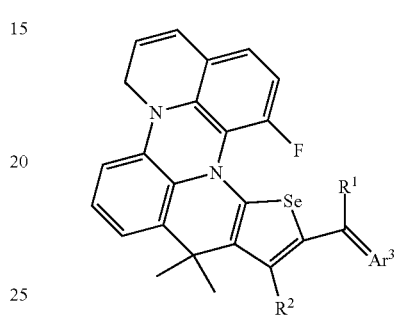
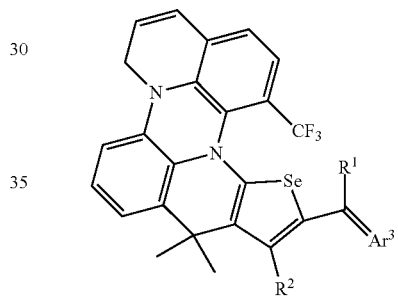
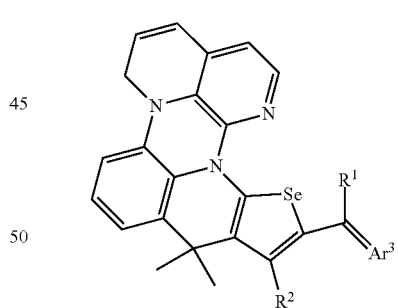
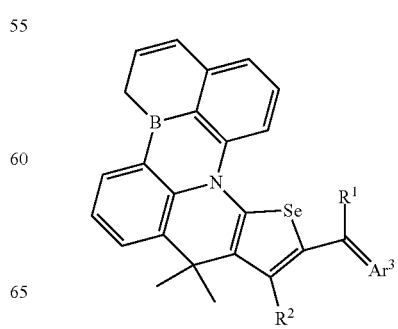

-continued

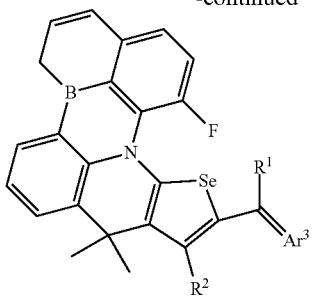

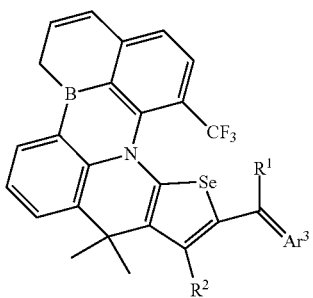

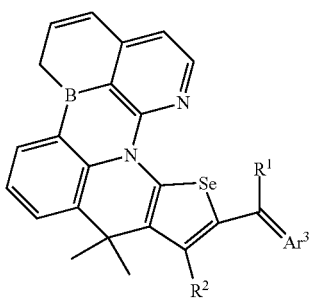

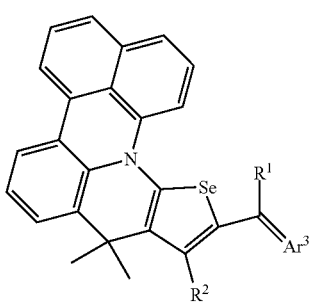

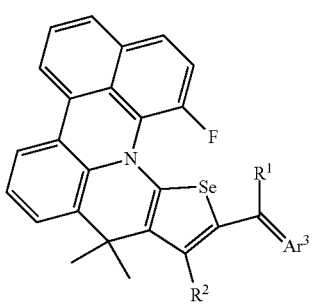

-continued

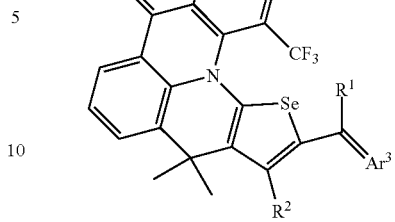

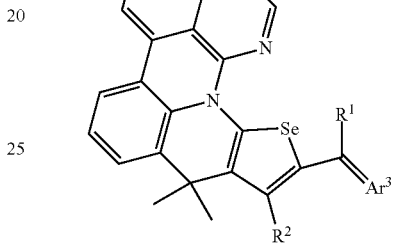

In Group 1-1, Ar³, R¹, and R² are the same as in Chemical Formula 1, hydrogen of each ring (benzene ring or cyclohexadiene ring) may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

Structures in which CH present in the benzene ring in Group 1-1 is replaced by one N are illustrated, but the CH of each ring (benzene ring or cyclohexadiene) of Group 1-1 may be replaced by N, wherein one ring may include one or more N, and a plurality of rings may contain N.

In Group 1-1, compounds in which $X^1$ is —Se— in Chemical Formula 2A-11a or Chemical Formula 2A-21a are shown, the —Se— may be replaced by another linking group of $X^1$ (—Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —CR$^f$R$^g$—, or —CR$^{ff}$R$^{gg}$—).

In Group 1-1, compounds in which $X^2$ is —(C(CH$_3$)(CH$_3$))— in Chemical Formula 2A-1 and Chemical Formula 2A-2 are shown but the —(C(CH$_3$)(CH$_3$)) may be replaced by another linking group of $X^2$ (—O—, —S—, —Se—, —Te—, —S(=O)—, —S(=O)$_2$—, —NR$^{a1}$—, —BR$^{a2}$—, —SiR$^b$R$^c$—, —SiR$^b$R$^c$—, —GeR$^d$R$^e$—, —GeR$^{dd}$R$^{ee}$—, —(CR$^f$R$^g$)$_{n1}$—, —(CR$^{ff}$R$^{gg}$)—, —(C(R$^m$)=C(R$^n$))—, —(C(R$^{mm}$)=C(R$^{nn}$))—, or —(C(R$^p$)=N))—).

Specific examples of the compound represented by Chemical Formula 2A-12 or Chemical Formula 2A-22 may include compounds of Group 1-2, but are not limited thereto.

[Group 1-2]
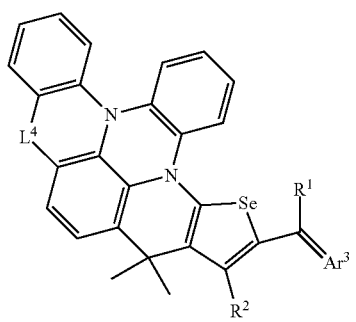
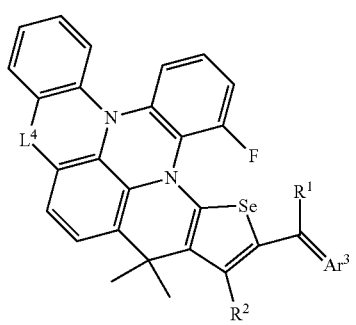
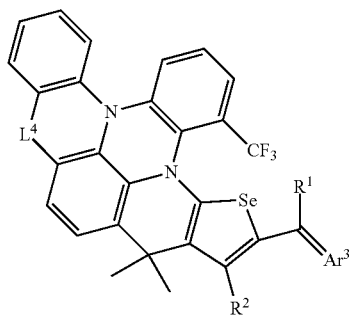
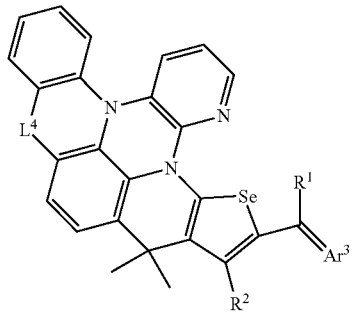
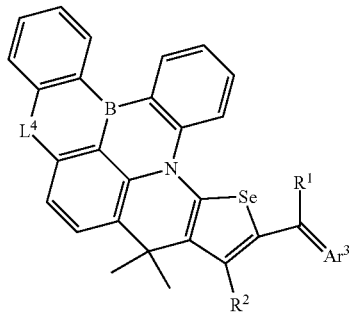
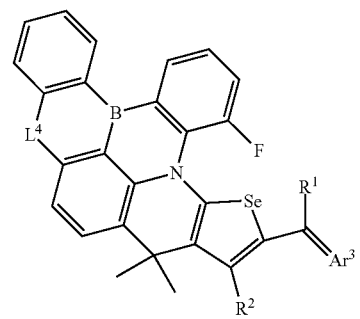
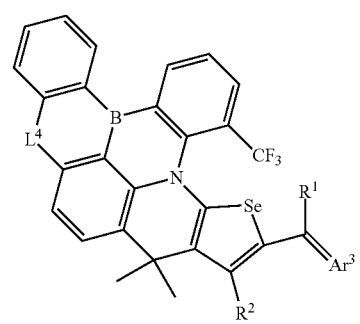
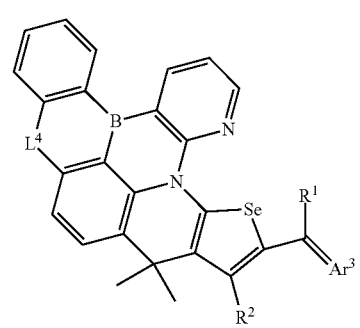
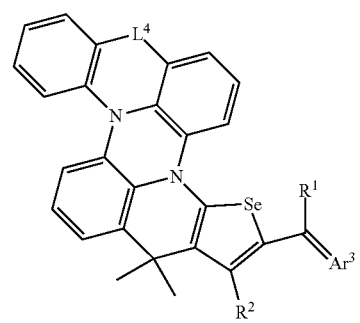
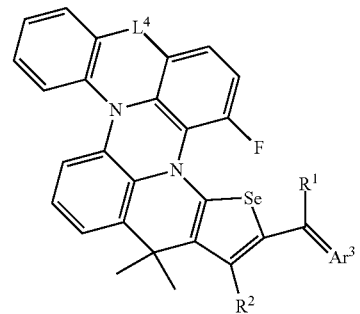

-continued

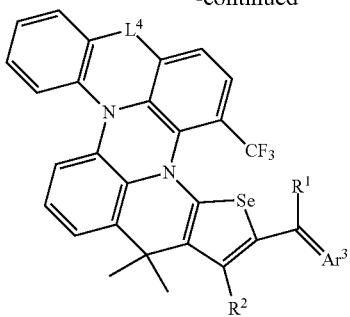
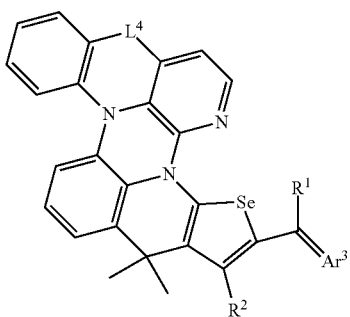
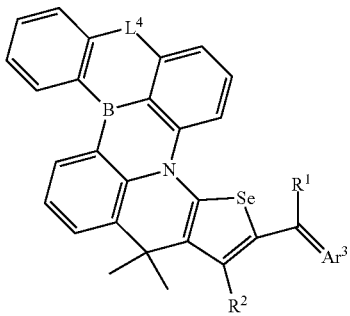
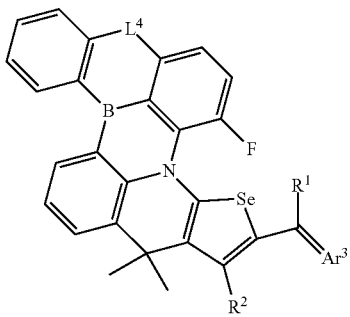
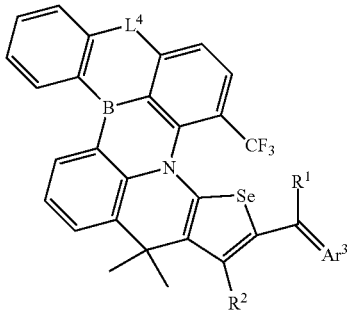

-continued

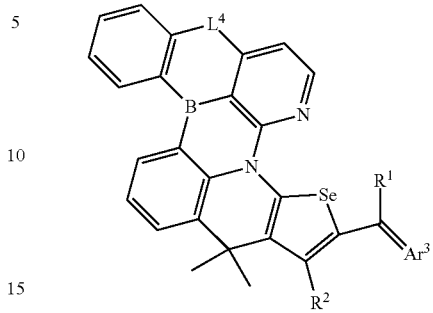

In Group 1-2, Ar³, R¹ and R² are the same as in Chemical Formula 1,

L⁴ may be —O—, —S—, —Se—, —Te—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —(CR$^f$R$^g$)$_{n1}$—, —(CR$^{ff}$R$^{gg}$)—, —(C(R$^m$)=C(R$^n$))—, —(C(R$^{mm}$)=C(R$^{nn}$))—, —(C(R$^p$)=N))—, or a single bond, wherein R$^{a1}$, R$^{a2}$, R$^b$, R$^c$, R$^d$, R$^e$, R$^f$, R$^g$, R$^m$, R$^n$, and R$^p$ may independently be hydrogen, deuterium, a halogen, a substituted or unsubstituted C1 to C20 alkyl group, or a substituted or unsubstituted C6 to C20 aryl group, at least one pair of R$^{bb}$ and R$^{cc}$, R$^{dd}$ and R$^{ee}$, R$^{ff}$ and R$^{gg}$, or R$^{mm}$ and R$^{nn}$ is linked with each other to provide a ring structure, and n1 of —(CR$^f$R$^g$)$_{n1}$— is 1 or 2, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

Structures in which CH present in the ring in Group 2 is replaced by one N are illustrated, the CH of each ring (e.g., benzene ring) of Group 1-2 may be replaced by N, wherein one ring may include one or more N, and a plurality of rings may contain N.

In Group 1-2, compounds in which X¹ is —Se— in Chemical Formula 2A-12 or Chemical Formula 2A-22 are shown, but the —Se— may be replaced by another linking group of X¹ (—Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —CR$^f$R$^g$—, or —CR$^{ff}$R$^{gg}$—).

In Group 1-2, compounds in which X² is —C(CH$_3$)(CH$_3$))— in Chemical Formula 2A-12 or Chemical Formula 2A-22 are shown, but the —C(CH$_3$)(CH$_3$))— may be replaced by another linking group of X² (—O—, —S—, —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —(CR$^f$R$^g$)$_{n1}$—, —(CR$^{ff}$R$^{gg}$)—, —(C(R$^m$)=C(R$^n$))—, —(C(R$^{mm}$)=C(R$^{nn}$))—, or —(C(R$^p$)=N))—).

Specific examples of the compound represented by Chemical Formula 2A may include compounds of Group 1a, but is not limited thereto.

[Group 1a]
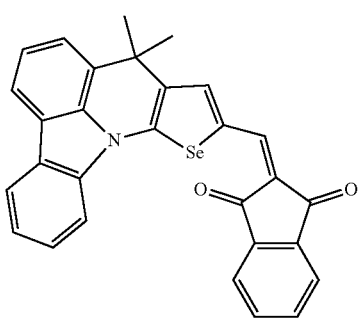
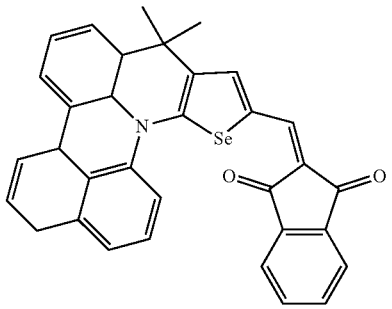
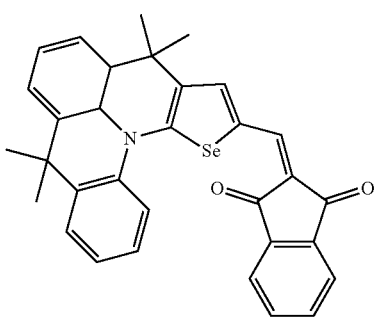
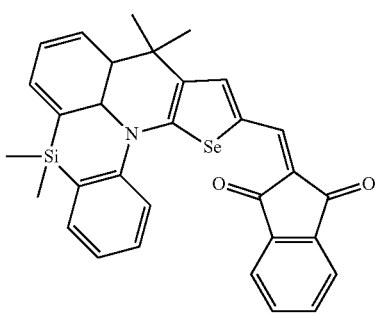
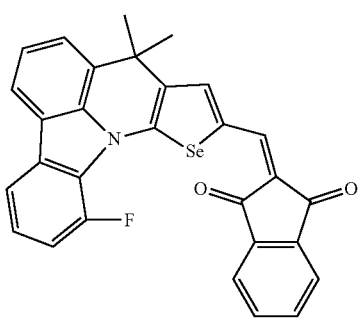
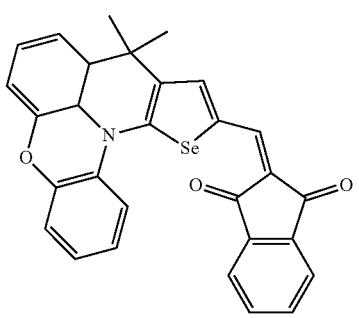
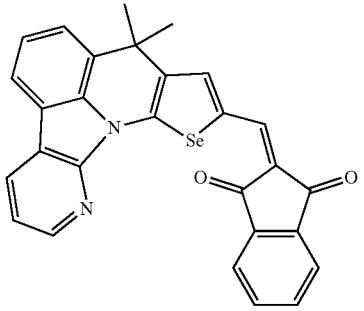
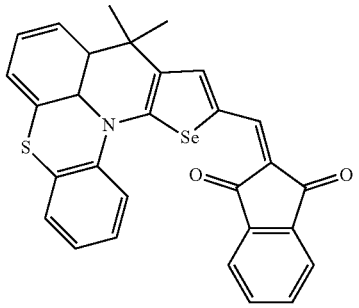
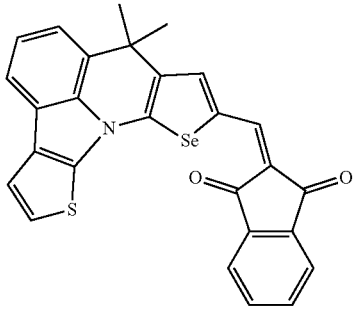
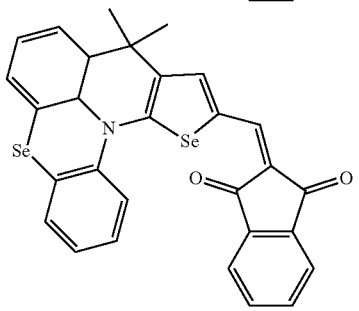

113
-continued
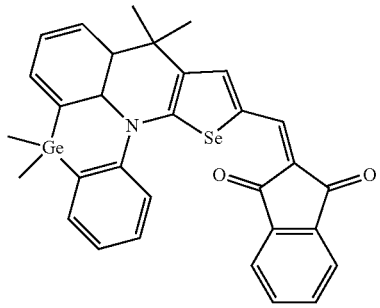
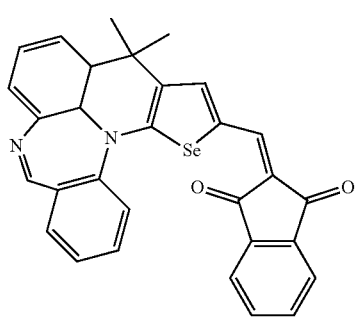
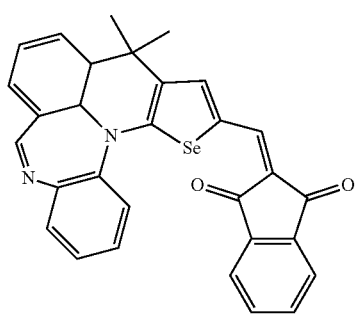
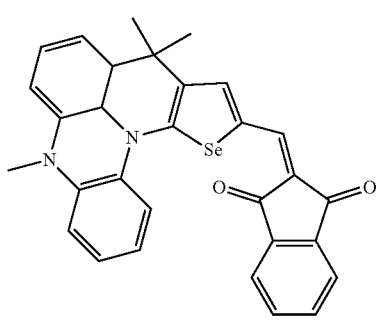
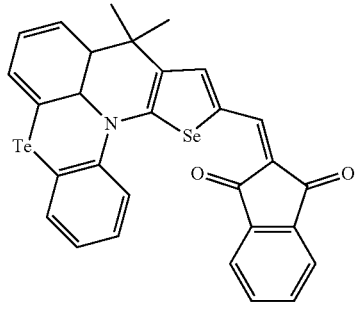
114
-continued
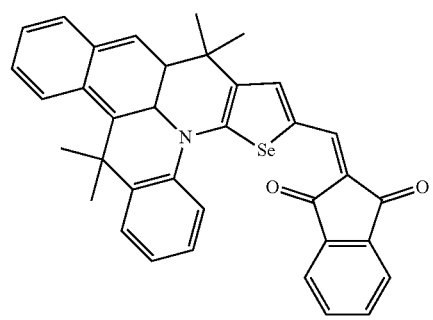
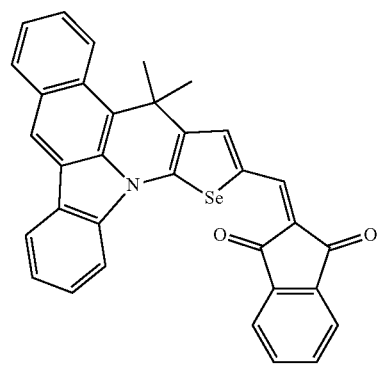
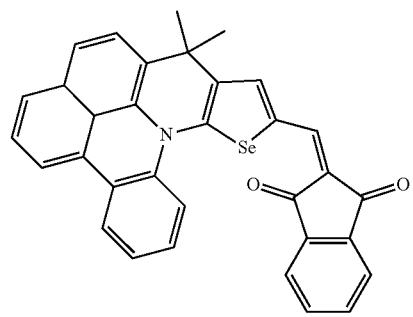
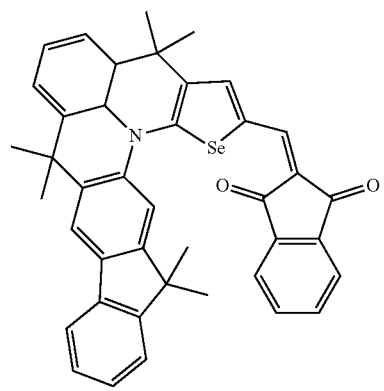
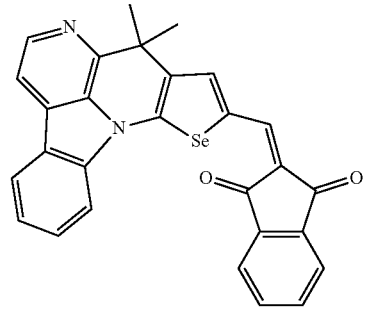

115
-continued
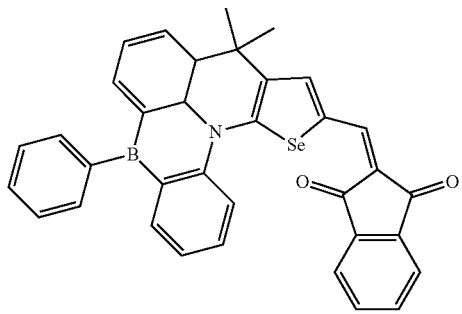
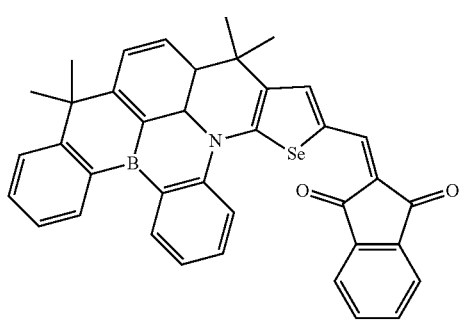
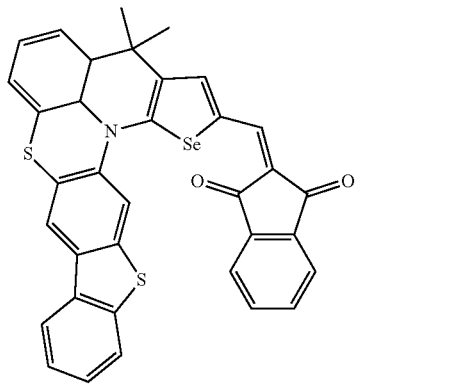
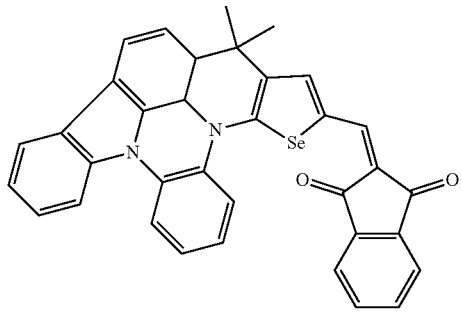
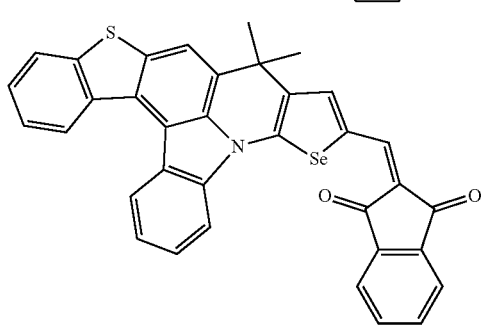
116
-continued
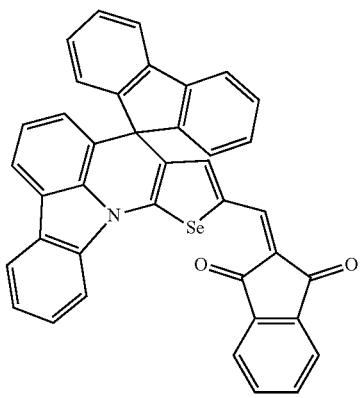
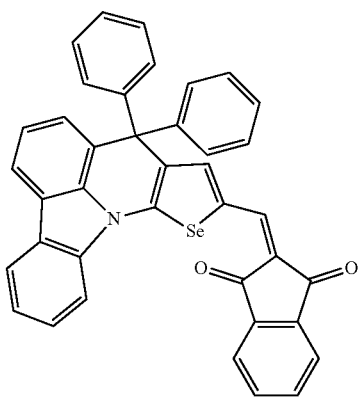
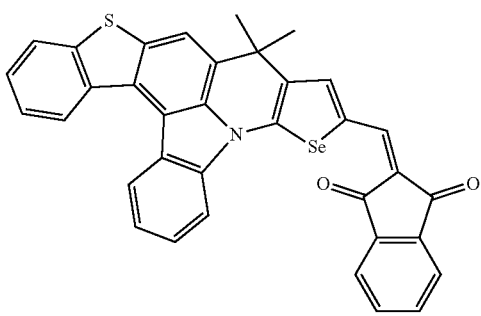
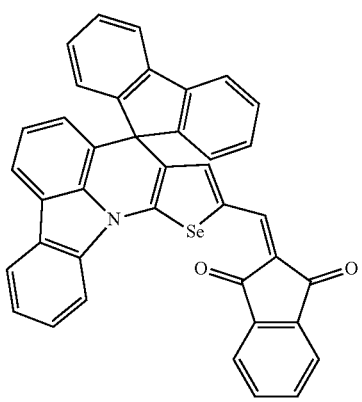

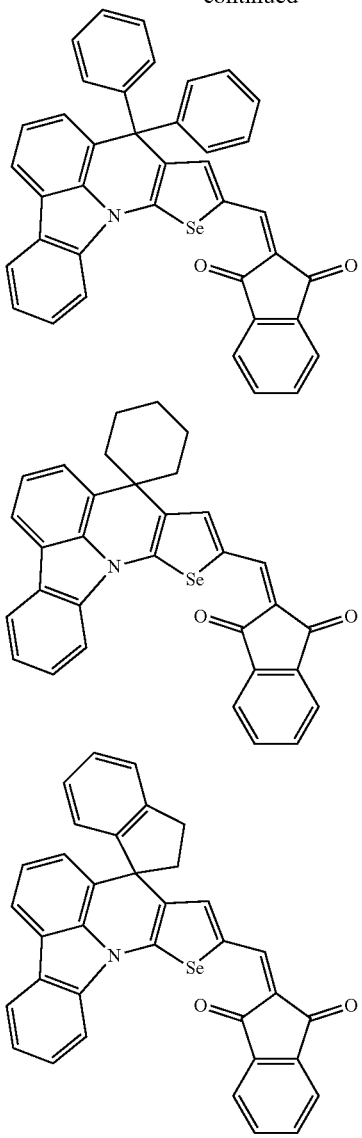

In Group 1a,
hydrogen of each aromatic ring may be replaced by at least one substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and a combination thereof.

In Group 1a, the functional groups belonging to the cyclic group represented by Chemical Formula 5A as the acceptor structure are illustrated, but the case of any one of Chemical Formulas 5B to 5F may be illustrated in the same manner.

Group 1, Group 1-1, Group 1-2, and Group 1a may be examples of the compound represented by Chemical Formula 2A, but compounds represented by Chemical Formula 2B to Chemical Formula 2E may also be provided by the same manner.

For example, a specific example of the compound represented by Formula 2E may be provided by the compound of Group 2, but is not limited thereto.

[Group 2]

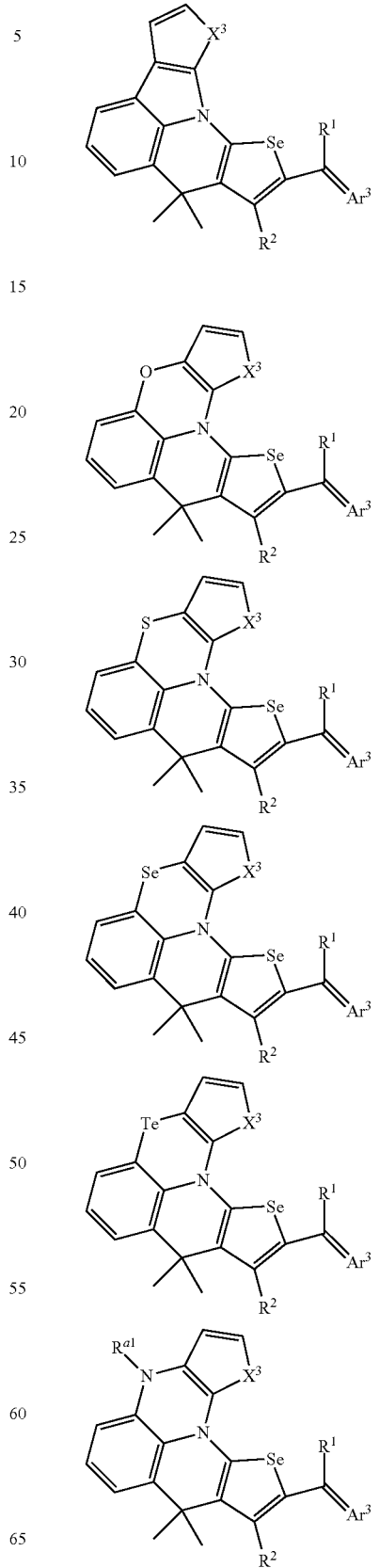

-continued
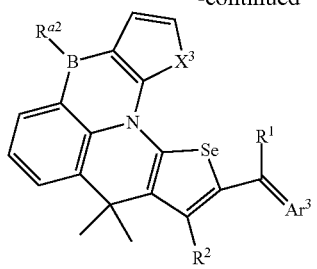
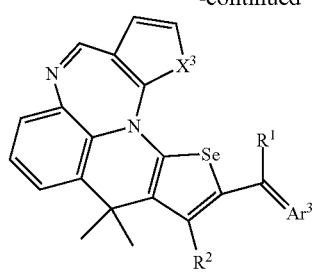
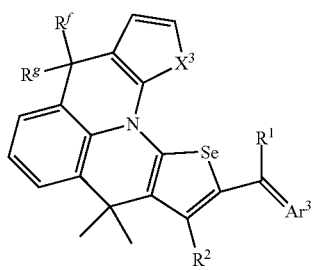
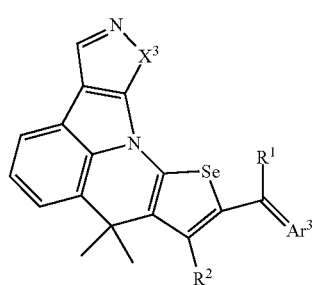
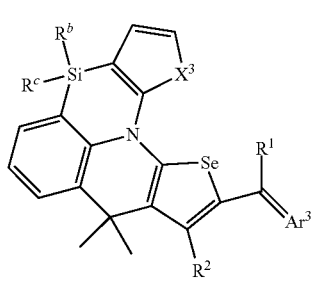
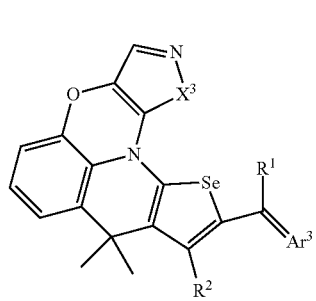
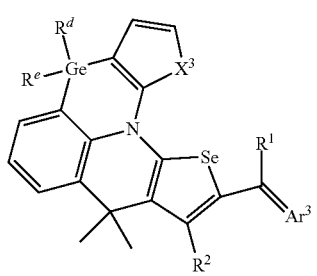
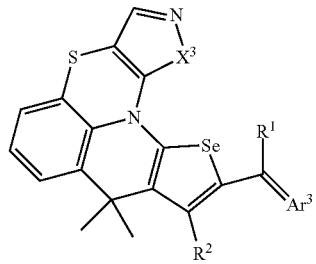
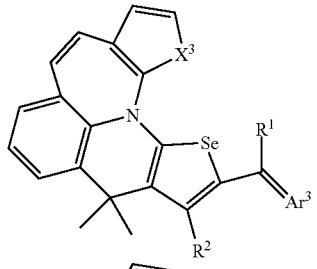
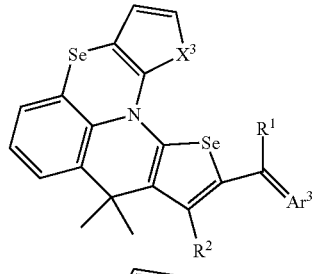
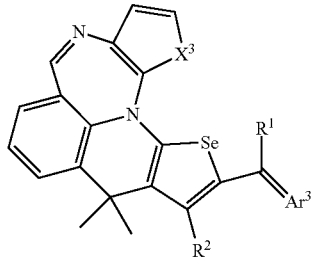
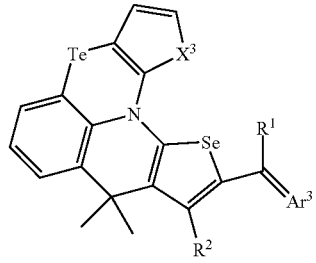

-continued
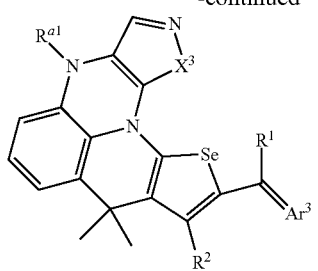
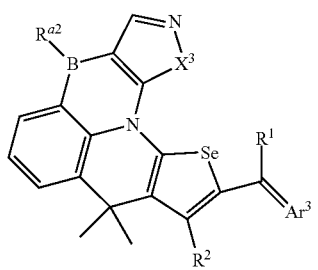
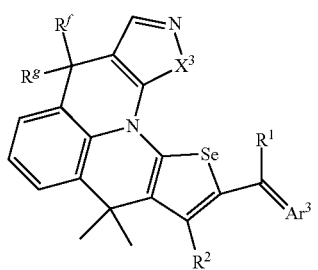
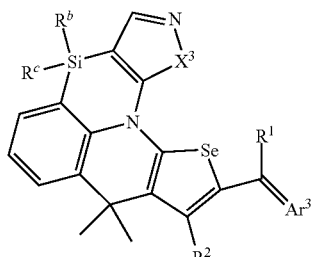
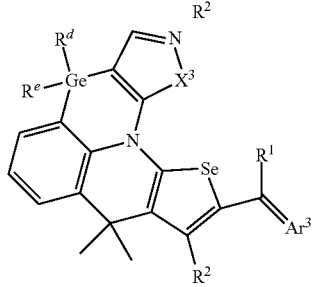
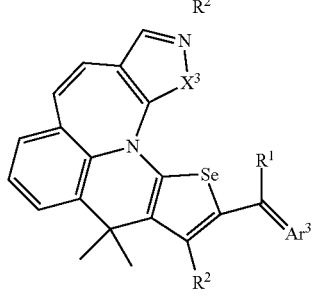
-continued
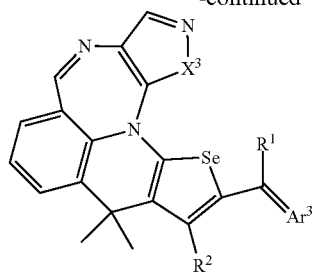
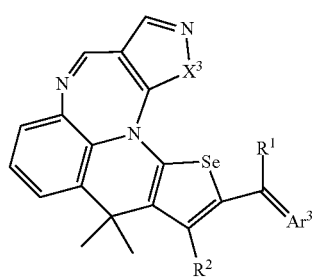
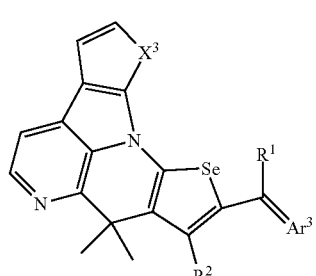
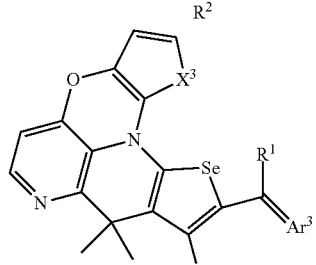
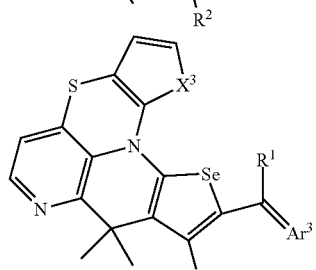
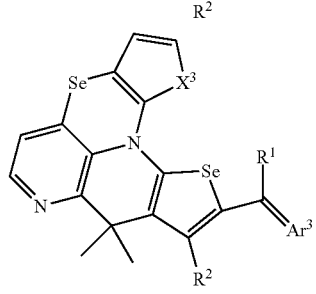

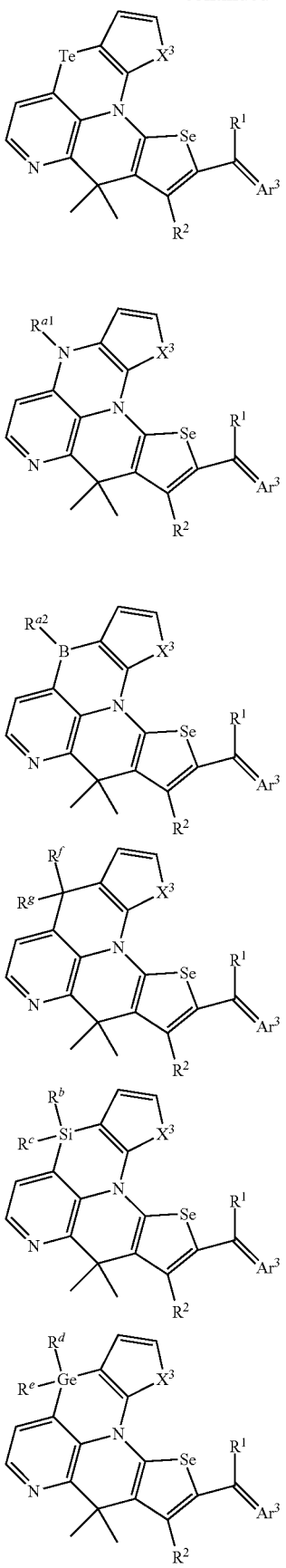

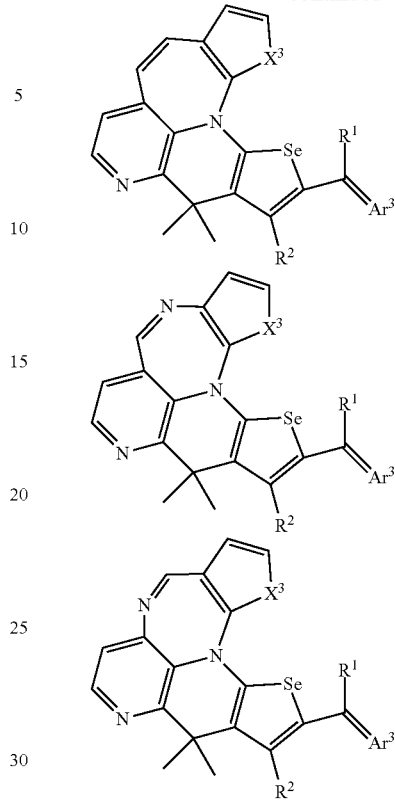

In Group 2, Ar³, R¹ and R² are the same as in Chemical Formula 1,

X³ is the same as in Chemical Formula 2E, $R^{a1}$, $R^{a2}$, $R^b$, $R^c$, $R^d$, $R^e$, $R^f$, and $R^g$ may independently be hydrogen, deuterium, a halogen, a substituted or unsubstituted C1 to C20 alkyl group, a substituted or unsubstituted C6 to C20 aryl group, or a substituted or unsubstituted C6 to C20 aryloxy group, and hydrogen of each aromatic ring may be replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

In Group 2, compounds in which $X^1$ is —Se— in Chemical Formula 2E are shown, the —Se— may be replaced by another linking group of $X^1$ (—Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —CR$^f$R$^g$—, or —CR$^{ff}$R$^{gg}$—).

In Group 2, compounds in which $X^2$ is —C(CH$_3$)(CH$_3$)— in Chemical Formula 2E are shown, but the —C(CH$_3$)(CH$_3$)— may be replaced by another linking group of $X^2$ (—O—, —S—, —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —(CR$^f$R$^g$)$_{n1}$—, —(CR$^{ff}$R$^{gg}$)—, —(C(R$^m$)=C(R$^n$))—, —(C(R$^{mm}$)=C(R$^{nn}$))—, or (C(R$^p$)=N))—).

Structures in which CH present in the benzene ring in Group 2 is replaced by one N are illustrated, but the CH of each ring (benzene ring, azepine, etc.) of Group 2 may be replaced by N, wherein one ring may include one or more N, and a plurality of rings may contain N.

The compound is a compound selectively absorbing light in a green wavelength region and may have a maximum absorption wavelength (Amax) in a wavelength region of greater than or equal to about 500 nm, for example greater than or equal to about 510 nm, greater than or equal to about greater than or equal to 520 nm, greater than or equal to 525 nm, or greater than or equal to 530 nm and less than or equal to about 600 nm, for example less than or equal to about 590 nm, less than or equal to about 580 nm, less than or equal to about 570 nm, less than or equal to about 560 nm, less than or equal to about 555 nm, or less than or equal to about 550 nm.

The compound may exhibit a light absorption curve having a full width at half maximum (FWHM) of about 50 nm to about 110 nm, for example about 50 nm to about 100 nm, in a thin film state. Herein, the FWHM is a width of a wavelength corresponding to half of a height of a maximum absorption point. When the full width at half maximum (FWHM) is small, wavelength selectivity is increased by selectively absorbing light in a narrow wavelength region. As used herein, when specific definition is not otherwise provided, it may be defined by absorbance measured by UV-Vis spectroscopy. When the full width at half maximum (FWHM) is within the range, selectivity in a green wavelength region may be increased. The thin film may be a thin film deposited under a vacuum condition.

The compound may be formed into a thin film by using a deposition method. The deposition method may provide a uniform thin film and have small inclusion possibility of impurities into the thin film, but when the compound has a lower melting point than a temperature for the deposition, a product decomposed from the compound may be deposited and thus performance of a device may be deteriorated. Accordingly, the compound desirably has a higher melting point than the deposition temperature. The compound has, for example, at least about 10° C., for example at least about 20° C., or at least about 30° C. higher melting point than the deposition temperature and thus may be desirably used for the deposition.

In more detail, the donor-acceptor type material represented by Chemical Formula 1 may be thermally decomposed at the melting point ($T_m$) of the material because the melting point ($T_m$) is similar to the decomposition temperature ($T_d$). Accordingly, if the temperature (sublimation temperature, deposition temperature, $T_s$) at which a film is formed by vacuum deposition is higher than $T_m$, decomposition occurs more preferentially than sublimation (deposition), and thus a normal device cannot be manufactured. Since it is impossible to produce a stable image sensor with these materials, $T_m$ should be higher than $T_s$, and desirably $T_m - T_s \geq 10°$ C.

In addition, a micro lens array (MLA) needs to be formed to concentrate light after manufacturing an organic photoelectric device during manufacture of an image sensor. Formation of this micro lens array requires a relatively high temperature (greater than or equal to about 160° C., for example greater than or equal to about 170° C., greater than or equal to about 180° C., or greater than or equal to about 190° C.). The performance of the photoelectric devices (e.g., organic photoelectric devices) is required not to be deteriorated in these heat-treatment processes. The performance deterioration of the organic photoelectric device during the heat treatment of MLA may be caused not by chemical decomposition of an organic material but its morphology change. The morphology change is in general caused, when a material starts a thermal vibration due to a heat treatment, but a material having a firm molecule structure may not have the thermal vibration and be limited and/or prevented from the deterioration by the heat treatment. The compound may be suppressed from the thermal vibration of molecules due to a conjugation structure in the donor moiety and thus may be stably maintained during the MLA heat treatment and secure process stability.

The compound may be a p-type semiconductor compound.

Since the compound works as a p-type semiconductor, the compound may be appropriately used, as long as it has a higher LUMO level than an n-type semiconductor. The energy level is expressed as an absolute value from a vacuum level. For example, when the compound is mixed with an n-type material such as fullerene, the compound desirably has a higher LUMO level than the fullerene having a LUMO level of 4.2 eV. As for the appropriate HOMO-LUMO level of the compound, when the compound has a HOMO level ranging from about 5.2 eV to about 5.8 eV, and an energy bandgap ranging from about 2.12 eV to about 2.48 eV, the LUMO level of the compound is in a range of about 3.8 eV to about 2.7 eV. The compound having a HOMO level, an LUMO level, and an energy bandgap within the ranges may be used as a p-type semiconductor compound effectively absorbing light in a green wavelength region, and thus has high external quantum efficiency (EQE) and resultantly improves photoelectric conversion efficiency.

In example embodiments, in view of a thin film formation, a stably depositable compound is desirable and thus the compound has a molecular weight of about 300 g/mol to about 1500 g/mol. However, even though the compound has a molecular weight out of the range, a depositable compound may be used without limitation. In addition, when the compound is formed to form a thin film using a coating process, a compound that is dissolved in a solvent and coated may be used without limitation.

Hereinafter, a photoelectric device including the compound according to an embodiment is described with reference to drawings.

FIG. 1 is a cross-sectional view showing a photoelectric device according to an embodiment.

Referring to FIG. 1, a photoelectric device 100 according to an example embodiment includes a first electrode 10 and a second electrode 20, and an active layer 30 between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor such as indium tin oxide (ITO) or indium zinc oxide (IZO), or a metal thin layer of a thin single layer or multilayer. When one of the first electrode 10 and the second electrode 20 is a non-light-transmitting electrode, it may be made of, for example, an opaque conductor such as aluminum (Al).

The active layer 30 includes a p-type semiconductor and an n-type semiconductor to form a pn junction, and absorbs external light to generate excitons and then separates the generated excitons into holes and electrons.

The active layer 30 includes the compound represented by Chemical Formula 1. The compound may act as a p-type semiconductor compound in the active layer 30.

The compound is a compound selectively absorbing light in a green wavelength region, and the active layer 30 including the compound may have a maximum absorption wavelength ($\lambda_{max}$) in a wavelength region of greater than or equal to about 500 nm, for example greater than or equal to about 510 nm, greater than or equal to about 520 nm, greater than or equal to about 525 nm, greater than or equal to about 530 nm, or greater than or equal to about 535 nm and less than or equal to about 590 nm, for example less than or equal to about 580 nm, less than or equal to about 570 nm, or less than or equal to about 560 nm.

The active layer 30 may exhibit a light absorption curve having a relatively narrow full width at half maximum (FWHM) of about 50 nm to about 110 nm, for example about 50 nm to about 100 nm. Accordingly, the active layer 30 has high selectivity for light in a green wavelength region.

The active layer may have an absorption coefficient of greater than or equal to about $6.0 \times 10^4$ cm$^{-1}$, for example about $6.7 \times 10^4$ cm$^{-1}$ to about $10 \times 10^4$ cm$^{-1}$ or about $6.9 \times 10^4$ cm$^{-1}$ to about $10 \times 10^4$ cm$^{-1}$ when including the compound Chemical Formula 1 and C60 in a volume ratio of about 0.9:1 to about 1.1:1, for example about 1:1.

The active layer 30 may further include an n-type semiconductor compound for forming a pn junction.

The n-type semiconductor compound may be sub-phthalocyanine or a sub-phthalocyanine derivative, fullerene or a fullerene derivative, thiophene or a thiophene derivative, or a combination thereof.

The fullerene may include C60, C70, C76, C78, C80, C82, C84, C90, C96, C240, C540, a mixture thereof, a fullerene nanotube, and the like. The fullerene derivative may refer to compounds of these fullerenes having a substituent. The fullerene derivative may include a substituent such as an alkyl group (e.g., C1 to C30 alkyl group), an aryl group (e.g., C6 to C30 aryl group), a heterocyclic group (e.g., C3 to C30 heterocycloalkyl group), and the like. Examples of the aryl groups and heterocyclic groups may be are a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a benzimidazole ring, an imidazopyridine ring, a quinolizidine ring, a quinoline ring, a phthalazine ring, a naphthyridine ring, a quinoxaline ring, a quinazoline ring, an isoquinoline ring, a carbazole ring, a phenanthridine ring, an acridine ring, a phenanthroline ring, a thianthrene ring, a chromene ring, an xanthene ring, a phenoxazine ring, a phenoxathin ring, a phenothiazine ring, or a phenazine ring.

The sub-phthalocyanine or the sub-phthalocyanine derivative may be represented by Chemical Formula 6.

[Chemical Formula 6]

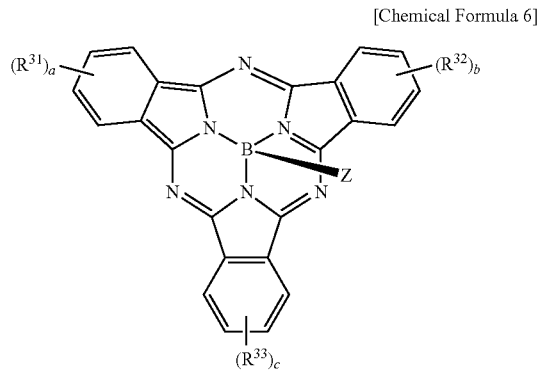

In Chemical Formula 6,
R$^{31}$ to R$^{33}$ may independently be hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a halogen-containing group, or a combination thereof,
a, b, and c are integers ranging from 1 to 3, and
Z is a monovalent substituent.

For example, Z may be a halogen or a halogen-containing group, for example F, Cl, an F-containing group, or a Cl-containing group.

The halogen refers to F, Cl, Br, or I and the halogen-containing group refers to alkyl group (C1 to C30 alkyl group) where at least one of hydrogen is replaced by F, Cl, Br, or I.

The thiophene derivative may be for example represented by Chemical Formula 7 or 8, but is not limited thereto.

[Chemical Formula 7]

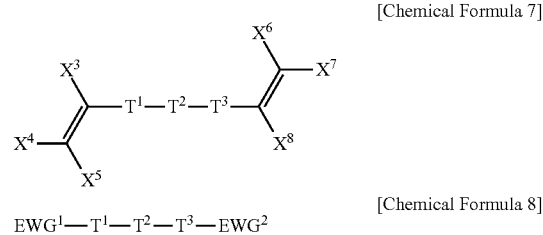

[Chemical Formula 8]

EWG$^1$—T$^1$—T$^2$—T$^3$—EWG$^2$

In Chemical Formulas 7 and 8,
T$^1$, T$^2$, and T$^3$ are aromatic rings including substituted or unsubstituted thiophene moieties,
T$^1$, T$^2$, and T$^3$ are each independently present or are fused to each other,
X$^3$ to X$^8$ are each independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a cyano group, or a combination thereof, and
EWG$^1$ and EWG$^2$ are each independently electron withdrawing groups.

For example, in Chemical Formula 7, at least one of X$^3$ to X$^8$ may be an electron withdrawing group, for example a cyano-containing group.

The active layer 30 may further include a second p-type semiconductor compound selectively absorbing green light. The second p-type semiconductor compound may be a compound represented by Chemical Formula 9.

[Chemical Formula 9]

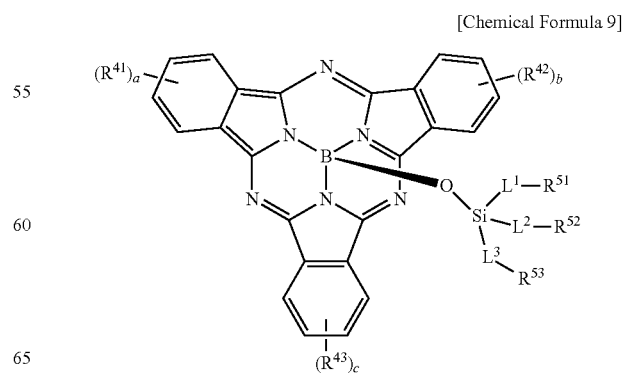

In Chemical Formula 9, $R^{41}$ to $R^{43}$ are each independently hydrogen, a substituted or unsubstituted C1 to C30 aliphatic hydrocarbon group, a substituted or unsubstituted C6 to C30 aromatic hydrocarbon group, a substituted or unsubstituted C1 to C30 aliphatic heterocyclic group, a substituted or unsubstituted C2 to C30 aromatic heterocyclic group, a substituted or unsubstituted C1 to C30 alkoxy group, a substituted or unsubstituted C6 to C30 aryloxy group, a thiol group, a substituted or unsubstituted C1 to C30 alkylthio group, a substituted or unsubstituted C6 to C30 arylthio group, a cyano group, a cyano-containing group, a halogen, a halogen-containing group, a substituted or unsubstituted sulfonyl group (e.g., a substituted or unsubstituted C0 to C30 aminosulfonyl group, a substituted or unsubstituted C1 to C30 alkylsulfonyl group or a substituted or unsubstituted C6 to C30 arylsulfonyl group), or a combination thereof, or two adjacent groups of $R^{41}$ to $R^{43}$ are linked with each other to provide a fused ring, $L^1$ to $L^3$ may independently be a single bond, a substituted or unsubstituted C1 to C30 alkylene group, a substituted or unsubstituted C6 to C30 arylene group, divalent substituted or unsubstituted C3 to C30 heterocyclic group, or a combination thereof, $R^{51}$ to $R^{53}$ may independently be a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted C1 to C30 alkoxy group, a substituted or unsubstituted amine group (e.g., a substituted or unsubstituted C1 to C30 alkylamine group or a substituted or unsubstituted C6 to C30 arylamine group), a substituted or unsubstituted silyl group, or a combination thereof, and a to c may independently be an integer ranging from 0 to 4.

The second p-type semiconductor compound selectively absorbing green light may be included in an amount of about 500 to about 1500 parts by weight based on 100 parts by weight of the compound represented by Chemical Formula 1.

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, and the like.

The intrinsic layer (I layer) may include the compound of Chemical Formula 1 and the n-type semiconductor compound in a volume ratio of about 1:100 to about 100:1. The compound of Chemical Formula 1 and the n-type semiconductor compound may be included in a volume ratio ranging from about 1:50 to about 50:1 within the range, specifically, about 1:10 to about 10:1, and more specifically, about 1:1. When the compound of Chemical Formula 1 and the n-type semiconductor compound have a composition ratio within the range, an exciton may be effectively produced, and a pn junction may be effectively formed.

The p-type layer may include the semiconductor compound of Chemical Formula 1, and the n-type layer may include the n-type semiconductor compound.

The active layer 30 may have a thickness of about 1 nm to about 500 nm and specifically, about 5 nm to about 300 nm. When the active layer 30 has a thickness within the range, the active layer may effectively absorb light, effectively separate holes from electrons, and deliver them, thereby effectively improving photoelectric conversion efficiency. A desirable thickness of the active layer 30 may be, for example, determined by an absorption coefficient of the active layer 30, and may be, for example, a thickness being capable of absorbing light of at least about 70% or more, for example about 80% or more, and for another example about 90% or more.

In the photoelectric device 100, when light enters from the first electrode 10 and/or second electrode 20, and when the active layer 30 absorbs light in a desired and/or alternatively predetermined wavelength region, excitons may be produced from the inside. The excitons are separated into holes and electrons in the active layer 30, and the separated holes are transported to an anode that is one of the first electrode 10 and the second electrode 20 and the separated electrons are transported to the cathode that is the other of and the first electrode 10 and the second electrode 20 so as to flow a current in the photoelectric device.

Hereinafter, a photoelectric device according to another embodiment is described with reference to FIG. 2.

Figure 2:
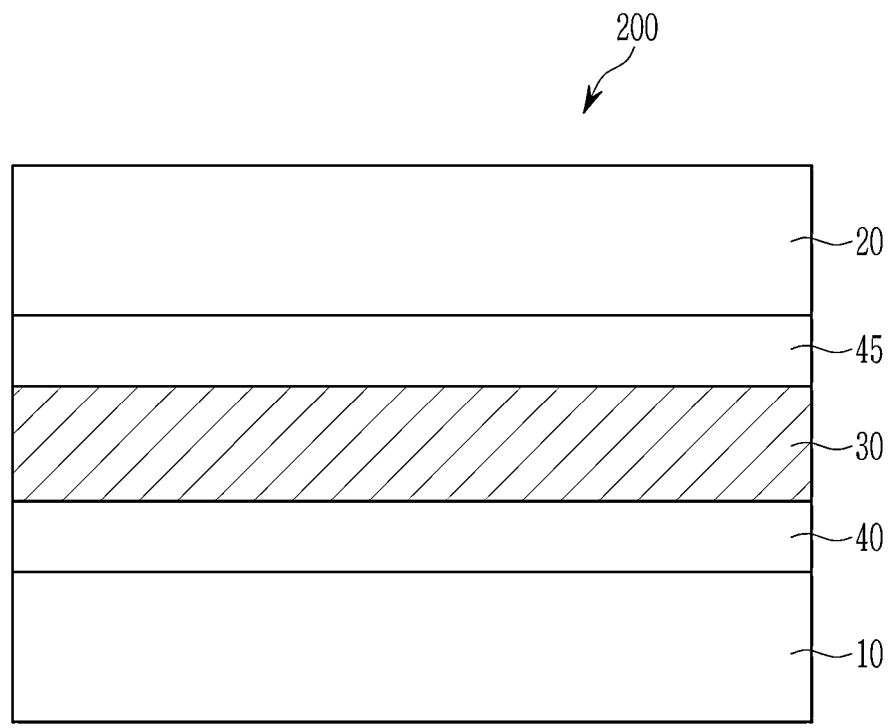
FIG. 2 is a cross-sectional view showing a photoelectric device according to another embodiment.

FIG. 2 is a cross-sectional view showing a photoelectric device according to another example embodiment.

Referring to FIG. 2, a photoelectric device 200 according to the present embodiment includes a first electrode 10 and a second electrode 20 facing each other, and an active layer 30 between the first electrode 10 and the second electrode 20, like the above embodiment.

However, the photoelectric device 200 according to the present embodiment further includes charge auxiliary layers 40 and 45 between the first electrode 10 and the active layer 30, and the second electrode 20 and the active layer 30, unlike the above embodiment. The charge auxiliary layers 40 and 45 may facilitate the transfer of holes and electrons separated from the active layer 30, so as to increase efficiency.

The charge auxiliary layers 40 and 45 may be at least one selected from a hole injection layer (HIL) for facilitating hole injection, a hole transport layer (HTL) for facilitating hole transport, an electron blocking layer (EBL) for preventing electron transport, an electron injection layer (EIL) for facilitating electron injection, an electron transport layer (ETL) for facilitating electron transport, and a hole blocking layer (HBL) for preventing hole transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide such as molybdenum oxide, tungsten oxide, nickel oxide, and the like.

The hole transport layer (HTL) may include one selected from, for example, poly(3,4-ethylenedioxythiophene):poly (styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, Alq$_3$, Gaq$_3$, Inq$_3$, Znq$_2$, Zn(BTZ)$_2$, BeBq$_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, Alq$_3$, Gaq$_3$, Inq$_3$, Znq$_2$, Zn(BTZ)$_2$, BeBq$_2$, and a combination thereof, but is not limited thereto.

Either one of the charge auxiliary layers 40 and 45 may be omitted.

The photoelectric device may be applied to various fields, for example a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
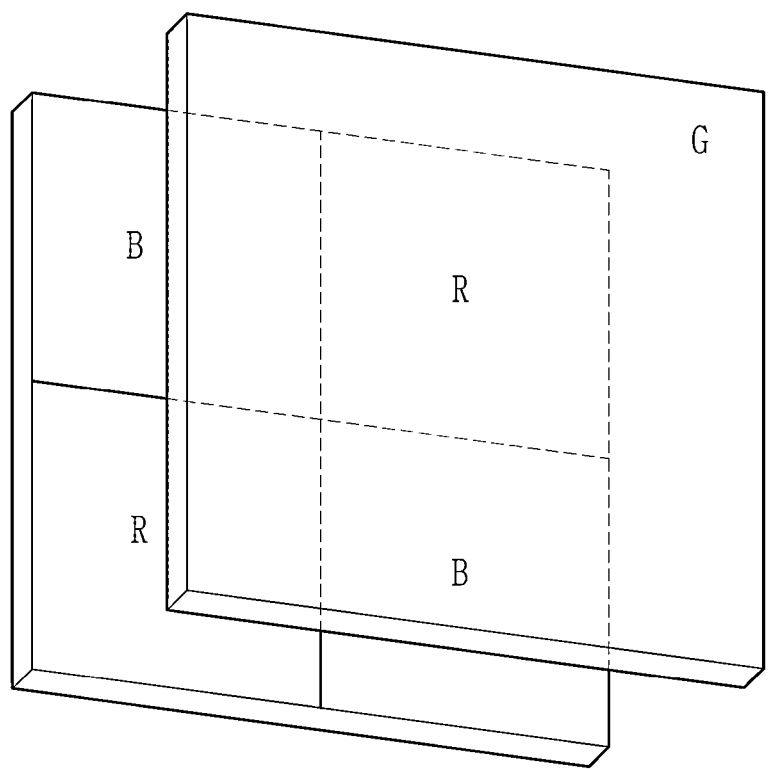
FIG. 3 is a schematic plan view showing an organic CMOS image sensor according to an embodiment.
Figure 4:
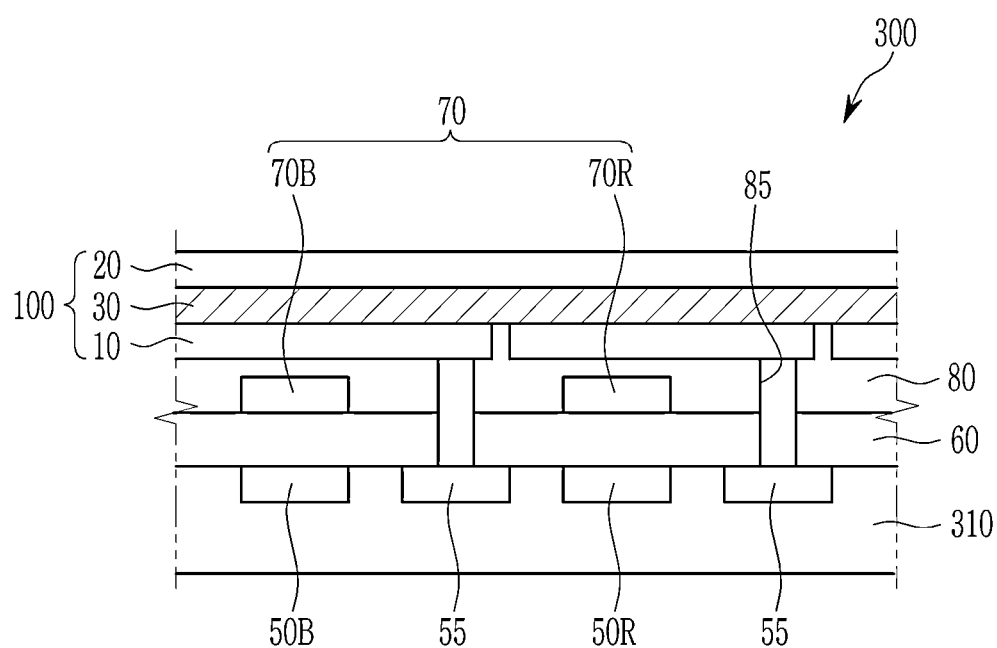
FIG. 4 is a cross-sectional view of the organic CMOS image sensor of FIG. 3.

FIG. 3 is a schematic top plan view showing an organic CMOS image sensor according to an example embodiment, and FIG. 4 is a cross-sectional view showing the organic CMOS image sensor of FIG. 3.

Referring to FIGS. 3 and 4, an organic CMOS image sensor 300 according to an example embodiment includes a semiconductor substrate 310 integrated with photo-sensing devices 50B and 50R, a transmission transistor (not shown), a charge storage 55, a lower insulation layer 60, a color filter layer 70, an upper insulation layer 80, and a photoelectric device 100.

The semiconductor, substrate 310 may be a silicon substrate, and is integrated with the photo-sensing devices 50B and 50R, the transmission transistor (not shown), and the charge storage 55. The photo-sensing devices 50R and 50B may be photodiodes.

The photo-sensing devices 50B and 50R, the transmission transistor, and/or the charge storage 55 may be integrated in each pixel, and as shown in the drawing, the photo-sensing devices 50B and 50R may be respectively included in a blue pixel and a red pixel and the charge storage 55 may be included in a green pixel.

The photo-sensing devices 50B and 50R sense light, the information sensed by the photo-sensing devices may be transferred by the transmission transistor, the charge storage 55 is electrically connected to the photoelectric device 100, and the information of the charge storage 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 310. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70B formed in the blue pixel and selectively transmitting blue light and a red filter 70R formed in the red pixel and selectively transmitting red light. In an embodiment, a cyan filter and a yellow filter may be disposed instead of the blue filter 70B and red filter 70R. In the present embodiment, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 eliminates a step caused by the color filter layer 70 and smoothens the surface. The upper insulation layer 80 and the lower insulation layer 60 may include a contact hole (not shown) exposing a pad, and a through-hole 85 exposing the charge storage 55 of the green pixel.

The aforementioned photoelectric device 100 is formed on the upper insulation layer 80. The photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs and/or senses light in a green wavelength region and replaces a color filter of a green pixel.

When light enters from the second electrode 20, the light in a green wavelength region may be mainly absorbed in the active layer 30 and photoelectrically converted, while the light in the rest of the wavelength regions passes through first electrode 10 and may be sensed in the photo-sensing devices 50B and 50R.

As described above, the photoelectric devices selectively absorbing light in a green wavelength region are stacked and thereby a size of an image sensor may be decreased and a down-sized image sensor may be realized.

As described above, the compound represented by the Chemical Formula 1 may be used as a semiconductor compound, aggregation between compounds in a thin film state is inhibited, and thereby light absorption characteristics depending on a wavelength may be maintained. Thereby, green wavelength selectivity may be maintained, crosstalk caused by unnecessary absorption of other light except a green wavelength region may be decreased and sensitivity may be increased.

In an embodiment, in FIG. 4, additional color filters may be further disposed on the photoelectric device 100. The additional color filters may include a blue filter 70B and a red filter 70R or a cyan filter and a yellow filter.

Figure 5:
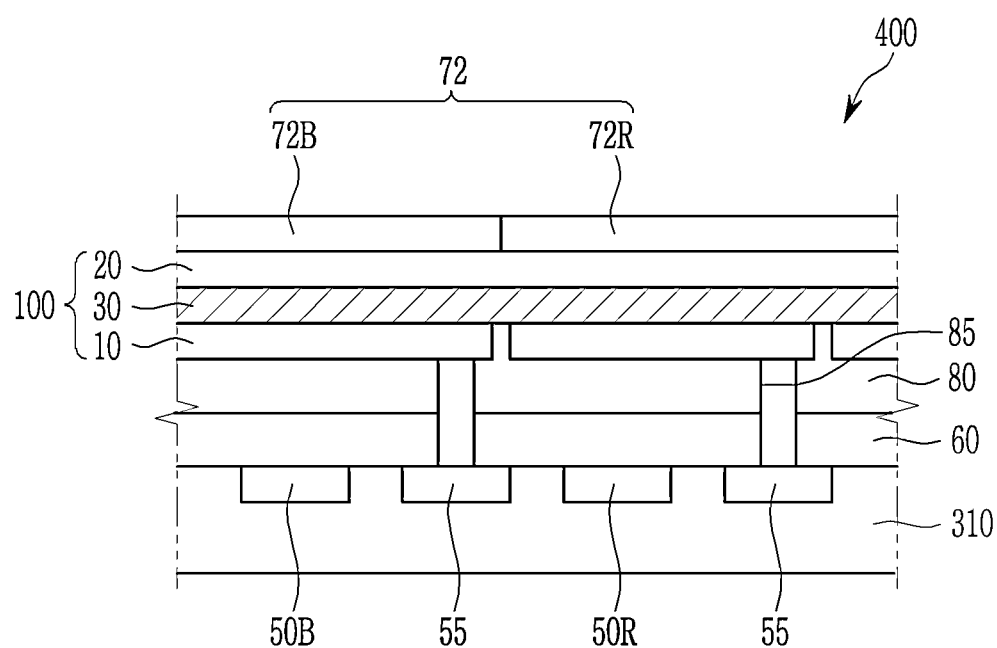
FIG. 5 is a schematic cross-sectional view of an organic CMOS image sensor according to another embodiment.

The organic CMOS image sensor with the color filters disposed on the photoelectric device is shown in FIG. 5. FIG. 5 is a schematic cross-sectional view showing an organic CMOS image sensor according to an embodiment. Referring to FIG. 5, an organic CMOS image sensor 400 has the same structure as FIG. 4 except that a color filter layer 72 including the blue filter 72B and the red filter 72R is disposed on the photoelectric device 100. Instead of the blue filter 72B and the red filter 72R, the cyan filter 72C and the yellow filter 72Y may be disposed respectively.

Figure 6:
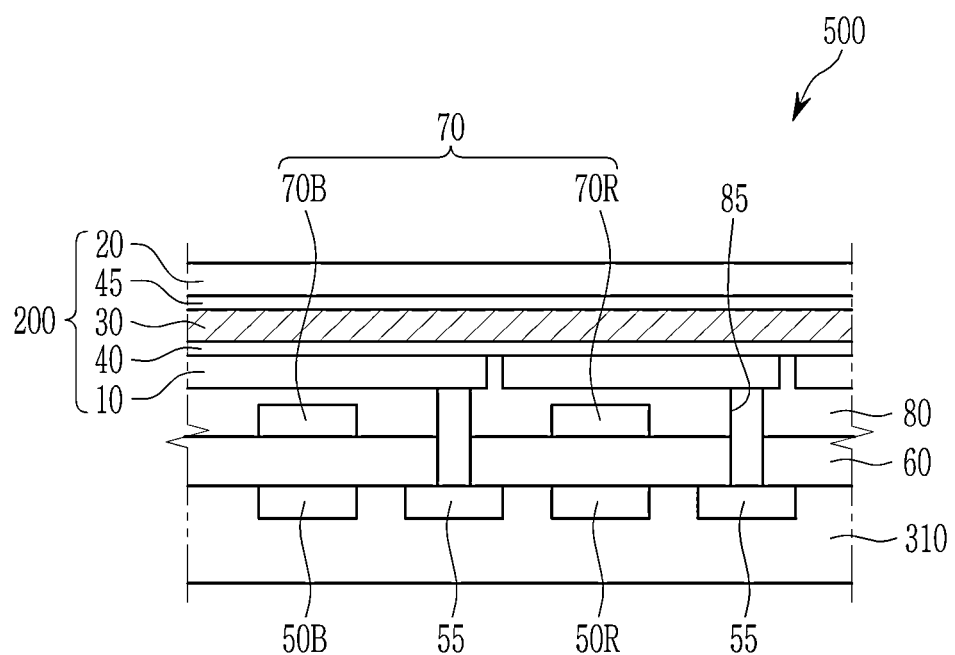
FIG. 6 is a schematic cross-sectional view of an organic CMOS image sensor according to another embodiment.

In FIGS. 4 and 5, the photoelectric device 100 of FIG. 1 is included, but it is not limited thereto, and thus the photoelectric device 200 of FIG. 2 may be applied in the same manner. FIG. 6 is a cross-sectional view showing an organic CMOS image sensor 500 to which the photoelectric device 200 is applied.

Figure 7:
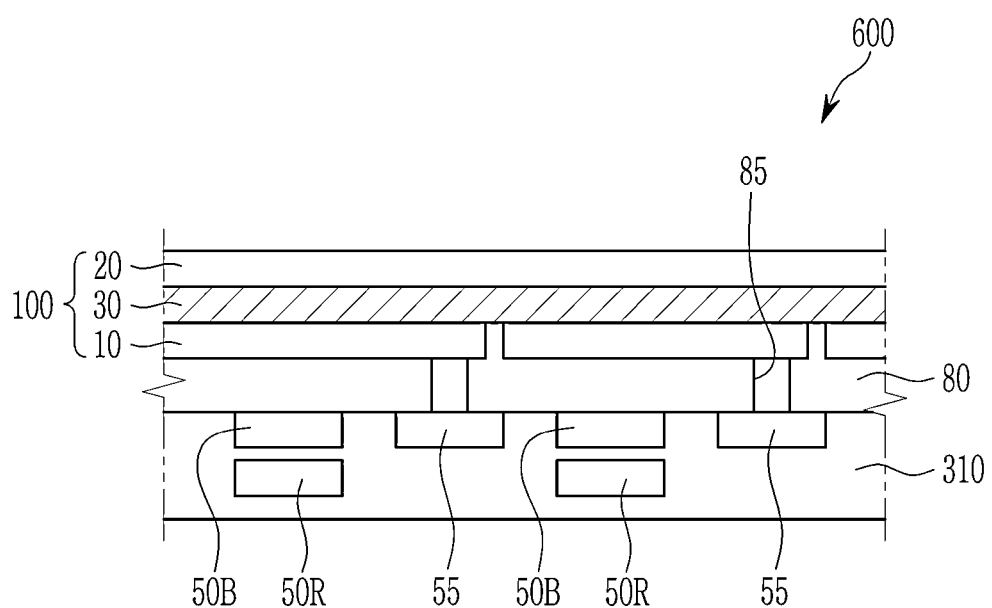
FIG. 7 is a cross-sectional view of an organic CMOS image sensor according to another embodiment.

FIG. 7 is a schematic view showing an organic CMOS image sensor according to another embodiment.

Referring to FIG. 7, the organic CMOS image sensor 600 includes a semiconductor substrate 310 integrated with photo-sensing devices 50B and 50R, a transmission transistor (not shown), a charge storage 55, an insulation layer 80, and a photoelectric device 100, like the example embodiment illustrated in FIG. 5.

However, the organic CMOS image sensor 600 according to the embodiment includes the blue photo-sensing device 50B and the red photo-sensing device 50R that are stacked and does not include a color filter layer 70, unlike the aforementioned embodiments. The blue photo-sensing device 50B and the red photo-sensing device 50R are electrically connected with the charge storage 55, and the information of the charge storage 55 may be transferred by the transmission transistor (not shown). The blue photo-sensing device 50B and the red photo-sensing device 50R may selectively absorb light in each wavelength region depending on a stack depth.

As described above, the photoelectric devices selectively absorbing light in a green wavelength region are stacked and the red photo-sensing device and the blue photo-sensing device are stacked, and thereby a size of an image sensor may be decreased and a down-sized image sensor may be realized. As described above, the photoelectric device 100 has improved green wavelength selectivity, and crosstalk caused by unnecessary absorption of light in a wavelength region except green may be decreased while increasing sensitivity.

In FIG. 7, the photoelectric device 100 of FIG. 1 is included, but it is not limited thereto, and thus the photoelectric device 200 of FIG. 2 may be applied in the same manner.

Figure 8:
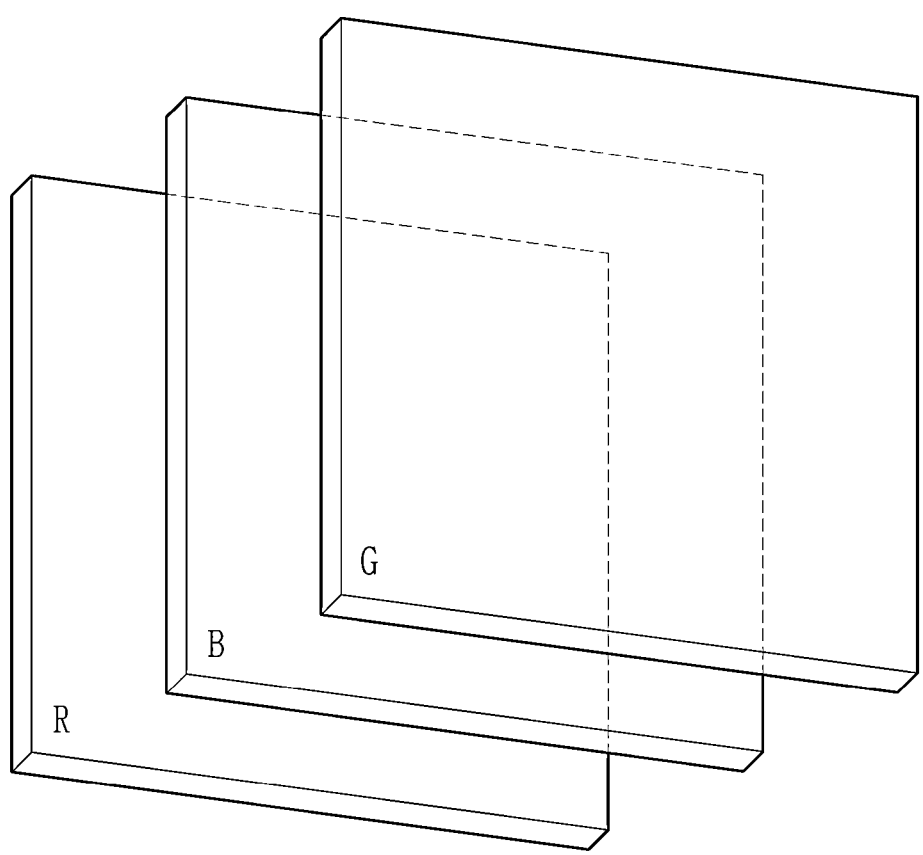
FIG. 8 is a schematic view showing an organic CMOS image sensor according to another embodiment.

FIG. 8 is a schematic view showing an organic CMOS image sensor according to another example embodiment.

Referring to FIG. 8, the organic CMOS image sensor according to the present embodiment includes a green photoelectric device (G) selectively absorbing light in a green wavelength region, a blue photoelectric device (B) selectively absorbing light in a blue wavelength region, and a red photoelectric device (R) selectively absorbing light in a red wavelength region that are stacked.

In the drawing, the red photoelectric device, the green photoelectric device, and the blue photoelectric device are sequentially stacked, but the stack order may be changed without limitation.

The green photoelectric device (G) may be the aforementioned photoelectric device 100 or photoelectric device 200, the blue photoelectric device (B) may include electrodes facing each other and an active layer therebetween and including an organic material selectively absorbing light in a blue wavelength region, and the red photoelectric device (R) may include electrodes facing each other and an active layer therebetween and including an organic material selectively absorbing light in a red wavelength region.

As described above, the green photoelectric device (G) selectively absorbing light in a green wavelength region, the blue photoelectric device (B) selectively absorbing light in a blue wavelength region, and the red photoelectric device (R) selectively absorbing light in a red wavelength region are stacked, and thereby a size of an image sensor may be decreased and a down-sized image sensor may be realized.

The image sensor absorbs light in an appropriate wavelength region and may show all improved sensitivity (YSNR10) and color reproducibility (ΔE*ab) despite a stacked structure.

Herein, the YSNR10 indicates sensitivity of the image sensor, which is measured in a method described in Juha Alakarhu's "Image Sensors and Image Quality in Mobile Phones" printed in 2007 International Image Sensor Workshop (Ogunquit Maine, USA) but minimum illuminance expressed by lux at a ratio of 10 between signal and noise. Accordingly, the smaller the YSNR10 is, the higher sensitivity is.

On the other hand, the color reproducibility (ΔE*ab) shows a difference from standard colors in an X-Rite chart, and the ΔE*ab is defined as a distance between two points on a L*a*b* color space by CIE (Commission International de L'Eclairage) in 1976. For example, the color difference may be calculated according to Equation 1.

$$\Delta E = \sqrt{(\Delta L^*)^2 + (\Delta a^*)^2 + (\Delta b^*)^2}$$ [Equation 1]

In Equation 1,

ΔL* denotes a change of a color coordinate L* compared with the color coordinate L* at room temperature (about 20° C. to about 25° C.), Δa* denotes a change of a color coordinate a* compared with the color coordinate a* at room temperature (about 20° C. to about 25° C.), and Δb* denotes a change of a color coordinate b* compared with the color coordinate b* at room temperature (about 20° C. to about 25° C.).

In order to manufacture an image sensor having high sensitivity and high color reproducibility, YSNR10≤100 lux at ΔE*ab≤3, and herein, the compound may realize YSNR10≤100 lux of sensitivity and color reproducibility at ΔE*ab≤3.

The image sensor may be applied to various electronic devices, for example, a mobile phone, a digital camera, and the like but is not limited thereto.

Figure 9:
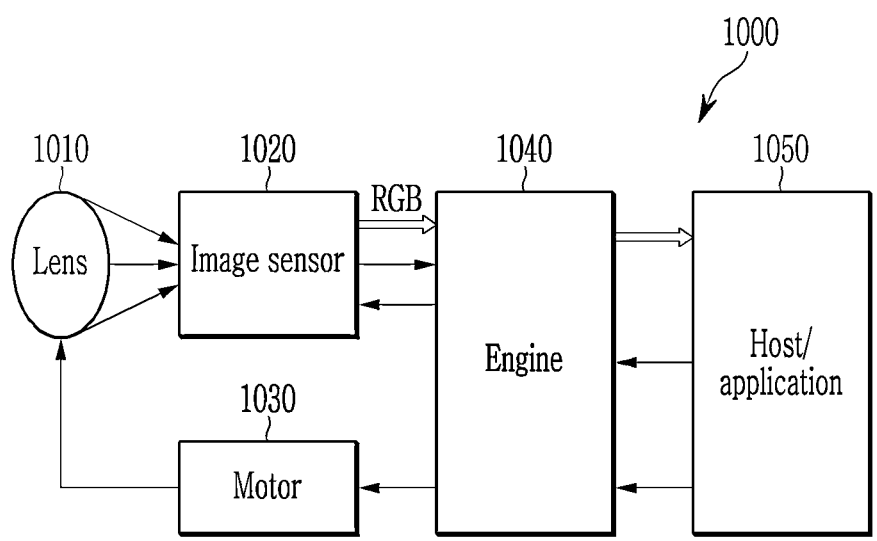
FIG. 9 is a block diagram of a digital camera including an image sensor according to an embodiment.

FIG. 9 is a block diagram of a digital camera including an image sensor according to an embodiment.

Referring to FIG. 9, a digital camera 1000 includes a lens 1010, an image sensor 1020, a motor 1030, and an engine 1040. The image sensor 1020 may be one of image sensors according to embodiments shown in FIGS. 3 to 8 of the present application.

The lens 1010 concentrates incident light on the image sensor 1020. The image sensor 1020 generates RGB data for received light through the lens 1010.

In some embodiments, the image sensor 1020 may interface with the engine 1040.

The motor 1030 may adjust the focus of the lens 1010 or perform shuttering in response to a control signal received from the engine 1040. The engine 1040 may control the image sensor 1020 and the motor 1030.

The engine 1040 may be connected to a host/application 1050.

Figure 10:
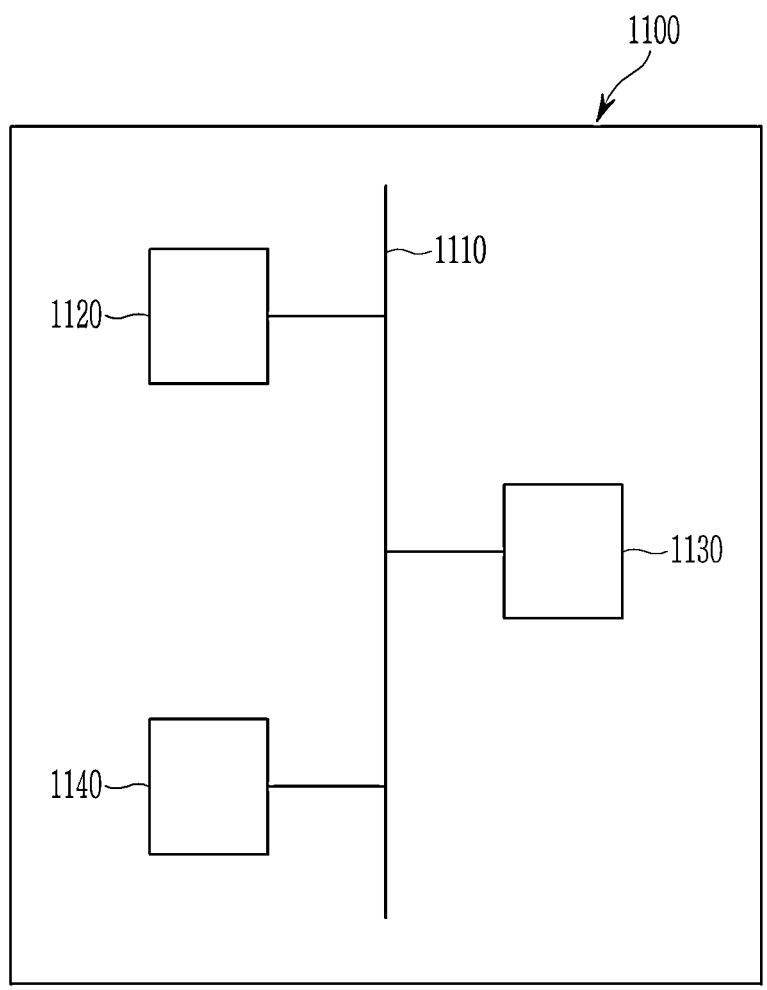
FIG. 10 is a schematic diagram showing an electronic device according to some embodiments.

FIG. 10 is a schematic diagram showing an electronic device according to some embodiments. Referring to FIG. 10, an electronic device 1100 may include a processor 1120, a memory 1130, and an image sensor 1140 that are electrically coupled together via a bus 1110. The image sensor 1140 may be one according to one of the aforementioned embodiments. The memory 1130 may be a non-transitory computer readable medium and may store a program of instructions. The memory 1130 may be a nonvolatile memory, such as a flash memory, a phase-change random access memory (PRAM), a magneto-resistive RAM (MRAM), a resistive RAM (ReRAM), or a ferro-electric RAM (FRAM), or a volatile memory, such as a static RAM (SRAM), a dynamic RAM (DRAM), or a synchronous DRAM (SDRAM). The processor 1120 may execute the stored program of instructions to perform one or more functions. For example, the processor 1120 may be configured to process electrical signals generated by the image sensor 1140. The processor 1120 may include processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc. The processor 1120 may be configured to generate an output (e.g., an image to be displayed on a display interface) based on such processing.

Hereinafter, the embodiments are illustrated in more detail with reference to examples. However, these examples are non-limiting, and inventive concepts are not limited thereto.

Synthesis Example 1: Synthesis of Compound Represented by Chemical Formula 1-1

[Chemical Formula 1-1]

[Reaction Scheme 1-1]

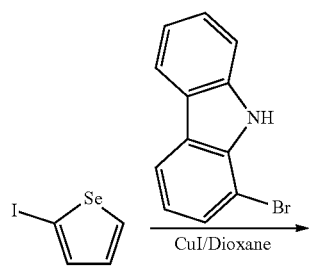

-continued

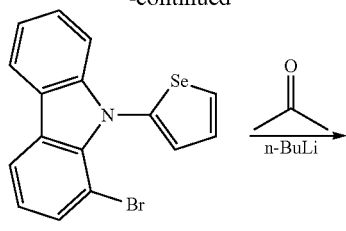

1-1A

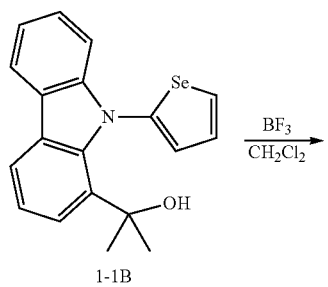

1-1B

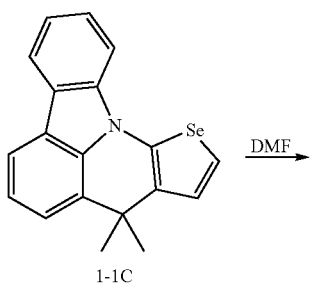

1-1C

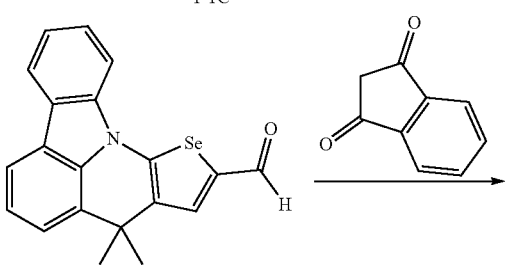

1-1D

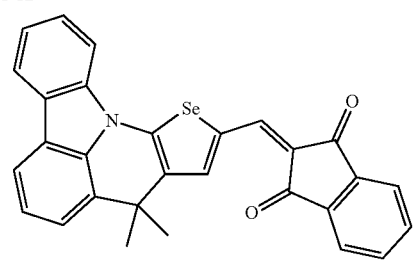

1-1

(i) Synthesis of Compound 1-1A 9.4 g (36.5 mmol) of 2-Iodoselenophene and 7.5 g (30.5 mmol) of 1-bromo-9H-carbazole are dissolved in 30 ml of dioxane. 0.29 g (1.52 mmol) of copper (I) Iodide, 0.70 g (6.09 mmol) of trans-1,2-cyclohexanediamine, and 12.9 g (61.0 mmol) of tripotassium phosphate are added thereto and then, heated and refluxed for 30 hours. A product obtained therefrom is separated and purified through silica gel column chromatography (in a volume ratio of hexane: ethyl acetate=5:1) to obtain 8.18 g (Yield: 72%) of Compound 1-1A.

(ii) Synthesis of Compound 1-1B 12.0 g (32.0 mmol) of Compound 1-1A is dissolved in 300 ml of dehydrated diethyl ether. 12 ml (32.0 mmol) of a 2.76 M n-butyl lithium (n-BuLi) hexane solution is added thereto in a dropwise fashion at −50° C. and then, stirred for 1 hour at room temperature. 2.0 g (35.2 mmol) of dehydrated acetone (dimethylketone, $CH_3COCH_3$) is added thereto at −50° C. and then, stirred at room temperature for 2 hours. An organic layer extracted in diethyl ether is washed with a sodium chloride aqueous solution and then, dried by adding anhydrous magnesium sulfate thereto. Herein, a product obtained therefrom is separated and purified through silica gel column chromatography (in a volume ratio between hexane:dichloromethane=100:0 to 50:50 to obtain 6.3 g (Yield: 56%) of Compound 1-1B.

(iii) Synthesis of Compound 1-1C 6.23 g (17.6 mmol) of Compound 1-1B is dissolved in 180 ml of dichloromethane. 4.98 g (35.5 mmol) of a boron trifluoride-ethyl ether complex is added thereto in a dropwise fashion at 0° C. and then, stirred for 2 hours. An organic layer extracted in dichloromethane is washed with a sodium chloride aqueous solution and then, dried by adding anhydrous magnesium sulfate thereto. Herein, a product obtained therefrom is separated and purified through silica gel column chromatography (in a volume ratio between hexane:dichloromethane=50:50) to obtain 5.12 g (Yield: 87%) of Compound 1-1C.

(iv) Synthesis of Compound 1-1D 1.9 ml (20.2 mmol) of phosphoryl chloride is added in a dropwise fashion to 6.0 ml (77.5 mmol) of N,N-dimethyl formamide (DMF) at −15° C. and then, stirred at room temperature for 2 hours. This solution is slowly dripped to 150 ml of a dichloromethane solution of 5.23 g (15.5 mmol) of Compound 1-1C at −15° C., stirred at room temperature for 30 hours, and then, concentrated under a low pressure. Subsequently, water is added thereto, and a sodium hydroxide aqueous solution is added thereto until pH becomes 1 quadrivalent, and the obtained mixture is stirred at room temperature for 2 hours. An organic layer extracted with dichloromethane is washed with a sodium chloride aqueous solution and then, dried with anhydrous magnesium sulfate. A product obtained therefrom is separated and purified through silica gel column chromatography (in a volume ratio of hexane:dichloromethane=50:50) to obtain 3.34 g (Yield: 65%) of Compound 1-1D.

(v) Synthesis of Compound Represented by Chemical Formula 1-1

1.50 g (4.11 mmol) of Compound 1-1D is dissolved in 20 ml of tetrahydrofuran, and 0.72 g (4.93 mmol) of 1H-indene-1,3(2H)-dione is added thereto and then, stirred at 50° C. for 4 hours and concentrated under a reduced pressure. Chloroform and ethanol are used for recrystallization to obtain 2.03 g (Yield: 74%) of a compound represented by Chemical Formula 1-1. The compound is purified through sublimation up to purity of 99.9%.

$^1$H-NMR (300 MHZ, Methylene Chloride-$d_2$): δ 8.15 (d, 1H), 8.14 (s, 1H), 8.07 (s, 1H), 8.03 (d, 1H), 7.95-7.88 (m, 3H), 7.82-7.77 (m, 2H), 7.72 (td, 1H), 7.45-7.55 (m, 3H), 1.79 (s, 6H).

Synthesis Example 2: Synthesis of Compound Represented by Chemical Formula 1-2

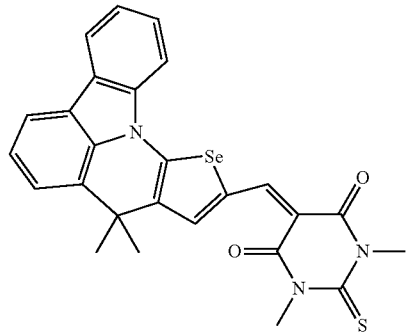

[Chemical Formula 1-2]

1.29 g (Yield: 60%) of a compound represented by Chemical Formula 1-2 is obtained according to the same method as Synthesis Example 1 except that 0.48 g (4.93 mmol) of 1,3-dimethyl-2-thiobarbituric acid is used instead of the 1H-indene-1,3(2H)-dione in the step (v) of Synthesis Example 1. The compound is purified through sublimation up to purity of 99.9%.

MS (ESI$^+$): calculated for $C_{26}H_{21}N_3O_2SSe$ [M+H$^+$]: 519.05; found: 519.90

Synthesis Example 3: Synthesis of Compound Represented by Chemical Formula 1-3

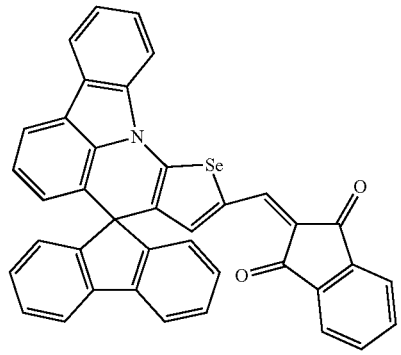

[Chemical Formula 1-3]

1.86 g (Yield: 74%) of a compound represented by Chemical Formula 1-3 is obtained according to the same method as Synthesis Example 1 except that 9H-fluoren-9-one is used instead of the acetone in the step (ii) of Synthesis Example 1. The final compound is purified through sublimation up to purity of 99.9%.

$^1$H-NMR (300 MHZ, Methylene Chloride-$d_2$): δ 8.22 (d, 1H), 8.12 (d, 1H), 7.52-7.97 (m, 8H), 7.64 (s, 1H), 7.55 (td, 1H), 7.27 (td, 2H), 7.26-7.15 (m, 3H), 7.07 (s, 1H), 6.56 (dd, 1H).

Synthesis Example 4: Synthesis of Compound Represented by Chemical Formula 1-4

[Chemical Formula 1-4]

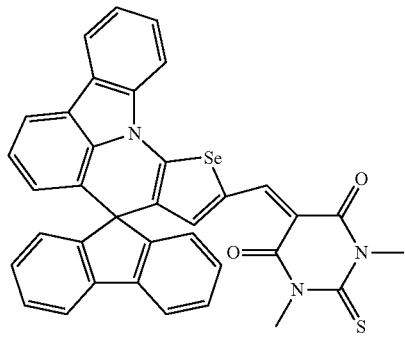

A compound represented by Chemical Formula 1-4 is obtained according to the same method as Synthesis Example 1 except that 9H-fluoren-9-one is used instead of the acetone in the step (ii) of Synthesis Example 1, and 0.48 g (4.93 mmol) of 1,3-dimethyl-2-thiobarbituric acid is used instead of the 1H-indene-1,3(2H)-dione in the step (v) of Synthesis Example 1. The obtained compound is purified through sublimation up to purity of 99.9%.

Synthesis Example 5: Synthesis of Compound Represented by Chemical Formula 1-5

[Chemical Formula 1-5]

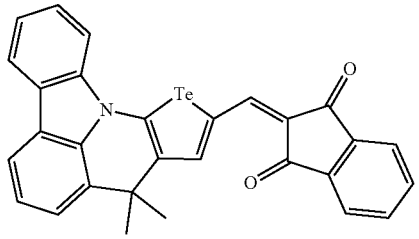

[Reaction Scheme 1-5]

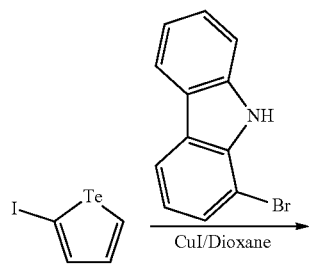

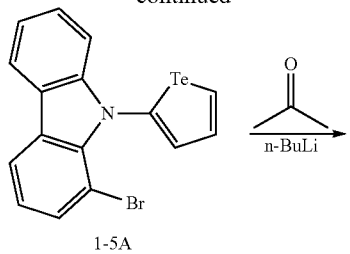

1-5A

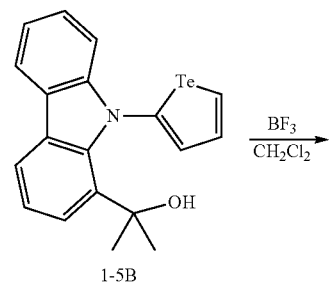

1-5B

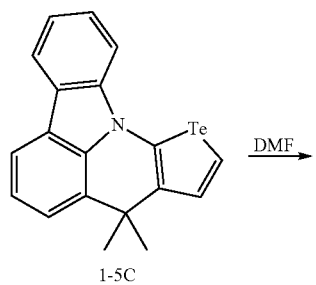

1-5C

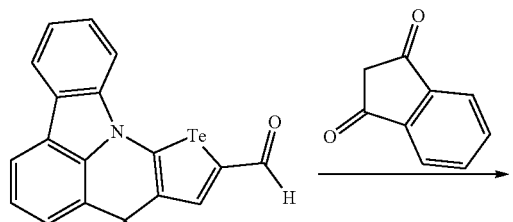

1-5D

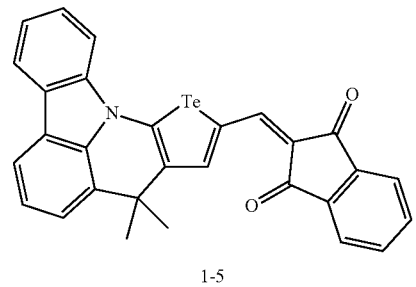

1-5

A compound represented by Chemical Formula 1-5 is obtained in the same manner as in Reaction Scheme 1-1 of Synthesis Example 1, except that 2-iodotellurophene is used instead of 2-iodoselenophene.

Synthesis Example 6: Synthesis of Compound Represented by Chemical Formula 1-6

[Chemical Formula 1-6]

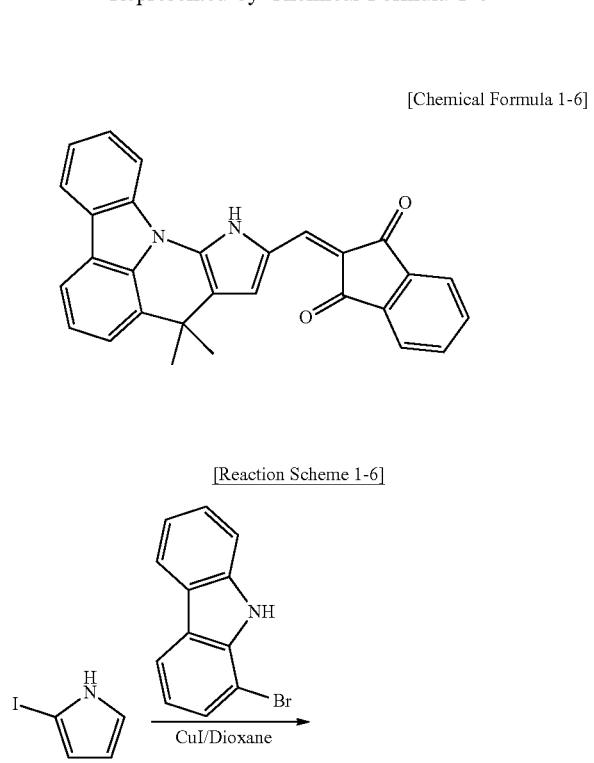

[Reaction Scheme 1-6]

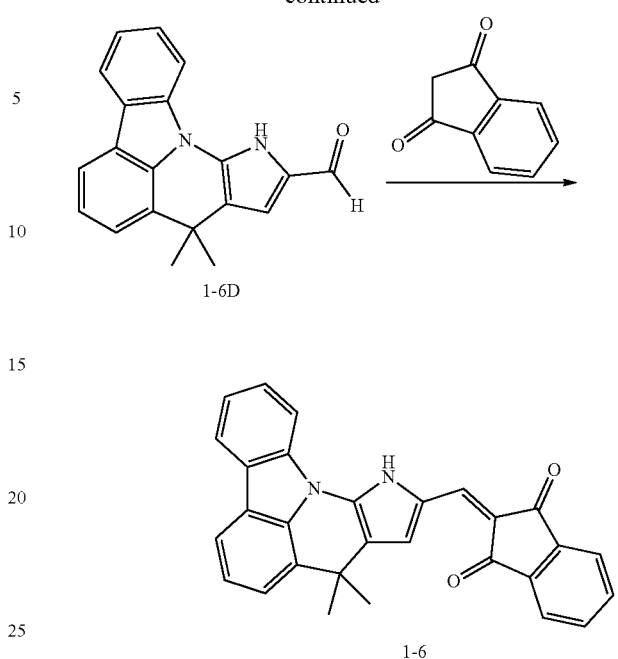

A compound represented by Chemical Formula 1-6 is obtained in the same manner as in Reaction Scheme 1-1 of Synthesis Example 1, except that 2-iodopyrrole is used instead of 2-iodoselenophene.

Reference Synthesis Example 1: Synthesis of Compound Represented by Chemical Formula 2-1

[Chemical Formula 2-1]

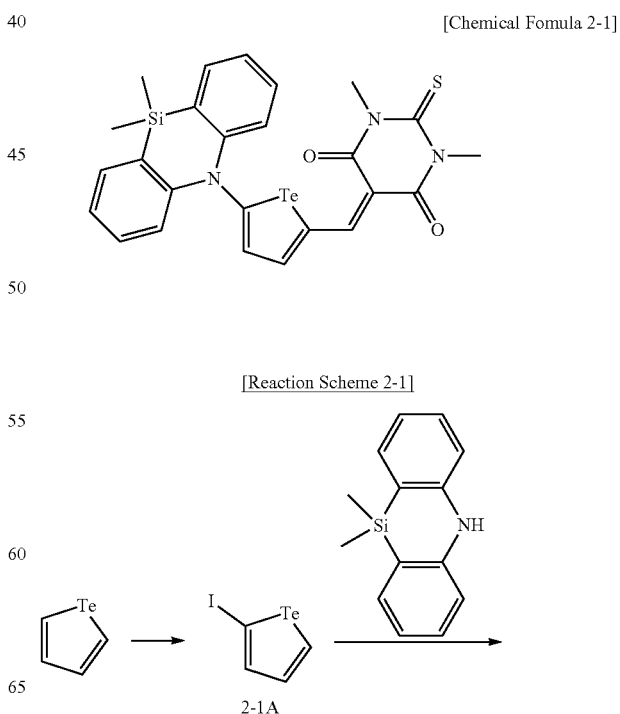

[Reaction Scheme 2-1]

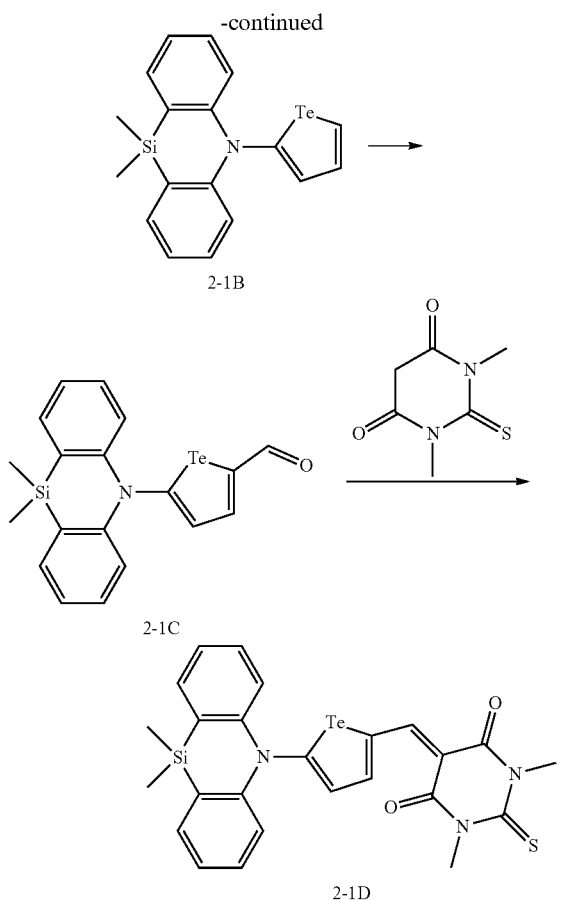

(i) Synthesis of Compound 2-1A 2-iodotellurophene is synthesized referring to the method disclosed in Efficient Synthesis of 2-Iodo and 2-Dicyanomethyl Derivatives of Thiophene, Selenophene, Tellurophene, and Thieno[3,2-b]thiophene, Takahashi, K.; Tarutani, S. Heterocycles 1996, 43, 1927-1935.

(ii) Synthesis of Compound 2-1B 15.0 g (49.1 mmol) of 2-iodotellurophene and 10.0 g (44.6 mmol) of 10,10-dimethyl-5,10-dihydrodibenzo[b,e][1,4]azasiline are heated and refluxed for 2 hours in 200 ml of anhydrous toluene in the presence of 2.23 mmol of bis(dibenzylideneacetone) palladium (0) (Pd(dba)$_2$), 2.23 mmol of tri-tert-$7 butylphosphine (P(tBu)$_3$), and 12.9 g (133.9 mmol) of sodium tert-butoxide (NaOtBu). A product obtained therefrom is separated and purified through silica gel column chromatography (toluene:hexane=volume ratio of 1:4) to obtain 6.8 g of 10,10-dimethyl-5-(tellurophen-2-yl)-5,10-dihydrodibenzo[b,e][1,4]azasiline (Yield: 37.8%).

(iii) Synthesis of Compound 2-1C 6.2 ml of phosphoryl chloride is added in a dropwise fashion to 30.0 ml of N,N-dimethylformamide at −15° C., and the mixture is stirred at room temperature (24° C.) for 2 hours. The resultant therefrom is slowly added in a dropwise fashion to a mixture of 300 ml of dichloromethane and 6.8 g of Compound 2-1B at −15° C., and the obtained mixture is stirred at room temperature for 30 minutes and concentrated under a reduced pressure. 300 ml of water is added thereto, an aqueous sodium hydroxide solution is added thereto until pH becomes 14, and the obtained mixture is stirred at room temperature for 2 hours. An organic layer extracted therefrom by using dichloromethane is washed with an aqueous sodium chloride solution and then, dried by adding magnesium sulfate anhydrous thereto. A product obtained therefrom is separated and purified through silica gel column chromatography (hexane:ethylacetate=volume ratio of 4:1) to obtain 2.82 g of 5-(10,10-dimethyldibenzo[b,e][1,4]azasilin-5(10H)-yl)tellurophene-2-carbaldehyde (Yield: 38.8%).

(iv) Synthesis of Compound 2-1D Represented by Chemical Formula 2-1

2.82 g (6.54 mmol) of Compound 2-1C is suspended in ethanol, 1.35 g (7.85 mmol) of 1,3-dimethyl-2-thiobarbituric acid synthesized according to a method described in J. Pharmacol., 1944, 82, 292, p. 4417 is added thereto, and the mixture is reacted at 50° C. for 2 hours to obtain 2.98 g of the compound represented by Chemical Formula 2-1 (Yield: 77.8%). The compound is sublimed and purified up to purity of 99.9%.

$^1$H-NMR (500 MHZ, Methylene Chloride-d$_2$): δ 8.46 (s, 1H), 8.26 (d, 1H), 7.80 (d, 2H), 7.71 (d, 2H), 7.54 (t, 2H), 7.42 (t, 2H), 6.93 (d, 1H), 3.68 (d, 6H), 0.45 (s, 6H).

Reference Synthesis Example 2: Synthesis of Compound Represented by Chemical Formula 2-2

A compound represented by Chemical Formula 2-2 is synthesized according to the same method as Reference Synthesis Example 1 except that 2-Iodoselenophene is used instead of the 2-iodotellurophene of Reference Synthesis Example 1.

[Chemical Formula 2-2]

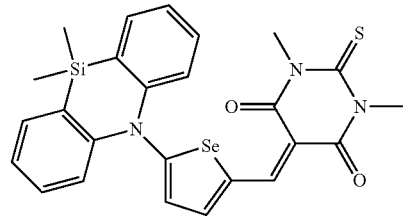

Reference Synthesis Example 3: Synthesis of Compound Represented by Chemical Formula 2-3

[Chemical Formula 2-3]

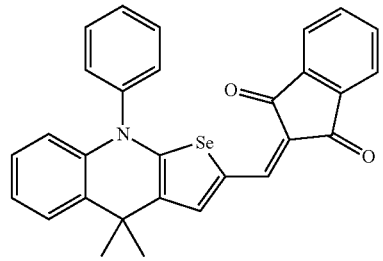

2.0 g (Yield: 70%) of a compound represented by Chemical Formula 2-3 is synthesized according to the same method as Synthesis Example 1 except that 2-bromo-N-phenylalanine is used instead of the 1-bromo-9H-carbazole in the step (i) of Synthesis Example 1.

$^1$H-NMR (300 MHZ, Methylene Chloride-$d_2$): δ 7.86 (m, 6H), 7.35 (m, 4H), 7.23 (m, 6H), 4.99 (s, 1H), 4.86 (s, 1H), 1.81 (s, 3H).

Reference Synthesis Example 4: Synthesis of Compound Represented by Chemical Formula 2-4

[Chemical Formula 2-4]

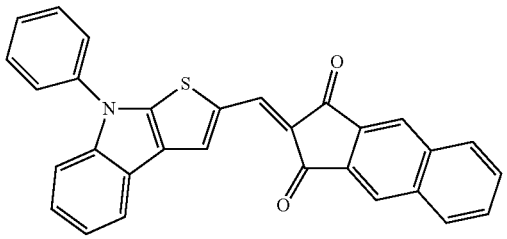

[Reaction Scheme 2-4]

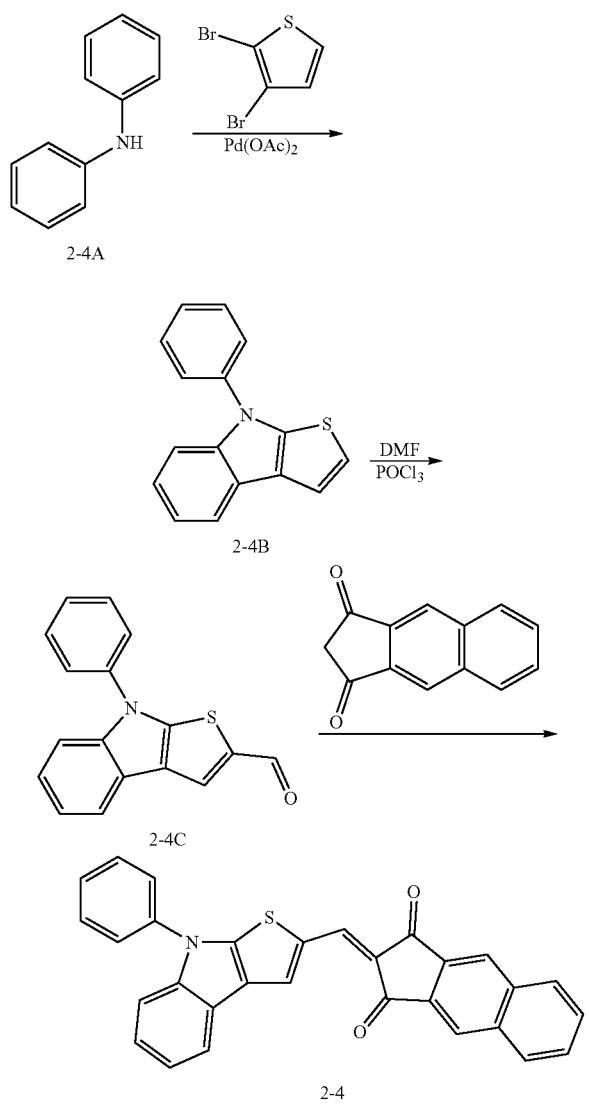

Compound 2-4B is synthesized by using diphenylamine and 2,3-dibromothiophene as shown in Reaction Scheme 2-4 with reference to Angewante chem., Int. Ed. 2007, 46, 1627-1629. Subsequently, 0.74 ml of chloridephosphoryl (POCl$_3$) is cooled down to 0° C. and then, slowly dripped to 2.3 ml of dimethyl formamide (DMF) to prepare a Vilsmeier reagent. Subsequently, a solution prepared by dissolving 2.1 g of Compound 2-4B in 2.0 ml of anhydrous DMF is cooled down and slowly dripped into the Vilsmeier reagent and then, heated and stirred at 80° C. for 2 hours. The resultant is cooled down to room temperature (25° C.) and neutralized with ammonium acetate. After filtering and removing solids precipitated therein, the filtered solution is extracted with toluene and dried with magnesium sulfate, and a compound in an oil state is obtained therefrom and then, separated by using dichloromethane through silica gel column chromatography to obtain Compound 2-4C (1.1 g, Yield: 48%).

Subsequently, 1.0 g of Compound 2-4C and 0.9 g of 1H-cyclopenta[b]naphthalene-1,3(2H)-dione are dissolved in 50 ml of ethanol, and three drops of piperidine are added thereto and then, heated and refluxed for 3 hours. After removing the solvent under a reduced pressure, the residue was purified through silica gel column chromatography to obtain 1.0 g (Yield: 75%) of a compound represented by Chemical Formula 2-4.

Example 1: Manufacture of Photoelectric Device

ITO is laminated on a glass substrate through sputtering to form an about 150 nm-thick anode, and the ITO glass substrate is ultrasonic wave-cleaned with acetone/isopropyl alcohol/pure water respectively for 15 minutes and then, UV ozone-cleaned. Subsequently, the compound according to Synthesis Example 1 and C60 are code posited in a volume ratio of 1.2:1 to form a 120 nm-thick active layer, and ITO is vacuum-deposited to be 7 nm thick to manufacture a photoelectric device having a structure of ITO (150 nm)/ active layer (120 nm)/ITO (7 nm).

Examples 2 to 4 and Reference Examples 1 to 4: Manufacture of Photoelectric Device Photoelectric devices according to Examples 2 to 4 and Reference Examples 1 to 4 are manufactured according to the same method as Example 1 except that the compounds according to Synthesis Examples 2 to 4 and Reference Synthesis Examples 1 to 4 are respectively used instead of the compound of Synthesis Example 1.

Evaluation 1: Light Absorption Characteristics of Compound

Light absorption characteristics (maximum absorption wavelength and absorption coefficient) of the compounds according to Synthesis Examples 1 to 4 depending on a wavelength are evaluated. Each compound according to Synthesis Examples 1 to 4 and C60 are deposited in a volume ratio of 1:1 to form thin films, and each thin film is evaluated with respect to light absorption characteristics in an ultraviolet (UV)-visible ray (UV-Vis) region by using Cary 5000 UV spectroscopy (Varian Inc.). The results are shown in Table 1.

TABLE 1

| Compounds | Chemical Formula | λ$_{max}$ (nm) | Abs. coeff. ($10^4$ cm$^{-1}$) |
|---|---|---|---|
| Synthesis Example 1 | 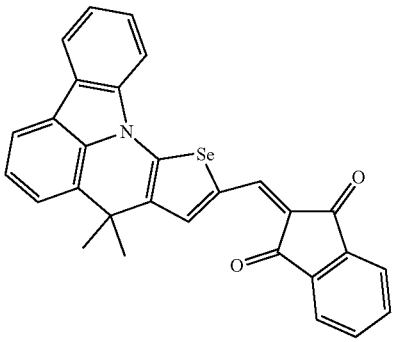 [SMILES: CC1(C)c2cc(C=C3C(=O)c4ccccc4C3=O)[se]c2-n2c3ccccc3c3cccc1c32] | 555 | 7.3 |
| Synthesis Example 2 | 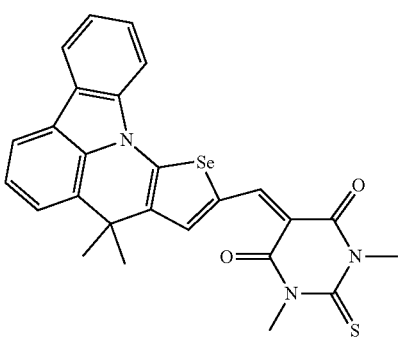 [SMILES: CN1C(=O)C(=Cc2cc3c([se]2)-n2c4ccccc4c4cccc(c42)C3(C)C)C(=O)N(C)C1=S] | 555 | 7.3 |
| Synthesis Example 3 | 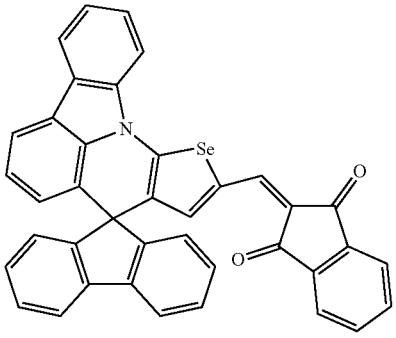 [SMILES: O=C1C(=Cc2cc3c([se]2)-n2c4ccccc4c4cccc(c42)C32c3ccccc3-c3ccccc32)C(=O)c2ccccc21] | 550 | 6.1 |
| Synthesis Example 4 | 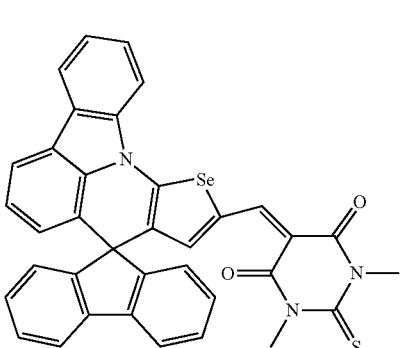 | 550 | 6.9 |

Referring to Table 1, the compounds of Synthesis Examples 1 to 4 exhibit a maximum absorption wavelength in a green wavelength region and thus a high absorption coefficient (absorption intensity). Accordingly, the compounds of Synthesis Examples 1 to 4 exhibit excellent absorption selectivity in the green wavelength region.

Evaluation 2: External Quantum Efficiency (EQE) of Photoelectric Device

External quantum efficiency (EQE) of the organic photoelectric devices according to Examples 1 to 4 and Reference Examples 1 to 4 depending on a wavelength and a voltage is evaluated.

The external quantum efficiency is measured by using IPCE Measurement System (McScience Inc., Korea). First, the IPCE Measurement System is calibrated by using an Si photodiode (Hamamatsu Photonics K.K., Japan) and then, mounted on the photoelectric devices according to Examples 1 to 4 and Reference Examples 1 to 4, and external quantum efficiency thereof within a wavelength range of about 350 to about 750 nm is measured. After annealing the photoelectric devices at 180° C., 190° C., and 200° C., external quantum efficiency thereof is measured in the aforementioned method. Among them, the external quantum efficiency results of the photoelectric devices of Examples 1 and 2 and Reference Examples 1 to 4 are shown in Table 1.

TABLE 2

| | EQE (room temperature, %) | EQE (180° C., %) | EQE (190° C., %) | EQE (200° C., %) |
| --- | --- | --- | --- | --- |
| Example 1 | 70 | 68 | 66 | 67 |
| Example 2 | 67 | 65 | 64 | 63 |
| Reference Example 1 | 70 | 68 | 66 | Not measurable |
| Reference Example 2 | 65 | 63 | Not measurable | Not measurable |
| Reference Example 3 | 40 | Not measurable | Not measurable | Not measurable |
| Reference Example 4 | 35 | Not measurable | Not measurable | Not measurable |

Referring to Table 2, the photoelectric devices according to Examples 1 and 2 exhibits excellent external quantum efficiency after the annealing at greater than or equal to 180° C. as well as room temperature. On the contrary, device characteristics of the photoelectric devices according to Reference Examples 1, 2, 3, and 4 are deteriorated after the annealing at 200° C., 190° C., and 180° C., and thus EQE's thereof are not measured.

Evaluation 3: Residual Charge Characteristics of Photoelectric Device

When photoelectrically converted charges are not all used for signal treatment but remain in one frame, the charges in the former frame are overlapped and read with charges in the following frame, and herein, an amount of the charges in the following frame is called to be an amount of residual charges. The amount of the residual charges is measured by irradiating light in the green wavelength region of 532 nm where the photoelectric conversion may occur for desired and/or alternatively predetermined time, turning off the light, and integrating the current measured in units of 10-6 seconds with an oscilloscope equipment, by time. The amount of the residual charges is evaluated by a h+/s/μm² unit based on 5000 lux light. Among them, the residual charge measurement results of the photoelectric devices according to Examples 1 and 2 and Reference Examples 1 and 2 are shown in Table 3.

TABLE 3

| | Residual charge (room temperature, h+/s/μm²) | Residual charge (180° C., h+/s/μm²) | Residual charge (190° C., h+/s/μm²) | Residual charge (200° C., h+/s/μm²) |
| --- | --- | --- | --- | --- |
| Example 1 | 35 | 20 | 17 | 17 |
| Example 2 | 31 | 25 | 23 | 21 |
| Reference Example 1 | 509 | 100 | 78 | Not measurable |
| Reference Example 2 | 579 | Not measurable | Not measurable | Not measurable |

Referring to Table 3, the photoelectric devices of Examples 1 and 2 exhibit excellent residual charge characteristics after the annealing at greater than or equal to 180° C. as well as room temperature. On the contrary, device characteristics of the photoelectric devices of Reference Examples 1 and 2 are deteriorated, and thus the residual charge amounts thereof are not measured after each annealing at 200° C., 190° C., and 180° C.

While this disclosure has been described in connection with what is presently considered to be practical example embodiments, it is to be understood that inventive concepts are not limited to the disclosed embodiments, but, on the contrary, are intended to cover various modifications and equivalent arrangements included within the spirit and scope of the appended claims.

DESCRIPTION OF SYMBOLS

10: first electrode
20: second electrode
30: active layer
40, 45: charge auxiliary layer
100, 200: photoelectric device
300, 400, 500, 600: organic CMOS image sensor
310: semiconductor substrate
70B, 72B: blue filter
70R, 72R: red filter
70, 72: color filter layer
85: through-hole
60: lower insulation layer
80: upper insulation layer
50B, 50R: photo-sensing device
55: charge storage
1000: digital camera
1010: lens
1020: image sensor
1030: motor
1040: engine
1050: host/application

What is claimed is:
1. A compound represented by Chemical Formula 1:

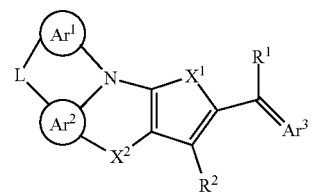

[Chemical Formula 1]

wherein, in Chemical Formula 1,
Ar¹ and Ar² are independently a substituted or unsubstituted C6 to C30 arene group, or a substituted or unsubstituted C3 to C30 heteroarene group, or a condensed ring thereof, $X^1$ is —Se—, —Te—, or —NR$^{a1}$—, wherein R$^{a1}$ is hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, $X^2$ is —O—, —S—, —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —(CR$^f$R$^g$)$_{n1}$—, —(CR$^{ff}$R$^{gg}$)—, —(C(R$^m$)=C(R$^n$))—, —(C(R$^{mm}$)=C(R$^{nn}$))—, or —(C(R$^p$)=N))—, wherein R$^{a1}$, R$^{a2}$, R$^b$, R$^c$, R$^d$, R$^e$, R$^f$, R$^g$, R$^m$, R$^n$, and R$^p$ are independently hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and R$^{bb}$ and R$^{cc}$, R$^{dd}$ and R$^{ee}$, R$^{ff}$ and R$^{gg}$, and R$^{mm}$ and R$^{nn}$ are linked with each other to provide a ring structure, and n1 of —(CR$^f$R$^g$)$_{n1}$— is 1 or 2, L is —O—, —S—, —Se—, —Te—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —(CR$^f$R$^g$)$_{n1}$—, —(CR$^{ff}$R$^{gg}$)—, —(C(R$^m$)=C(R$^n$))—, —(C(R$^{mm}$)=C(R$^{nn}$))—, —(C(R$^p$)=N))—, or a single bond, wherein R$^{a1}$, R$^{a2}$, R$^b$, R$^c$, R$^d$, R$^e$, R$^f$, R$^g$, R$^m$, R$^n$, and R$^p$ are independently hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and R$^{bb}$ and R$^{cc}$, R$^{dd}$ and R$^{ee}$, R$^{ff}$ and R$^{gg}$, and R$^{mm}$ and R$^{nn}$ are linked with each other to provide a ring structure, and n1 of —(CR$^f$R$^g$)$_{n1}$— is 1 or 2, when L is —NR$^{a1}$—, —BR$^{a2}$—, —SiR$^b$R$^c$—, —GeR$^d$R$^e$—, —(CR$^f$R$^g$)$_{n1}$—, —(C(R$^m$)=C(R$^n$))—, or —(C(R$^p$)=N))—, L is optionally linked with Ar$^1$ or Ar$^2$ to provide a ring structure, Ar$^3$ is a substituted or unsubstituted C6 to C30 hydrocarbon cyclic group having at least one functional group selected from C=O, C=S, C=Se, and C=Te, or a substituted or unsubstituted C2 to C30 heterocyclic group having at least one functional group selected from C=O, C=S, C=Se, and C=Te, or a fused ring thereof, and R$^1$ and R$^2$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group, a cyano-containing group, a nitro group, a pentafluorosulfanyl group (—SF$_5$), a hydroxyl group, an amine group, a hydrazine group, a hydrazone group, a carboxyl group or a salt thereof, a sulfonic acid group or a salt thereof, a phosphoric acid group or a salt thereof, or —SiR$^a$R$^b$R$^c$, wherein R$^a$, R$^b$, and R$^c$ are independently hydrogen or a substituted or unsubstituted C1 to C10 alkyl group.

2. The compound of claim 1, wherein the compound of Chemical Formula 1 is represented by Chemical Formula 2A:

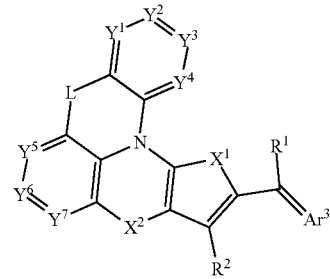

[Chemical Formula 2A]

wherein, in Chemical Formula 2A,

X$^1$, X$^2$, L, Ar$^3$, R$^1$, and R$^2$ are the same as in Chemical Formula 1, and Y$^1$ to Y$^7$ are independently N or CR$^k$, wherein R$^k$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent R$^k$'s are linked to each other to provide a substituted or unsubstituted C6 to C30 arene group, or a substituted or unsubstituted C3 to C30 heteroarene group, or a condensed ring thereof.

3. The compound of claim 2, wherein in Chemical Formula 2A, Y$^4$ is N or CR$^k$, wherein R$^k$ is a halogen, a cyano group, a C1 to C10 haloalkyl group, or a C1 to C10 cyanoalkyl group, or Y$^7$ is N or CR$^k$, wherein R$^k$ is a halogen, a cyano group, a C1 to C10 haloalkyl group, or a C1 to C10 cyanoalkyl group, and X$^2$ is —O—, —S—, —Se—, —Te—, —S(=O)—, —S(=O)$_2$—, —NR$^{a1}$—, —BR$^{a2}$—, —SiR$^b$R$^c$—, —GeR$^d$R$^e$—, —(CR$^f$R$^g$)$_{n1}$—, —(C(R$^m$)=C(R$^n$))—, or —(C(R$^p$)=N))—, wherein R$^{a1}$, R$^{a2}$, R$^b$, R$^c$, R$^d$, R$^e$, R$^f$, R$^g$, R$^m$, R$^n$, and R$^p$ are independently a halogen, a C1 to C20 haloalkyl group, or a C1 to C20 cyanoalkyl group.

4. The compound of claim 1, wherein the compound is represented by Chemical Formula 2A-1 or Chemical Formula 2A-2:

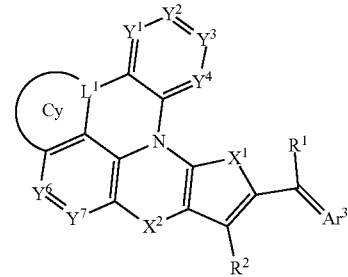

[Chemical Formula 2A-1]

wherein, in Chemical Formula 2A-1,

X$^1$, X$^2$, Ar$^3$, R$^1$, and R$^2$ are the same as in Chemical Formula 1,

L$^1$ is N, B, Si, Ge, or C,

Y$^1$ to Y$^4$, Y$^6$, and Y$^7$ are independently N or CR$^k$, wherein R$^k$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, or a substituted or unsubstituted C3 to C30 heteroarene group, or a condensed ring thereof, and Cy is a substituted or unsubstituted C6 to C30 arene group, a substituted or unsubstituted C3 to C30 heteroarene group, a substituted or unsubstituted C5 to C30 cycloalkene group, or a substituted or unsubstituted C5 to C30 heterocycloalkene group, or a condensed ring thereof,

[Chemical Formula 2A-2]

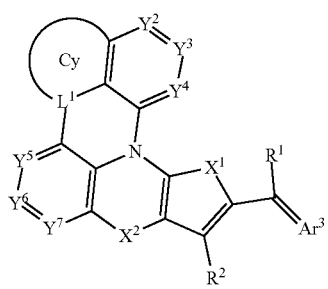

wherein, in Chemical Formula 2A-2, $X^1$, $X^2$, $Ar^3$, $R^1$, and $R^2$ are the same as in Chemical Formula 1, $L^1$ is N, B, Si, Ge, or C, $Y^2$ to $Y^7$ are independently N or $CR^k$, wherein $R^k$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, or a substituted or unsubstituted C3 to C30 heteroarene group, or a condensed ring thereof, and Cy is a substituted or unsubstituted C6 to C30 arene group, a substituted or unsubstituted C3 to C30 heteroarene group, a substituted or unsubstituted C5 to C30 cycloalkene group, or a substituted or unsubstituted C5 to C30 heterocycloalkene group, or a condensed ring thereof.

5. A compound represented by Chemical Formula 2B:

[Chemical Formula 2B]

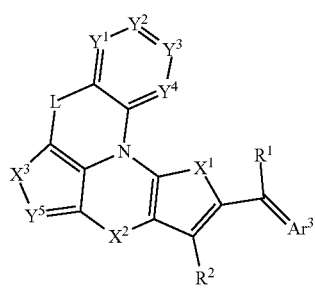

wherein, in Chemical Formula 2B, $X^1$ is —Se—, —Te—, or —$NR^{a1}$—, wherein $R^{a1}$ is hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, $X^2$ is —O—, —S—, —Se—, —Te—, —S(=O)—, —S(=O)$_2$—, —$NR^{a1}$—, —$BR^{a2}$—, —$SiR^bR^c$—, —$SiR^{bb}R^{cc}$—, —$GeR^dR^e$—, —$GeR^{dd}R^{ee}$—, —$(CR^fR^g)_{n1}$—, —$(CR^{ff}R^{gg})$—, —$(C(R^m)=C(R^n))$—, —$(C(R^{mm})=C(R^{nn}))$—, or —$(C(R^p)=N)$—, wherein $R^{a1}$, $R^{a2}$, $R^b$, $R^c$, $R^d$, $R^e$, $R^f$, $R^g$, $R^m$, $R^n$, and $R^p$ are independently hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and $R^{bb}$ and $R^{cc}$, $R^{dd}$ and $R^{ee}$, $R^{ff}$ and $R^{gg}$, and $R^{mm}$ and $R^{nn}$ are linked with each other to provide a ring structure, and n1 of —$(CR^fR^g)_{n1}$— is 1 or 2, $Ar^3$ is a substituted or unsubstituted C6 to C30 hydrocarbon cyclic group having at least one functional group selected from C=O, C=S, C=Se, and C=Te, or a substituted or unsubstituted C2 to C30 heterocyclic group having at least one functional group selected from C=O, C=S, C=Se, and C=Te, or a fused ring thereof, $R^1$ and $R^2$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group, a cyano-containing group, a nitro group, a pentafluorosulfanyl group (—SF$_5$), a hydroxyl group, an amine group, a hydrazine group, a hydrazone group, a carboxyl group or a salt thereof, a sulfonic acid group or a salt thereof, a phosphoric acid group or a salt thereof, or —$SiR^aR^bR^c$, wherein $R^a$, $R^b$, and $R^c$ are independently hydrogen or a substituted or unsubstituted C1 to C10 alkyl group, L is —O—, —S—, —Se—, —Te—, —$NR^{a1}$—, —$BR^{a2}$—, —$SiR^bR^c$—, —$SiR^{bb}R^{cc}$—, —$GeR^dR^e$—, —$GeR^{dd}R^{ee}$—, —$(CR^fR^g)_{n1}$—, —$(CR^{ff}R^{gg})$—, —$(C(R^m)=C(R^n))$—, —$(C(R^{mm})=C(R^{nn}))$—, —$(C(R^p)=N)$—, or a single bond, wherein $R^{a1}$, $R^{a2}$, $R^b$, $R^c$, $R^d$, $R^e$, $R^f$, $R^g$, $R^m$, $R^n$, and $R^p$ are independently hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and $R^{bb}$ and $R^{cc}$, $R^{dd}$ and $R^{ee}$, $R^{ff}$ and $R^{gg}$, and $R^{mm}$ and $R^{nn}$ are linked with each other to provide a ring structure, and n1 of —$(CR^fR^g)_{n1}$— is 1 or 2, $Y^1$ to $Y^5$ are independently N or $CR^k$, wherein $R^k$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent $R^k$'s are linked to each other to provide a substituted or unsubstituted C6 to C30 arene group, or a substituted or unsubstituted C3 to C30 heteroarene group, or a condensed ring thereof, and $X^3$ is —O—, —S—, —Se—, —Te—, —S(=O)—, —S(=O)$_2$—, —$NR^{a1}$—, —$BR^{a2}$—, —$SiR^bR^c$—, —$SiR^{bb}R^{cc}$—, —$GeR^dR^e$—, —$GeR^{dd}R^{ee}$—, —$CR^fR^g$—, or —$CR^{ff}R^{gg}$—, wherein $R^{a1}$, $R^{a2}$, $R^b$, $R^c$, $R^d$, $R^e$, $R^f$, and $R^g$ are independently hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and R$^{bb}$ and R$^{cc}$, R$^{dd}$ and R$^{ee}$, and R$^{ff}$ and R$^{gg}$ are linked to each other to provide a ring structure.

6. The compound of claim 5, wherein
in Chemical Formula 2B, Y$^4$ is N or CR$^k$, wherein R$^k$ is a halogen, a cyano group, a C1 to C10 haloalkyl group, or a C1 to C10 cyanoalkyl group, or
Y$^5$ is N or CR$^k$, wherein R$^k$ is a halogen, a cyano group, a C1 to C10 haloalkyl group, or a C1 to C10 cyanoalkyl group.

7. A compound represented by Chemical Formula 2C:

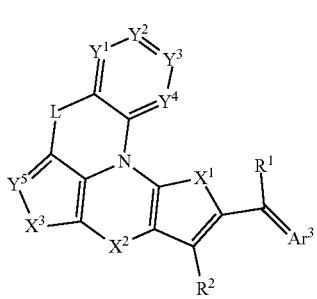

[Chemical Formula 2C]

wherein, in Chemical Formula 2C,

X$^1$ is —Se—, —Te—, or —NR$^{a1}$—, wherein R$^{a1}$ is hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, X$^2$ is —O—, —S—, —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —(CR$^f$R$^g$)$_{n1}$—, —(CR$^{ff}$R$^{gg}$)—, —(C(R$^m$)=C(R$^n$))—, —(C(R$^{mm}$)=C(R$^{nn}$))—, or —(C(R$^p$)=N))—, wherein R$^{a1}$, R$^{a2}$, R$^b$, R$^c$, R$^d$, R$^e$, R$^f$, R$^g$, R$^m$, R$^n$, and R$^p$ are independently hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and R$^{bb}$ and R$^{cc}$, R$^{dd}$ and R$^{ee}$, R$^{ff}$ and R$^{gg}$, and R$^{mm}$ and R$^{nn}$ are linked with each other to provide a ring structure, and n1 of —(CR$^f$R$^g$)$_{n1}$— is 1 or 2, Ar$^3$ is a substituted or unsubstituted C6 to C30 hydrocarbon cyclic group having at least one functional group selected from C=O, C=S, C=Se, and C=Te, or a substituted or unsubstituted C2 to C30 heterocyclic group having at least one functional group selected from C=O, C=S, C=Se, and C=Te, or a fused ring thereof, R$^1$ and R$^2$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group, a cyano-containing group, a nitro group, a pentafluorosulfanyl group (—SF$_5$), a hydroxyl group, an amine group, a hydrazine group, a hydrazone group, a carboxyl group or a salt thereof, a sulfonic acid group or a salt thereof, a phosphoric acid group or a salt thereof, or —SiR$^a$R$^b$R$^c$, wherein R$^a$, R$^b$, and R$^c$ are independently hydrogen or a substituted or unsubstituted C1 to C10 alkyl group, L is —O—, —S—, —Se—, —Te—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —(CR$^f$R$^g$)$_{n1}$—, —(CR$^{ff}$R$^{gg}$)—, —(C(R$^m$)=C(R$^n$))—, —(C(R$^{mm}$)=C(R$^{nn}$))—, —(C(R$^p$)=N))—, or a single bond, wherein R$^{a1}$, R$^{a2}$, R$^b$, R$^c$, R$^d$, R$^e$, R$^f$, R$^g$, R$^m$, R$^n$, and R$^p$ are independently hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and R$^{bb}$ and R$^{cc}$, R$^{dd}$ and R$^{ee}$, R$^{ff}$ and R$^{gg}$, and R$^{mm}$ and R$^{nn}$ are linked with each other to provide a ring structure, and n1 of —(CR$^f$R$^g$)$_{n1}$— is 1 or 2, Y$^1$ to Y$^5$ are independently N or CR$^k$, wherein R$^k$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent R$^k$'s are linked to each other to provide a substituted or unsubstituted C6 to C30 arene group, or a substituted or unsubstituted C3 to C30 heteroarene group, or a condensed ring thereof, and X$^3$ is —O—, —S—, —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —CR$^f$R$^g$—, or —CR$^{ff}$R$^{gg}$—, wherein R$^{a1}$, R$^{a2}$, R$^b$, R$^c$, R$^d$, R$^e$, R$^f$, and R$^g$ are independently hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and R$^{bb}$ and R$^{cc}$, R$^{dd}$ and R$^{ee}$, and R$^{ff}$ and R$^{gg}$ are linked to each other to provide a ring structure.

8. The compound of claim 7, wherein
in Chemical Formula 2C, Y$^4$ is N or CR$^k$, wherein R$^k$ is a halogen, a cyano group, a C1 to C10 haloalkyl group, or a C1 to C10 cyanoalkyl group, or X$^3$ is —O—, —S—, —Se—, —Te—, —S(=O)—, —S(=O)$_2$—, —NR$^{a1}$—, —BR$^{a2}$—, —SiR$^b$R$^c$—, —GeR$^d$R$^e$—, or —CR$^f$R$^g$—, wherein R$^{a1}$, R$^{a2}$, R$^b$, R$^c$, R$^d$, R$^e$, R$^f$, and R$^e$ are independently a halogen, a C1 to C20 haloalkyl group, or a C1 to C20 cyanoalkyl group and X$^2$ is —O—, —S—, —Se—, —Te—, —S(=O)—, —S(=O)$_2$—, —NR$^{a1}$—, —BR$^{a2}$—, —SiR$^b$R$^c$—, —GeR$^d$R$^e$—, —(CR$^f$R$^g$)$_{n1}$—, —(C(R$^m$)=C(R$^n$))—, or —(C(R$^p$)=N))—, wherein R$^{a1}$, R$^{a2}$, R$^b$, R$^c$, R$^d$, R$^e$, R$^f$, R$^g$, R$^m$, R$^n$, and R$^p$ are independently a halogen, a C1 to C20 haloalkyl group, or a C1 to C20 cyanoalkyl group.

9. A compound represented by Chemical Formula 2D:

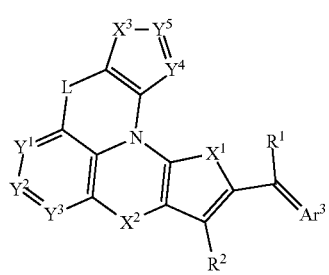

[Chemical Formula 2D]

wherein, in Chemical Formula 2D,

X$^1$ is —Se—, —Te—, or —NR$^{a1}$—, wherein R$^{a1}$ is hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, X$^2$ is —O—, —S—, —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —(CR$^f$R$^g$)$_{n1}$—, —(CR$^{ff}$R$^{gg}$)—, —(C(R$^m$)=C(R$^n$))—, —(C(R$^{mm}$)=C(R$^{nn}$))—, or —(C(R$^p$)=N))—, wherein R$^{a1}$, R$^{a2}$, R$^b$, R$^c$, R$^d$, R$^e$, R$^f$, R$^g$, R$^m$, R$^n$, and R$^p$ are independently hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and R$^{bb}$ and R$^{cc}$, R$^{dd}$ and R$^{ee}$, R$^{ff}$ and R$^{gg}$, and R$^{mm}$ and R$^{nn}$ are linked with each other to provide a ring structure, and n1 of —(CR$^f$R$^g$)$_{n1}$— is 1 or 2, Ar$^3$ is a substituted or unsubstituted C6 to C30 hydrocarbon cyclic group having at least one functional group selected from C=O, C=S, C=Se, and C=Te, or a substituted or unsubstituted C2 to C30 heterocyclic group having at least one functional group selected from C=O, C=S, C=Se, and C=Te, or a fused ring thereof, R$^1$ and R$^2$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group, a cyano-containing group, a nitro group, a pentafluorosulfanyl group (—SF$_5$), a hydroxyl group, an amine group, a hydrazine group, a hydrazone group, a carboxyl group or a salt thereof, a sulfonic acid group or a salt thereof, a phosphoric acid group or a salt thereof, or —SiR$^a$R$^b$R$^c$, wherein R$^a$, R$^b$, and R$^c$ are independently hydrogen or a substituted or unsubstituted C1 to C10 alkyl group, L is —O—, —S—, —Se—, —Te—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —(CR$^f$R$^g$)$_{n1}$—, —(CR$^{ff}$R$^{gg}$)—, —(C(R$^m$)=C(R$^n$))—, —(C(R$^{mm}$)=C(R$^{nn}$))—, —(C(R$^p$)=N))—, or a single bond, wherein R$^{a1}$, R$^{a2}$, R$^b$, R$^c$, R$^d$, R$^e$, R$^f$, R$^g$, R$^m$, R$^n$, and R$^p$ are independently hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and R$^{bb}$ and R$^{cc}$, R$^{dd}$ and R$^{ee}$, R$^{ff}$ and R$^{gg}$, and R$^{mm}$ and R$^{nn}$ are linked with each other to provide a ring structure, and n1 of —(CR$^f$R$^g$)$_{n1}$— is 1 or 2, Y$^1$ to Y$^5$ are independently N or CR$^k$, wherein R$^k$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent R$^k$'s are linked to each other to provide a substituted or unsubstituted C6 to C30 arene group, or a substituted or unsubstituted C3 to C30 heteroarene group, or a condensed ring thereof, and X$^3$ is —O—, —S—, —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —CR$^f$R$^g$—, or —CR$^{ff}$R$^{gg}$—, wherein R$^{a1}$, R$^{a2}$, R$^b$, R$^c$, R$^d$, R$^e$, R$^f$, and R$^g$ are independently hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and R$^{bb}$ and R$^{cc}$, R$^{dd}$ and R$^{ee}$, and R$^{ff}$ and R$^{gg}$ are linked to each other to provide a ring structure.

10. The compound of claim 9, wherein in Chemical Formula 2D, Y$^4$ is N or CR$^k$, wherein R$^k$ is a halogen, a cyano group, a C1 to C10 haloalkyl group, or a C1 to C10 cyanoalkyl group, or Y$^3$ is N or CR$^k$, wherein R$^k$ is a halogen, a cyano group, a C1 to C10 haloalkyl group, or a C1 to C10 cyanoalkyl group, and X$^2$ is —O—, —S—, —Se—, —Te—, —S(=O)—, —S(=O)$_2$—, —NR$^{a1}$—, —BR$^{a2}$—, —SiR$^b$R$^c$—, —GeR$^d$R$^e$—, —(CR$^f$R$^g$)$_{n1}$—, —(C(R$^m$)=C(R$^n$))—, or —(C(R$^p$)=N))—, wherein R$^{a1}$, R$^{a2}$, R$^b$, R$^c$, R$^d$, R$^e$, R$^f$, R$^g$, R$^m$, R$^n$, and R$^p$ are independently a halogen, a C1 to C20 haloalkyl group, or a C1 to C20 cyanoalkyl group.

11. A compound represented by Chemical Formula 2E:

[Chemical Formula 2E]

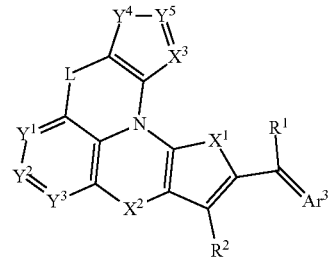

wherein, in Chemical Formula 2E,

X$^1$ is —Se—, —Te—, or —NR$^{a1}$—, wherein R$^{a1}$ is hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, X$^2$ is —O—, —S—, —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —(CR$^f$R$^g$)$_{n1}$—, —(CR$^{ff}$R$^{gg}$)—, —(C(R$^m$)=C(R$^n$))—, —(C(R$^{mm}$)=C(R$^{nn}$))—, or —(C(R$^p$)=N))—, wherein R$^{a1}$, R$^{a2}$, R$^b$, R$^c$, R$^d$, R$^e$, R$^f$, R$^g$, R$^m$, R$^n$, and R$^p$ are independently hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and R$^{bb}$ and R$^{cc}$, R$^{dd}$ and R$^{ee}$, R$^{ff}$ and R$^{gg}$, and R$^{mm}$ and R$^{nn}$ are linked with each other to provide a ring structure, and n1 of —(CR$^f$R$^g$)$_{n1}$— is 1 or 2, Ar$^3$ is a substituted or unsubstituted C6 to C30 hydrocarbon cyclic group having at least one functional group selected from C=O, C=S, C=Se, and C=Te, or a substituted or unsubstituted C2 to C30 heterocyclic group having at least one functional group selected from C=O, C=S, C=Se, and C=Te, or a fused ring thereof, R$^1$ and R$^2$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group, a cyano-containing group, a nitro group, a pentafluorosulfanyl group (—SF$_5$), a hydroxyl group, an amine group, a hydrazine group, a hydrazone group, a carboxyl group or a salt thereof, a sulfonic acid group or a salt thereof, a phosphoric acid group or a salt thereof, or —SiR$^a$R$^b$R$^c$, wherein R$^a$, R$^b$, and R$^c$ are independently hydrogen or a substituted or unsubstituted C1 to C10 alkyl group, L is —O—, —S—, —Se—, —Te—, —NR$^{a1}$—, —BR$^{a2}$—, —SiR$^b$R$^c$—, —SiR$^{bb}$R$^{cc}$—, —GeR$^d$R$^e$—, —GeR$^{dd}$R$^{ee}$—, —(CR$^f$R$^g$)$_{n1}$—, —(CR$^{ff}$R$^{gg}$)—, —(C(R$^m$)=C(R$^n$))—, —(C(R$^{mm}$)=C(R$^{nn}$))—, —(C(R$^p$)=N))—, or a single bond, wherein R$^{a1}$, R$^{a2}$, R$^b$, R$^c$, R$^d$, R$^e$, R$^f$, R$^g$, R$^m$, R$^n$, and R$^p$ are independently hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and R$^{bb}$ and R$^{cc}$, R$^{dd}$ and R$^{ee}$, R$^{ff}$ and R$^{gg}$, and R$^{mm}$ and R$^{nn}$ are linked with each other to provide a ring structure, and n1 of —(CR$^f$R$^g$)$_{n1}$— is 1 or 2, Y$^1$ to Y$^5$ are N or CR$^k$, wherein R$^k$ is hydrogen, deuterium, a halogen, a cyano group, a nitro group, a hydroxyl group, an amine group, a substituted or unsubstituted C1 to C10 alkyl group, or a substituted or unsubstituted C1 to C10 alkoxy group, or adjacent R$^k$'s are linked to each other to provide a substituted or unsubstituted C6 to C30 arene group, or a substituted or unsubstituted C3 to C30 heteroarene group, or a condensed ring thereof, and X$^3$ is —O—, —S—, —Se—, —Te—, —S(=O)—, —S(=O)$_2$—, —NR$^{a1}$—, —BR$^{a2}$—, —SiR$^b$R$^c$—, —GeR$^d$R$^e$—, —GeR$^{dd}$R$^{ee}$—, —CR$^f$R$^g$—, or —CR$^{ff}$R$^{gg}$—, wherein R$^{a1}$, R$^{a2}$, R$^b$, R$^c$, R$^d$, R$^e$, R$^f$, and R$^g$ are independently hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and R$^{bb}$ and R$^{cc}$, R$^{dd}$ and R$^{ee}$, and R$^{ff}$ and R$^{gg}$ are linked to each other to provide a ring structure.

12. The compound of claim 11, wherein
in Chemical Formula 2E,
X$^3$ is —O—, —S—, —Se—, —Te—, —S(=O)—, —S(=O)$_2$—, —NR$^{a1}$—, —BR$^{a2}$—, —SiR$^b$R$^c$—, —GeR$^d$R$^e$—, or —CR$^f$R$^g$—, wherein R$^{a1}$, R$^{a2}$, R$^b$, R$^c$, R$^d$, R$^e$, R$^f$, and R$^g$ are independently a halogen, a C1 to C20 haloalkyl group, or a C1 to C20 cyanoalkyl group, or Y$^3$ is N or CR$^k$, wherein R$^k$ is a halogen, a cyano group, a C1 to C10 haloalkyl group, or a C1 to C10 cyanoalkyl group and X$^2$ is —O—, —S—, —Se—, —Te—, —S(=O)—, —S(=O)$_2$—, —NR$^{a1}$—, —BR$^{a2}$—, —SiR$^b$R$^c$—, —GeR$^d$R$^e$—, —(CR$^f$R$^g$)$_{n1}$—, —(C(R$^m$)=C(R$^n$))—, or —(C(R$^p$)=N))—, wherein R$^{a1}$, R$^{a2}$, R$^b$, R$^c$, R$^d$, R$^e$, R$^f$, R$^g$, R$^m$, R$^n$ and R$^p$ are independently a halogen, a C1 to C20 haloalkyl group, or a C1 to C20 cyanoalkyl group.

13. The compound of claim 1, wherein in X$^2$ and L of Chemical Formula 1, the ring structure is a spiro structure or a fused ring structure.

14. The compound of claim 13, wherein the spiro structure includes a moiety represented by one of moieties (1) to (9):

(1)

(2)

(3)
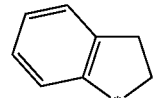

(4)
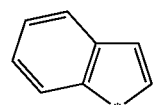

(5)
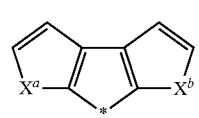

(6)
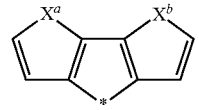

(7)
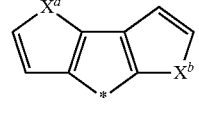

(8)
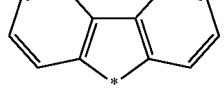

(9)
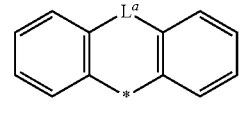

X$^a$ and X$^b$ are independently —O—, —S—, —Se—, —Te—, —S(=O)—, —S(=O)$_2$—, —NR$^{a1}$—, —BR$^{a2}$—, —SiR$^b$R$^c$—, —SiR$^{bb}$R$^{cc}$—, —GeR$^d$R$^e$—, or —GeR$^{dd}$R$^{ee}$—, wherein R$^{a1}$, R$^{a2}$, R$^b$, R$^c$, R$^d$ and R$^e$ are independently hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group, and R$^{bb}$ and R$^{cc}$, and R$^{dd}$ and R$^{ee}$, are linked to each other to provide a ring structure, and L$^a$ is —O—, —S—, —Se—, —Te—, —NR$^{a1}$—, —BR$^{a2}$—, —SiR$^b$R$^c$—, —GeR$^d$R$^e$—, —(CR$^f$R$^g$)$_{n1}$—, —(C(R$^p$)=N))—, or a single bond, wherein R$^{a1}$, R$^{a2}$, R$^b$, R$^c$, R$^d$, R$^e$, R$^f$, R$^g$, and R$^p$ are independently hydrogen, deuterium, a halogen, a substituted or unsubstituted C1 to C20 alkyl group, a substituted or unsubstituted C1 to C20 alkoxy group, a substituted or unsubstituted C6 to C20 aryl group, or a substituted or unsubstituted C6 to C20 aryloxy group.

15. The compound of claim 13, wherein a hydrogen of on each ring is replaced by at least one substituent selected from deuterium, a halogen, a substituted or unsubstituted C1 to C20 alkyl group, a substituted or unsubstituted C1 to C20 alkoxy group, a substituted or unsubstituted C6 to C20 aryl group, and a substituted or unsubstituted C6 to C20 aryloxy group.

16. The compound of claim 14, wherein one or more CH groups present in the aromatic ring of the moieties (3), (4), (5), (6), and (7) is are replaced by N.

17. The compound of claim 1, wherein $Ar^3$ is a cyclic group represented by Chemical Formula 4:

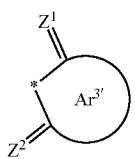

[Chemical Formula 4]

wherein, in Chemical Formula 4,
$Ar^{3'}$ is a substituted or unsubstituted C6 to C30 aryl group, or a substituted or unsubstituted C3 to C30 heteroaryl group,
$Z^1$ is O, S, Se, or Te, and
$Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group.

18. The compound of claim 1, wherein in Chemical Formula 1, $Ar^3$ is a cyclic group represented by one of Chemical Formula 5A to Chemical Formula 5F:

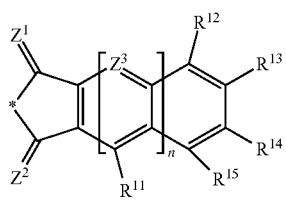

[Chemical Formula 5A]

wherein, in Chemical Formula 5A,
$Z^1$ is O, S, Se, or Te,
$Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group,
$Z^3$ is N or $CR^c$, wherein $R^c$ is hydrogen, deuterium, or a substituted or unsubstituted C1 to C10 alkyl group,
$R^{11}$, $R^{12}$, $R^{13}$, $R^{14}$, and $R^{15}$ are the same or different and are independently hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group, or a cyano-containing group, or a combination thereof, wherein $R^{12}$, $R^{13}$, $R^{14}$, and $R^{15}$ are independently present or are adjacently linked to each other to provide a fused aromatic ring,
n is 0 or 1, and
* is a linking point,

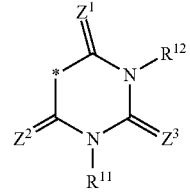

[Chemical Formula 5B]

wherein, in Chemical Formula 5B,
$Z^1$ is O, S, Se, or Te,
$Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group,
$Z^3$ is O, S, Se, Te, or $C(R^a)(CN)$, wherein $R^a$ is hydrogen, a cyano group (CN), or a C1 to C10 alkyl group,
$R^{11}$ and $R^{12}$ are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, or a cyano group (CN), or a combination thereof, and
* is a linking point,

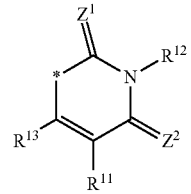

[Chemical Formula 5C]

wherein, in Chemical Formula 5C,
$Z^1$ is O, S, Se, or Te,
$Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group,
$R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, or a cyano group (CN), or a combination thereof, and
* is a linking point,

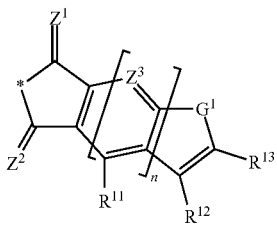

[Chemical Formula 5D]

wherein, in Chemical Formula 5D,
$Z^1$ is O, S, Se, or Te,
$Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group,
$Z^3$ is N or $CR^c$, wherein $R^c$ is hydrogen or a substituted or unsubstituted C1 to C10 alkyl group,
$G^1$ is O, S, Se, Te, $SiR^xR^y$, or $GeR^zR^w$, wherein $R^x$, $R^y$, $R^z$, and $R^w$ are the same or different and are independently hydrogen, deuterium, a halogen, a substituted or unsubstituted C1 to C20 alkyl group, or a substituted or unsubstituted C6 to C20 aryl group,
$R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, or a cyano-containing group, or a combination thereof, wherein $R^{12}$ and $R^{13}$ are independently present or are linked to each other to provide a fused aromatic ring,
n is 0 or 1, and
* is a linking point,

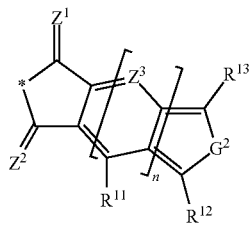

[Chemical Formula 5E]

wherein, in Chemical Formula 5E,
$Z^1$ is O, S, Se, or Te,
$Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group,
$Z^3$ is N or $CR^c$, wherein $R^c$ is hydrogen or a substituted or unsubstituted C1 to C10 alkyl group,
$G^2$ is O, S, Se, Te, $SiR^xR^y$, or $GeR^zR^w$, wherein $R^x$, $R^y$, $R^z$, and $R^w$ are the same or different and are independently hydrogen, deuterium, a halogen, a substituted or unsubstituted C1 to C20 alkyl group, or a substituted or unsubstituted C6 to C20 aryl group,
$R^{11}$, $R^{12}$, and $R^{13}$ are the same or different and are independently hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, or a cyano-containing group, or a combination thereof, and
n is 0 or 1, and
* is a linking point,

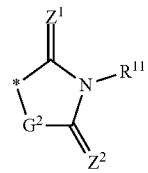

[Chemical Formula 5F]

wherein, in Chemical Formula 5F,
$Z^1$ is O, S, Se, or Te,
$Z^2$ is O, S, Se, Te, or $CR^aR^b$, wherein $R^a$ and $R^b$ are independently hydrogen, a substituted or unsubstituted C1 to C10 alkyl group, a cyano group, or a cyano-containing group, provided that when $Z^2$ is $CR^aR^b$, at least one of $R^a$ and $R^b$ is a cyano group or a cyano-containing group,
$R^{11}$ is hydrogen, deuterium, a substituted or unsubstituted C1 to C30 alkyl group, a substituted or unsubstituted C6 to C30 aryl group, a substituted or unsubstituted C4 to C30 heteroaryl group, a halogen, a cyano group (CN), or a cyano-containing group, or a combination thereof, and
$G^3$ is O, S, Se, Te, $SiR^xR^y$, or $GeR^zR^w$, wherein $R^x$, $R^y$, $R^z$, and $R^w$ are the same or different and are independently hydrogen, deuterium, a halogen, a substituted or unsubstituted C1 to C20 alkyl group, or a substituted or unsubstituted C6 to C20 aryl group.

19. The compound of claim 1, wherein the compound has a maximum absorption wavelength ($\lambda_{max}$) in a wavelength range of greater than or equal to about 500 nm and less than or equal to about 600 nm in a thin film state.

20. The compound of claim 1, wherein the compound exhibits a light absorption curve having a full width at half maximum (FWHM) in a thin film state of about 50 nm to about 110 nm.

21. A photoelectric device, comprising
a first electrode and a second electrode facing each other, and
an active layer between the first electrode and the second electrode,
wherein the active layer comprises the compound of claim 1.

22. An image sensor comprising:
the photoelectric device of claim 21.

23. The image sensor of claim 22, further comprising:
a semiconductor substrate integrated with a plurality of first photo-sensing devices configured to sense light in a blue wavelength region and a plurality of second photo-sensing devices configured to sense light in a red wavelength region, wherein
the photoelectric device is on the semiconductor substrate and configured to selectively sense light in a green wavelength region.

24. The image sensor of claim 23, further comprising:
a color filter layer, wherein
the color filter layer includes a blue filter configured to selectively transmit light in a blue wavelength region and a red filter configured to selectively transmit light in a red wavelength region.

25. The image sensor of claim 23, wherein the plurality of first photo-sensing devices and the plurality of second photo-sensing devices are stacked in a vertical direction in on the semiconductor substrate.

26. The image sensor of claim 22, further comprising:
an organic photoelectric device including the photoelectric device;
a blue photoelectric device configured to selectively absorb light in a blue wavelength region;
a red photoelectric device configured to selectively absorb light in a red wavelength region, wherein
the organic photoelectric device is a green photoelectric device, and
the organic photoelectric device, the blue photoelectric device, and the red photoelectric device are stacked.

27. An electronic device comprising:
the image sensor of claim 22.

* * * * *